(12) United States Patent
Siepe et al.

(10) Patent No.: US 11,064,703 B2
(45) Date of Patent: *Jul. 20, 2021

(54) **ANTIFUNGAL *PAENIBACILLUS* STRAINS, FUSARICIDIN-TYPE COMPOUNDS, AND THEIR USE**

(71) Applicant: BASF SE, Ludwigshafen (DE)

(72) Inventors: Isabella Siepe, Dossenheim (DE); Heike Brueser, Speyer (DE); Kristin Klappach, Neustadt (DE); Karl-Heinrich Schneider, Kleinkarlbach (DE); Petra Sproete, Mannheim (DE); Kerstin Hage, Speyer (DE); Birgit Blanz, Limburgerhof (DE); Eckhard Thines, Mehlingen (DE); Luis Antelo, Hochspeyer (DE); Louis Pergaud Sandjo, Longkak-Yaounde (CM); Till Opatz, Oberursel (DE)

(73) Assignee: BASF SE, Ludwigshafen (DE)

( * ) Notice: Subject to any disclaimer, the term of this patent is extended or adjusted under 35 U.S.C. 154(b) by 425 days.

This patent is subject to a terminal disclaimer.

(21) Appl. No.: 15/724,866

(22) Filed: Oct. 4, 2017

(65) Prior Publication Data
US 2018/0020674 A1    Jan. 25, 2018

Related U.S. Application Data

(62) Division of application No. 15/501,784, filed as application No. PCT/EP2015/067925 on Aug. 4, 2015, now abandoned.

(30) Foreign Application Priority Data

Aug. 4, 2014  (EP) ................................. 14179620

(51) Int. Cl.
  *C07K 14/195*   (2006.01)
  *A01N 63/10*    (2020.01)
  *C12N 1/20*     (2006.01)

(52) U.S. Cl.
  CPC ............ *A01N 63/10* (2020.01); *C07K 14/195* (2013.01); *C12N 1/20* (2013.01)

(58) Field of Classification Search
  CPC .......... C12N 1/20; A61K 47/64; C07K 11/00; C07K 11/02
  See application file for complete search history.

(56) References Cited

U.S. PATENT DOCUMENTS

| 8,652,819 B2 | 2/2014 | Doran Peterson et al. |
| 2013/0217808 A1* | 8/2013 | Sulser ................. C04B 24/2658 524/5 |
| 2014/0147425 A1 | 5/2014 | Henn et al. |

FOREIGN PATENT DOCUMENTS

| CN | 103 146 614 | 7/2014 |
| EP | 1 168 922 | 1/2002 |
| EP | 1 788 074 | 5/2007 |
| KR | 2009 0123158 | 12/2009 |
| KR | 2011 0120020 | 11/2011 |
| KR | 20140075165 A | 6/2014 |
| RU | 2312135 C2 | 12/2007 |
| WO | WO-99/59412 | 11/1999 |
| WO | WO-2006/016558 | 2/2006 |
| WO | WO-2006/017361 | 2/2006 |
| WO | WO-2007/086645 | 8/2007 |
| WO | WO-2011/069227 | 6/2011 |
| WO | WO-2013/086003 A1 | 6/2013 |
| WO | WO-2014/121301 | 8/2014 |
| WO | WO-2014130653 A1 * | 8/2014 ............ A01N 25/00 |

OTHER PUBLICATIONS

Deng et al. "Identification of LI-F type antibiotics and di-n-butyl phthalate produced by Paenibacillus polymyxa" Journal of Microbiological Methods 85 (2011) 175-182 (Year: 2011).*

Tupinamba et al. "Antimicrobial activity of Paenibacillus polymyxa SCE2 against some mycotoxin-producing fungi" Journal of Applied Microbiology 105 (2008) 1044-1053 (Year: 2008).*

Bionda et al., "Effects of Cyclic Lipodepsipeptide Structural Modulation on Stability, Antibacterial Activity, and Human Cell Toxicity," ChemMedChem, 2012, vol. 7, No. 5, pp. 871-882.

Budi et al., "Isolation from the *Sorghum bicolor* Mycorrhizosphere of a Bacterium Compatible with Arbuscular Mycorrhiza Development and Antagonistic towards Soilborne Fungal Pathogens," *Applied and Environmental Microbiology*, 1999, vol. 65, No. 11, pp. 5148-5150.

(Continued)

*Primary Examiner* — Thane Underdahl
(74) *Attorney, Agent, or Firm* — Marshall, Gerstein & Borun LLP

(57) ABSTRACT

The present invention relates to novel isolated bacterial strains, which are members of the genus *Paenibacillus*, originally isolated from soil and showing antagonistic activity against a broad range of pathogens and being capable of producing antimicrobial metabolites. It was found that the strains Lu16774 and Lu17007 belong to a novel subspecies named *Paenibacillus polymyxa* ssp. *plantarum* while the strain Lu17015 belongs to a novel species which is proposed to be *Paenibacillus epiphyticus*. The present invention also relates to microbial pesticide compositions comprising at least one of such novel bacterial strains, whole culture broth or a cell-free extract or a fraction thereof or at least one metabolite thereof, and/or a mutant of at least one of said novel bacterial strains having all the identifying characteristics of the respective bacterial strain or whole culture broth, cell-free extract, fraction and/or metabolite of the mutant thereof showing antagonistic activity against plant pathogens. The present invention also relates to a method of controlling or suppressing plant pathogens or preventing plant pathogen infections by applying such composition. The present invention also relates to novel fusaricidin-type compounds which are metabolites produced by the strains of the present invention.

17 Claims, 24 Drawing Sheets

Specification includes a Sequence Listing.

(56) References Cited

OTHER PUBLICATIONS

Chen et al., "Antifungal peptide produced by *Paenibacillus polymyxa* BRF-1 isolated from soybean rhizosphere," *African Journal of Microbiology Research*, 2010, vol. 4, No. 24, pp. 2692-2698.

Kajimura et al., "Fusaricidin A, a New Depsipeptide Antibiotic Produced by *Bacillus polymyxa* KT-8 Taxonomy, Fermentation, Isolation, Structure Elucidation and Biological Activity," *The Journal of Antibiotics*, 1996, vol. 49, No. 2, pp. 129-135.

Kajimura et al., "Fusaricidins B, C and D, New Depsipeptide Antibiotics Produced by *Bacillus polymyxa* KT-8: Isolation, Structure Elucidation and Biological Activity," *The Journal of Antibiotics*, 1997, vol. 50, No. 3, pp. 220-228.

Kim et al., "Genome Sequence of the Polymyxin-Producing Plant-Probiotic Rhizobacterium Paenibacillus polymyxa E681," *Journal of Bacteriology*, 2010, vol. 192, No. 22, pp. 6103-6104.

Lorentz et al., "Evaluation of antimicrobial activity in *Paenibacillus* spp. strains isolated from natural environment," *Letters in Applied Microbiology*, 2006, vol. 43, No. 5, pp. 541-547.

Raza et al., "Isolation and characterization of fusaricidin-type compound-producing strain of *Paenibacillus polymyxa* SQR-21 active against *Fusarium oxysporum* f.sp. *nevium*," *Eur. J. Plant Pathol.*, 2009, vol. 125, pp. 471-483.

Extended European Search Report dated Jan. 28, 2015 for EP Application No. 14179620.1.

International Search Report dated Oct. 19, 2015 for PCT/EP2015/067925.

International Preliminary Report on Patentability dated Nov. 15, 2016 for PCT/EP2015/067925.

European Search Report dated Mar. 18, 2019 for EP Patent Application No. 19151404.1.

Bionda, et al., "Cyclic lipodepsipeptides: a new class of antibacterial agents in the battle against resistant bacteria", Future Medicinal Chemistry, vol. 5, Issue 11, Jul. 17, 2013, pp. 1311-1330.

Han, et al., "Site-directed modification of the adenylation domain of the fusaricidin nonribosomal peptide synthetase for enhanced production of fusaricidin analogs", Biotechnology Letters, vol. 34, Issue 7, Mar. 27, 2012, pp. 1327-1334.

Li, et al., "Nonribosomal Biosynthesis of Fusaricidins by Paenibacillus polymyxa PKB1 Involves Direct Activation of a d-Amino Acid", Chemistry and Biology, vol. 15, Issue 2, Feb. 22, 2008, pp. 118-127.

* cited by examiner

Compound 5A

Compound 5B a)

| Strain No.* | Identity of the complete 16S rRNA sequence of *Paenibacillus* strains to related taxa based on multiple sequence alignment (%) | | | | | | | | | | | | | | | | | | | | | | | | | | |
|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| 1 | - | | | | | | | | | | | | | | | | | | | | | | | | | | |
| 2 | 99.9 | - | | | | | | | | | | | | | | | | | | | | | | | | | |
| 3 | 100.0 | 99.9 | - | | | | | | | | | | | | | | | | | | | | | | | | |
| 4 | 99.8 | 99.8 | 99.8 | - | | | | | | | | | | | | | | | | | | | | | | | |
| 5 | 94.7 | 94.7 | 94.7 | 94.7 | - | | | | | | | | | | | | | | | | | | | | | | |
| 6 | 99.5 | 99.4 | 99.5 | 99.4 | 94.7 | - | | | | | | | | | | | | | | | | | | | | | |
| 7 | 95.9 | 95.9 | 95.9 | 95.8 | 95.6 | 95.8 | - | | | | | | | | | | | | | | | | | | | | |
| 8 | 93.8 | 93.9 | 93.8 | 93.8 | 96.0 | 93.8 | 94.7 | - | | | | | | | | | | | | | | | | | | | |
| 9 | 94.4 | 94.5 | 94.4 | 94.4 | 95.1 | 94.4 | 95.7 | 95.9 | - | | | | | | | | | | | | | | | | | | |
| 10 | 96.3 | 96.2 | 96.3 | 96.1 | 94.6 | 96.2 | 95.0 | 93.3 | 93.6 | - | | | | | | | | | | | | | | | | | |
| 11 | 100.0 | 99.9 | 100.0 | 99.8 | 94.7 | 99.5 | 95.9 | 93.8 | 94.4 | 96.3 | - | | | | | | | | | | | | | | | | |
| 12 | 99.1 | 99.0 | 99.1 | 99.3 | 94.4 | 98.7 | 96.2 | 93.6 | 94.1 | 96.0 | 99.1 | - | | | | | | | | | | | | | | | |
| 13 | 95.8 | 95.9 | 95.8 | 95.8 | 95.8 | 95.7 | 96.7 | 96.0 | 96.9 | 94.8 | 95.8 | 95.5 | - | | | | | | | | | | | | | | |
| 14 | 95.5 | 95.5 | 95.5 | 95.5 | 95.5 | 95.3 | 96.4 | 96.8 | 98.5 | 94.4 | 95.5 | 94.9 | 97.9 | - | | | | | | | | | | | | | |
| 15 | 95.4 | 95.4 | 95.5 | 95.4 | 95.5 | 95.5 | 95.3 | 94.7 | 94.6 | 94.4 | 95.5 | 95.0 | 95.2 | 95.4 | - | | | | | | | | | | | | |

| Strain No.* | Identity of the complete 16S rRNA sequence of *Paenibacillus* strains to related taxa based on multiple sequence alignment (%) | | | | | | | | | | | | | | | | | | | | | | | | | | |
|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| 16 | 94.4 | 94.2 | 94.3 | 94.1 | 94.6 | 94.2 | 94.4 | 94.0 | 94.2 | 95.2 | 94.3 | 93.7 | 94.7 | 94.7 | 94.6 | - | | | | | | | | | | | |
| 17 | 94.7 | 94.8 | 94.7 | 94.9 | 94.0 | 94.7 | 94.7 | 94.4 | 94.3 | 94.6 | 94.7 | 95.5 | 94.4 | 94.6 | 94.4 | 94.7 | - | | | | | | | | | | |
| 18 | 99.8 | 99.8 | 99.8 | 100.0 | 94.7 | 99.4 | 95.8 | 93.8 | 94.4 | 96.1 | 99.8 | 99.3 | 95.8 | 95.5 | 95.4 | 94.1 | 94.9 | - | | | | | | | | | |
| 19 | 93.8 | 93.9 | 93.6 | 93.8 | 96.8 | 93.7 | 93.9 | 96.1 | 94.5 | 93.7 | 93.8 | 93.6 | 94.7 | 95.1 | 95.1 | 94.0 | 94.4 | 93.8 | - | | | | | | | | |
| 20 | 99.3 | 99.2 | 99.3 | 99.2 | 94.6 | 98.8 | 95.5 | 93.6 | 94.2 | 95.9 | 99.3 | 98.5 | 95.5 | 95.2 | 95.0 | 93.8 | 94.4 | 99.2 | 93.7 | - | | | | | | | |
| 21 | 96.0 | 96.1 | 96.0 | 95.9 | 96.4 | 95.9 | 97.4 | 95.1 | 95.4 | 95.5 | 96.0 | 96.3 | 96.3 | 96.1 | 95.7 | 95.4 | 95.5 | 95.9 | 94.6 | 95.5 | - | | | | | | |
| 22 | 93.2 | 93.1 | 93.2 | 93.1 | 94.8 | 93.1 | 93.6 | 93.9 | 92.8 | 93.6 | 93.2 | 93.3 | 93.6 | 92.9 | 94.2 | 93.1 | 92.4 | 93.1 | 94.2 | 92.9 | 93.9 | - | | | | | |
| 23 | 92.8 | 92.8 | 92.8 | 92.8 | 94.7 | 92.7 | 93.5 | 93.7 | 92.7 | 93.9 | 92.8 | 93.2 | 93.5 | 93.2 | 93.6 | 93.2 | 93.4 | 92.8 | 95.1 | 92.6 | 93.9 | 94.5 | - | | | | |
| 24 | 98.8 | 98.9 | 98.8 | 98.6 | 94.9 | 98.8 | 95.5 | 93.9 | 94.3 | 96.4 | 98.8 | 97.9 | 95.5 | 95.2 | 95.3 | 94.4 | 94.7 | 98.6 | 94.2 | 98.2 | 95.9 | 93.2 | 92.8 | - | | | |
| 25 | 96.0 | 95.9 | 96.0 | 95.9 | 96.2 | 96.0 | 95.5 | 95.4 | 95.7 | 94.9 | 96.0 | 95.3 | 95.8 | 95.6 | 97.6 | 95.3 | 94.7 | 95.9 | 95.8 | 95.5 | 96.1 | 94.3 | 94.4 | 96.4 | - | | |
| 26 | 94.3 | 94.2 | 94.3 | 94.4 | 95.5 | 94.3 | 94.4 | 94.3 | 93.8 | 94.7 | 94.3 | 94.0 | 94.8 | 94.1 | 94.6 | 94.3 | 93.8 | 94.4 | 94.4 | 94.0 | 95.3 | 93.6 | 94.1 | 94.5 | 95.5 | - | |
| 27 | 95.5 | 95.6 | 95.5 | 95.4 | 96.0 | 95.5 | 97.1 | 95.1 | 95.5 | 95.1 | 95.5 | 95.8 | 96.2 | 96.3 | 95.5 | 95.4 | 95.6 | 95.4 | 94.4 | 95.1 | 99.3 | 93.6 | 93.8 | 95.2 | 96.2 | 94.9 | - |
| 28 | 91.5 | 91.4 | 91.5 | 91.5 | 91.4 | 91.3 | 92.6 | 91.5 | 91.6 | 90.2 | 91.5 | 91.9 | 92.4 | 92.1 | 92.1 | 90.9 | 91.6 | 91.5 | 91.2 | 91.1 | 91.6 | 91.3 | 90.9 | 91.0 | 91.8 | 91.1 | 91.6 |

| | Identity of the dnaN DNA sequence of various Paenibacillus strains (%) | | | | | | | | | | | | | | | | | | |
|---|---|---|---|---|---|---|---|---|---|---|---|---|---|---|---|---|---|---|---|
| Strain No.* | 1 | 2 | 3 | 4 | 5 | 6 | 7 | 8 | 9 | 10 | 11 | 12 | 13 | 14 | 15 | 16 | 17 | 18 | 19 |
| 1 | 100 | 100 | 93.3 | 90.6 | 99.4 | 97.3 | 97.2 | 97.2 | 97.3 | 92.9 | 93.3 | 99.3 | 97.4 | 99.3 | 97.2 | 99.5 | 93.5 | 92.5 | 89.6 |
| 2 | - | 100 | 93.3 | 90.6 | 99.4 | 97.3 | 97.2 | 97.2 | 97.3 | 92.9 | 93.3 | 99.3 | 97.4 | 99.3 | 97.2 | 99.5 | 93.5 | 92.5 | 89.6 |
| 3 | - | - | 100 | 90.5 | 93.2 | 93.1 | 93.0 | 93.1 | 92.9 | 97.6 | 98.8 | 93.1 | 93.2 | 93.1 | 93.1 | 93.3 | 99.6 | 97.2 | 90.7 |
| 4 | - | - | - | 100 | 90.3 | 90.4 | 90.4 | 90.6 | 90.5 | 90.4 | 90.4 | 90.3 | 90.5 | 90.3 | 90.6 | 90.4 | 90.7 | 90.0 | 89.5 |
| 5 | - | - | - | - | 100 | 97.0 | 96.9 | 96.9 | 97.0 | 92.6 | 93.2 | 99.4 | 97.1 | 99.4 | 96.9 | 99.7 | 93.4 | 92.0 | 89.3 |
| 6 | - | - | - | - | - | 100 | 99.6 | 99.2 | 99.5 | 92.7 | 93.1 | 96.9 | 99.9 | 96.9 | 99.2 | 97.1 | 93.3 | 92.1 | 89.7 |
| 7 | - | - | - | - | - | - | 100 | 99.1 | 99.6 | 92.6 | 93.0 | 96.9 | 99.7 | 96.9 | 99.1 | 97.0 | 93.3 | 92.0 | 89.7 |
| 8 | - | - | - | - | - | - | - | 100 | 99.4 | 92.7 | 93.1 | 96.9 | 99.3 | 96.9 | 100 | 97.0 | 93.3 | 92.1 | 89.6 |
| 9 | - | - | - | - | - | - | - | - | 100 | 92.7 | 92.9 | 96.9 | 99.6 | 96.9 | 99.4 | 97.1 | 93.2 | 91.9 | 89.3 |
| 10 | - | - | - | - | - | - | - | - | - | 100 | 97.6 | 92.6 | 92.8 | 92.6 | 92.7 | 92.7 | 97.7 | 98.2 | 90.9 |
| 11 | - | - | - | - | - | - | - | - | - | - | 100 | 93.1 | 93.2 | 93.1 | 93.1 | 93.3 | 98.9 | 97.0 | 90.6 |
| 12 | - | - | - | - | - | - | - | - | - | - | - | 100 | 97.0 | 100 | 96.9 | 99.7 | 93.3 | 91.9 | 89.4 |
| 13 | - | - | - | - | - | - | - | - | - | - | - | - | 100 | 97.0 | 99.3 | 97.2 | 93.4 | 92.2 | 89.8 |
| 14 | - | - | - | - | - | - | - | - | - | - | - | - | - | 100 | 96.9 | 99.7 | 93.3 | 91.9 | 89.4 |
| 15 | - | - | - | - | - | - | - | - | - | - | - | - | - | - | 100 | 97.0 | 93.3 | 92.1 | 89.6 |
| 16 | - | - | - | - | - | - | - | - | - | - | - | - | - | - | - | 100 | 93.5 | 92.1 | 89.4 |
| 17 | - | - | - | - | - | - | - | - | - | - | - | - | - | - | - | - | 100 | 97.5 | 91.2 |
| 18 | - | - | - | - | - | - | - | - | - | - | - | - | - | - | - | - | - | 100 | 90.0 |
| 19 | - | - | - | - | - | - | - | - | - | - | - | - | - | - | - | - | - | - | 100 |

Figure 13

| | Identity of the gyrB DNA sequence of various *Paenibacillus* strains (%) | | | | | | | | | | | | | | | | | | |
|---|---|---|---|---|---|---|---|---|---|---|---|---|---|---|---|---|---|---|---|
| Strain No.* | 1 | 2 | 3 | 4 | 5 | 6 | 7 | 8 | 9 | 10 | 11 | 12 | 13 | 14 | 15 | 16 | 17 | 18 | 19 |
| 1 | 100 | 100 | 93.3 | 92.0 | 99.7 | 98.3 | 98.3 | 98.3 | 99.2 | 93.2 | 93.2 | 99.8 | 99.0 | 99.8 | 98.3 | 99.5 | 93.4 | 93.4 | 89.8 |
| 2 | - | 100 | 93.3 | 92.0 | 99.7 | 98.3 | 98.3 | 98.3 | 99.2 | 93.2 | 93.2 | 99.8 | 99.0 | 99.8 | 98.3 | 99.5 | 93.4 | 93.4 | 89.8 |
| 3 | - | - | 100 | 91.7 | 93.2 | 93.0 | 93.0 | 93.0 | 93.0 | 98.2 | 98.1 | 93.2 | 93.2 | 93.2 | 93.0 | 93.2 | 99.0 | 98.2 | 90.0 |
| 4 | - | - | - | 100 | 92.0 | 91.8 | 91.8 | 91.8 | 92.0 | 91.7 | 91.7 | 92.0 | 92.0 | 92.0 | 91.8 | 91.9 | 91.7 | 91.7 | 90.0 |
| 5 | - | - | - | - | 100 | 98.2 | 98.2 | 98.3 | 99.1 | 93.0 | 93.1 | 99.8 | 99.1 | 99.8 | 98.3 | 99.7 | 93.2 | 93.2 | 89.8 |
| 6 | - | - | - | - | - | 100 | 99.8 | 99.7 | 98.8 | 92.7 | 92.9 | 98.3 | 99.0 | 98.3 | 99.7 | 98.1 | 92.9 | 93.2 | 89.4 |
| 7 | - | - | - | - | - | - | 100 | 99.8 | 98.8 | 92.7 | 92.9 | 98.3 | 99.0 | 98.3 | 99.8 | 98.1 | 92.9 | 93.2 | 89.6 |
| 8 | - | - | - | - | - | - | - | 100 | 98.8 | 92.8 | 92.9 | 98.3 | 99.1 | 98.3 | 100 | 98.2 | 93.0 | 93.3 | 89.6 |
| 9 | - | - | - | - | - | - | - | - | 100 | 92.8 | 92.9 | 99.2 | 98.7 | 99.2 | 98.8 | 98.9 | 93.0 | 93.0 | 89.6 |
| 10 | - | - | - | - | - | - | - | - | - | 100 | 97.8 | 93.2 | 93.1 | 93.2 | 92.8 | 93.0 | 98.1 | 97.8 | 89.3 |
| 11 | - | - | - | - | - | - | - | - | - | - | 100 | 93.1 | 93.2 | 93.1 | 92.9 | 93.1 | 98.0 | 98.1 | 89.3 |
| 12 | - | - | - | - | - | - | - | - | - | - | - | 100 | 99.1 | 100 | 98.3 | 99.6 | 93.3 | 93.3 | 89.8 |
| 13 | - | - | - | - | - | - | - | - | - | - | - | - | 100 | 99.1 | 99.1 | 98.9 | 93.3 | 93.4 | 89.7 |
| 14 | - | - | - | - | - | - | - | - | - | - | - | - | - | 100 | 98.3 | 99.6 | 93.3 | 93.3 | 89.8 |
| 15 | - | - | - | - | - | - | - | - | - | - | - | - | - | - | 100 | 98.2 | 93.0 | 93.3 | 89.6 |
| 16 | - | - | - | - | - | - | - | - | - | - | - | - | - | - | - | 100 | 93.2 | 93.2 | 89.7 |
| 17 | - | - | - | - | - | - | - | - | - | - | - | - | - | - | - | - | 100 | 98.0 | 89.8 |
| 18 | - | - | - | - | - | - | - | - | - | - | - | - | - | - | - | - | - | 100 | 89.8 |
| 19 | - | - | - | - | - | - | - | - | - | - | - | - | - | - | - | - | - | - | 100 |

Figure 14

| | Identity of the recF DNA sequence of various *Paenibacillus* strains (%) | | | | | | | | | | | | | | | | | | |
|---|---|---|---|---|---|---|---|---|---|---|---|---|---|---|---|---|---|---|---|
| Strain No.* | 1 | 2 | 3 | 4 | 5 | 6 | 7 | 8 | 9 | 10 | 11 | 12 | 13 | 14 | 15 | 16 | 17 | 18 | 19 |
| 1 | 100 | 100 | 94.7 | 92.2 | 99.0 | 98.1 | 98.2 | 97.8 | 98.1 | 94.0 | 94.9 | 99.0 | 98.1 | 99.0 | 97.8 | 98.8 | 94.5 | 93.7 | 90.2 |
| 2 | - | 100 | 94.7 | 92.2 | 99.0 | 98.1 | 98.2 | 97.8 | 98.1 | 94.0 | 94.9 | 99.0 | 98.1 | 99.0 | 97.8 | 98.8 | 94.5 | 93.7 | 90.2 |
| 3 | - | - | 100 | 93.5 | 95.3 | 95.0 | 95.0 | 94.7 | 95.0 | 98.3 | 99.6 | 95.2 | 94.8 | 95.2 | 94.7 | 95.0 | 99.5 | 97.9 | 92.5 |
| 4 | - | - | - | 100 | 92.7 | 92.8 | 93.0 | 92.6 | 92.8 | 92.6 | 93.5 | 92.7 | 92.8 | 92.7 | 92.6 | 92.5 | 93.5 | 92.5 | 91.8 |
| 5 | - | - | - | - | 100 | 98.5 | 98.6 | 98.2 | 98.5 | 94.6 | 95.5 | 99.8 | 98.3 | 99.8 | 98.2 | 99.5 | 95.2 | 94.0 | 90.8 |
| 6 | - | - | - | - | - | 100 | 99.4 | 99.7 | 100 | 94.3 | 95.0 | 98.5 | 99.6 | 98.5 | 99.7 | 98.3 | 94.8 | 94.0 | 90.8 |
| 7 | - | - | - | - | - | - | 100 | 99.1 | 99.4 | 94.3 | 95.0 | 98.6 | 99.2 | 98.6 | 99.1 | 98.4 | 94.8 | 93.8 | 90.6 |
| 8 | - | - | - | - | - | - | - | 100 | 99.7 | 94.0 | 94.7 | 98.2 | 99.4 | 98.2 | 100 | 98.0 | 94.5 | 93.9 | 90.5 |
| 9 | - | - | - | - | - | - | - | - | 100 | 94.3 | 95.0 | 98.5 | 99.6 | 98.5 | 99.7 | 98.3 | 94.8 | 94.0 | 90.8 |
| 10 | - | - | - | - | - | - | - | - | - | 100 | 98.0 | 94.4 | 94.1 | 94.4 | 94.0 | 94.3 | 98.0 | 97.3 | 91.6 |
| 11 | - | - | - | - | - | - | - | - | - | - | 100 | 95.3 | 94.8 | 95.3 | 94.7 | 95.2 | 99.3 | 97.8 | 92.4 |
| 12 | - | - | - | - | - | - | - | - | - | - | - | 100 | 98.3 | 100 | 98.2 | 99.5 | 95.0 | 93.8 | 90.7 |
| 13 | - | - | - | - | - | - | - | - | - | - | - | - | 100 | 98.3 | 99.4 | 98.1 | 94.6 | 93.8 | 90.6 |
| 14 | - | - | - | - | - | - | - | - | - | - | - | - | - | 100 | 98.2 | 99.5 | 95.0 | 93.8 | 90.7 |
| 15 | - | - | - | - | - | - | - | - | - | - | - | - | - | - | 100 | 98.0 | 94.5 | 93.9 | 90.5 |
| 16 | - | - | - | - | - | - | - | - | - | - | - | - | - | - | - | 100 | 94.8 | 93.6 | 90.9 |
| 17 | - | - | - | - | - | - | - | - | - | - | - | - | - | - | - | - | 100 | 97.7 | 92.3 |
| 18 | - | - | - | - | - | - | - | - | - | - | - | - | - | - | - | - | - | 100 | 91.7 |
| 19 | - | - | - | - | - | - | - | - | - | - | - | - | - | - | - | - | - | - | 100 |

Figure 15

| | Identity of the recN DNA sequence of various Paenibacillus strains (%) | | | | | | | | | | | | | | | | | | |
|---|---|---|---|---|---|---|---|---|---|---|---|---|---|---|---|---|---|---|---|
| Strain No.* | 1 | 2 | 3 | 4 | 5 | 6 | 7 | 8 | 9 | 10 | 11 | 12 | 13 | 14 | 15 | 16 | 17 | 18 | 19 |
| 1 | 100 | 100 | 92.7 | 88.4 | 99.7 | 96.3 | 96.2 | 96.5 | 96.2 | 92.3 | 92.7 | 99.3 | 96.2 | 99.3 | 96.5 | 99.7 | 93.1 | 91.9 | 87.7 |
| 2 | - | 100 | 92.7 | 88.4 | 99.7 | 96.3 | 96.2 | 96.5 | 96.2 | 92.3 | 92.7 | 99.3 | 96.2 | 99.3 | 96.5 | 99.7 | 93.1 | 91.9 | 87.7 |
| 3 | - | - | 100 | 88.6 | 92.8 | 92.0 | 91.9 | 91.9 | 92.1 | 97.6 | 98.8 | 92.4 | 91.9 | 92.4 | 91.9 | 92.8 | 99.1 | 97.0 | 88.2 |
| 4 | - | - | - | 100 | 88.4 | 87.8 | 87.7 | 87.4 | 87.9 | 88.4 | 88.3 | 88.2 | 87.7 | 88.2 | 87.4 | 88.4 | 88.9 | 88.2 | 86.6 |
| 5 | - | - | - | - | 100 | 96.4 | 96.3 | 96.5 | 96.4 | 92.3 | 92.8 | 99.1 | 96.3 | 99.1 | 96.5 | 100 | 93.1 | 91.9 | 87.6 |
| 6 | - | - | - | - | - | 100 | 99.3 | 99.5 | 99.1 | 91.5 | 92.0 | 96.3 | 99.6 | 96.3 | 99.5 | 96.4 | 92.2 | 91.0 | 88.0 |
| 7 | - | - | - | - | - | - | 100 | 99.1 | 99.6 | 91.4 | 92.0 | 96.0 | 99.5 | 96.0 | 99.1 | 96.3 | 92.1 | 90.9 | 87.8 |
| 8 | - | - | - | - | - | - | - | 100 | 98.9 | 91.5 | 91.9 | 96.5 | 99.4 | 96.5 | 100 | 96.5 | 92.1 | 91.0 | 87.6 |
| 9 | - | - | - | - | - | - | - | - | 100 | 91.5 | 92.1 | 96.1 | 99.3 | 96.1 | 98.9 | 96.4 | 92.3 | 90.9 | 87.8 |
| 10 | - | - | - | - | - | - | - | - | - | 100 | 97.7 | 92.0 | 91.4 | 92.0 | 91.5 | 92.3 | 98.1 | 97.4 | 88.4 |
| 11 | - | - | - | - | - | - | - | - | - | - | 100 | 92.4 | 92.0 | 92.4 | 91.9 | 92.8 | 99.1 | 97.1 | 88.0 |
| 12 | - | - | - | - | - | - | - | - | - | - | - | 100 | 96.2 | 100 | 96.5 | 99.1 | 92.7 | 91.6 | 87.7 |
| 13 | - | - | - | - | - | - | - | - | - | - | - | - | 100 | 96.2 | 99.4 | 96.3 | 92.1 | 90.9 | 87.8 |
| 14 | - | - | - | - | - | - | - | - | - | - | - | - | - | 100 | 96.5 | 99.1 | 92.7 | 91.6 | 87.7 |
| 15 | - | - | - | - | - | - | - | - | - | - | - | - | - | - | 100 | 96.5 | 92.1 | 91.0 | 87.6 |
| 16 | - | - | - | - | - | - | - | - | - | - | - | - | - | - | - | 100 | 93.1 | 91.9 | 87.6 |
| 17 | - | - | - | - | - | - | - | - | - | - | - | - | - | - | - | - | 100 | 97.4 | 88.4 |
| 18 | - | - | - | - | - | - | - | - | - | - | - | - | - | - | - | - | - | 100 | 87.7 |
| 19 | - | - | - | - | - | - | - | - | - | - | - | - | - | - | - | - | - | - | 100 |

Figure 16

| | Identity of the rpoA DNA sequence of various *Paenibacillus* strains (%) | | | | | | | | | | | | | | | | | | |
|---|---|---|---|---|---|---|---|---|---|---|---|---|---|---|---|---|---|---|---|
| Strain No.* | 1 | 2 | 3 | 4 | 5 | 6 | 7 | 8 | 9 | 10 | 11 | 12 | 13 | 14 | 15 | 16 | 17 | 18 | 19 |
| 1 | 100 | 100 | 98.2 | 97.7 | 99.9 | 99.6 | 99.4 | 99.5 | 99.4 | 98.0 | 98.1 | 99.9 | 99.6 | 99.9 | 99.5 | 99.9 | 98.0 | 98.0 | 96.2 |
| 2 | - | 100 | 98.2 | 97.7 | 99.9 | 99.6 | 99.4 | 99.5 | 99.4 | 98.0 | 98.1 | 99.9 | 99.6 | 99.9 | 99.5 | 99.9 | 98.0 | 98.0 | 96.2 |
| 3 | - | - | 100 | 98.2 | 98.3 | 98.1 | 97.9 | 98.0 | 97.9 | 99.5 | 99.8 | 98.3 | 98.1 | 98.3 | 98.0 | 98.3 | 99.7 | 99.5 | 96.9 |
| 4 | - | - | - | 100 | 97.8 | 97.9 | 97.9 | 98.0 | 97.9 | 98.1 | 98.4 | 97.8 | 97.9 | 97.8 | 98.0 | 97.8 | 98.3 | 98.1 | 97.5 |
| 5 | - | - | - | - | 100 | 99.7 | 99.5 | 99.6 | 99.5 | 98.1 | 98.2 | 100 | 99.7 | 100 | 99.6 | 100 | 98.1 | 98.1 | 96.3 |
| 6 | - | - | - | - | - | 100 | 99.8 | 99.9 | 99.8 | 98.0 | 98.3 | 99.7 | 100 | 99.7 | 99.9 | 99.7 | 98.2 | 98.0 | 96.4 |
| 7 | - | - | - | - | - | - | 100 | 99.9 | 99.8 | 97.8 | 98.1 | 99.5 | 99.8 | 99.5 | 99.9 | 99.5 | 98.0 | 97.8 | 96.2 |
| 8 | - | - | - | - | - | - | - | 100 | 99.9 | 97.9 | 98.2 | 99.6 | 99.9 | 99.6 | 100 | 99.6 | 98.1 | 97.9 | 96.3 |
| 9 | - | - | - | - | - | - | - | - | 100 | 97.8 | 98.1 | 99.5 | 99.8 | 99.5 | 99.9 | 99.5 | 98.0 | 97.8 | 96.4 |
| 10 | - | - | - | - | - | - | - | - | - | 100 | 99.7 | 98.1 | 98.0 | 98.1 | 97.9 | 98.1 | 99.6 | 100 | 96.8 |
| 11 | - | - | - | - | - | - | - | - | - | - | 100 | 98.2 | 98.3 | 98.2 | 98.2 | 98.2 | 99.9 | 99.7 | 97.1 |
| 12 | - | - | - | - | - | - | - | - | - | - | - | 100 | 99.7 | 100 | 99.6 | 100 | 98.1 | 98.1 | 96.3 |
| 13 | - | - | - | - | - | - | - | - | - | - | - | - | 100 | 99.7 | 99.9 | 99.7 | 98.2 | 98.0 | 96.4 |
| 14 | - | - | - | - | - | - | - | - | - | - | - | - | - | 100 | 99.6 | 100 | 98.1 | 98.1 | 96.3 |
| 15 | - | - | - | - | - | - | - | - | - | - | - | - | - | - | 100 | 99.6 | 98.1 | 97.9 | 96.3 |
| 16 | - | - | - | - | - | - | - | - | - | - | - | - | - | - | - | 100 | 98.1 | 98.1 | 96.3 |
| 17 | - | - | - | - | - | - | - | - | - | - | - | - | - | - | - | - | 100 | 99.6 | 97.0 |
| 18 | - | - | - | - | - | - | - | - | - | - | - | - | - | - | - | - | - | 100 | 96.8 |
| 19 | - | - | - | - | - | - | - | - | - | - | - | - | - | - | - | - | - | - | 100 |

Figure 22

| Strain (No.) | (1) | (2) | (12) | (14) | (7) | (15) | (3) | (11) | (20) | (4) | (19) |
|---|---|---|---|---|---|---|---|---|---|---|---|
| Lu16774 (1) | 100 | 99.99 | 99.2 | 99.3 | 97.50 | 97.6 | 94.82 | 94.59 | 94.8 | 91.78 | 91.73 |
| Lu 17007 (2) | 99.99 | 100 | 99.2 | 99.3 | 97.51 | 97.61 | 94.83 | 94.60 | 94.8 | 91.79 | 91.74 |
| M-1 (12) | 99.22 | 99.23 | 100 | 99.9 | 97.45 | 97.52 | 94.81 | 94.60 | 94.8 | 91.79 | 91.67 |
| SC2 (14) | 99.26 | 99.27 | 99.9 | 100 | 97.45 | 97.54 | 94.84 | 94.63 | 94.8 | 91.81 | 91.72 |
| ATCC 842 = DSM 36 (7) | 97.50 | 97.51 | 97.4 | 97.4 | 100 | 99.12 | 94.90 | 94.64 | 94.8 | 91.79 | 91.72 |
| SQR-21 (15) | 97.60 | 97.61 | 97.5 | 97.5 | 99.12 | 100 | 94.88 | 94.60 | 94.8 | 91.74 | 91.69 |
| Lu17015 (3) | 94.82 | 94.83 | 94.8 | 94.8 | 94.90 | 94.89 | 100 | 98.18 | 99.5 | 92.53 | 92.67 |
| E681 (11) | 94.63 | 94.64 | 94.6 | 94.6 | 94.68 | 94.65 | 98.18 | 100 | 98.1 | 92.34 | 92.51 |
| CR2 (20) | 94.79 | 94.80 | 94.8 | 94.8 | 94.88 | 94.84 | 99.52 | 98.14 | 100 | 92.52 | 92.71 |
| P. peoriae DSM 8320 (4) | 91.78 | 91.79 | 91.8 | 91.8 | 91.82 | 91.77 | 92.53 | 92.28 | 92.5 | 100 | 91.89 |
| P. terrae HPL-003 (19) | 91.73 | 91.74 | 91.7 | 91.7 | 91.74 | 91.72 | 92.67 | 92.48 | 92.7 | 91.88 | 100 |

ANTIFUNGAL *PAENIBACILLUS* STRAINS, FUSARICIDIN-TYPE COMPOUNDS, AND THEIR USE

CROSS-REFERENCE TO RELATED APPLICATIONS

This application is a Divisional of U.S. application Ser. No. 15/501,784, filed Feb. 3, 2017, which is a National Stage application of International Application No. PCT/EP2015/067925, filed Aug. 4, 2015. This application also claims priority under 35 U.S.C. § 119 to European Patent Application No. 14179620.1, filed Aug. 4, 2014.

FIELD OF THE INVENTION

The present invention relates to novel isolated bacterial strains, which are members of the genus *Paenibacillus*, originally isolated from soil and showing antagonistic activity against a broad range of pathogens and being capable of producing antimicrobial metabolites. The present invention also relates to microbial pesticide compositions comprising at least one of such novel bacterial strains, whole culture broth or a cell-free extract or a fraction thereof or at least one metabolite thereof, and/or a mutant of at least one of said novel bacterial strains having all the identifying characteristics of the respective bacterial strain or whole culture broth, cell-free extract, fraction and/or metabolite of the mutant thereof showing antagonistic activity against plant pathogens. The present invention also relates to a method of controlling or suppressing plant pathogens or preventing plant pathogen infections by applying such composition. The present invention also relates to novel fusaricidin-type compounds which are metabolites produced by the strains of the present invention.

BACKGROUND OF THE INVENTION

Reference to Sequence Listing

This application is filed with a Computer Readable Form of a Sequence Listing in accord with 37 C.F.R. § 1.821(c). The text file submitted by EFS, "13779-1333_2017-02-03_Sequence_Listing_ST25," was created on Feb. 1, 2017, has a file size of 37.6 Kbytes, and is hereby incorporated by reference in its entirety.

In the technical field of controlling phytopathogenic fungi affecting plants or crops it is well known to apply active compound compositions comprising biopesticides, for example selected from bacteria, like spore-forming bacteria, or fungi which are not detrimental to the plant or crop to be treated and which biological control agents may be further combined with classical organic chemical antagonists of plant pathogens.

Biopesticides have been defined as a form of pesticides based on micro-organisms (bacteria, fungi, viruses, nematodes, etc.) or natural products (compounds or extracts from biological sources) (U.S. Environmental Protection Agency: http://www.epa.gov/pesticides/biopesticides/).

Biopesticides are typically created by growing and concentrating naturally occurring organisms and/or their metabolites including bacteria and other microbes, fungi, viruses, nematodes, proteins, etc. They are often considered to be important components of integrated pest management (IPM) programmes, and have received much practical attention as substitutes to synthetic chemical plant protection products (PPPs).

Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classed as microbial pesticides, even though they are multi-cellular.

(2) Biochemical pesticides are naturally occurring substances that control pests or provide other crop protection uses as defined below, but are relatively non-toxic to mammals.

For controlling phytopathogenic fungi several microbial pesticides comprising spore-forming bacteria such as *Bacillus subtilis* have been described earlier, see e. g. WO 1998/050422; WO 2000/029426; WO 1998/50422 and WO 2000/58442.

WO 2009/0126473 discloses agriculturally acceptable aqueous compositions comprising bacterial or fungal spores contained in an aqueous/organic solvent and which may further comprise insect control agents, pesticides, fungicides or combinations thereof. Spores of bacteria of the genus *Bacillus* are a preferred species.

WO 2006/017361 discloses compositions for controlling plant pathogens and comprising at least one beneficial bacterium, at least one beneficial fungus, at least on nutrient and at least one compound which extends the effective lifetime of such a composition. The group of beneficial bacteria e.a. comprises bacteria of *Paenibacillus polymyxa* and *Paenibacillus durum*.

EP-A-1 168 922 relates to compositions for affecting plant growth and/or imparting disease resistance comprising at least two plant-growth promoting Rhizobacteria strains and a chitinous compound, wherein said strains are selected from the genera *Bacillus, Paenibacillus, Brevibacillus, Virgibacillus, Alicyclobacillus*, and *Aneurinibacillus*. No particular *Paenibacillus* strains are, however, exemplified in support of the claimed combinations.

WO 1999/059412 discloses a *Paenibacillus polymyxa* strain PKB1 (bearing ATCC accession no. 202127) active against several phytopathogenic fungi.

WO 2006/016558 discloses *Paenibacillus* sp. strains BS-0048, BS-0074, BS-0277 and *P. polymyxa* strain BS-0105 as well as fusaricidin A and fusaricidin B for protection of plants from infections with fungi. A further antifungal *Paenibacillus* strain BRF-1 has been isolated from soybean rhizosphere (African J. Microbiol. Res. 4(24), 2692-2698, 2010).

WO 2011/069227 discloses a *P. polymyxa* strain JB05-01-1 (bearing ATCC accession no. PTA-10436) having a highly inhibitory effect against pathogenic bacteria, predominantly food-borne human pathogenic bacteria.

Budi et al. (Appl Environ Microbiol, 1999, 65, 5148-5150) have isolated *Paenibacillus* sp. strain B2 from mycorrhizosphere of *Sorghum bicolor* having antagonistic activity towards soil borne fungal pathogens like *Phytophthora parasitica*.

A *Paenibacillus peoriae* strain 11.D.3 isolated by Delaporte, B. (Lab Cytol Veg, Paris, France) and deposited in the open collection of Agricultural Research Service, USDA, U.S.A. under the NRRL Accession No. BD-62 (Int. J. Syst Bacteriol. 46(4), 988-1003, 1996, hereinafter also referred to as strain BD-62) from soil in Cote d'Ivoire showed antifungal activity against several phytopathogenic bacteria and fungi (J. Appl. Microbiol. 95, 1143-1151, 2003). NRRL is the abbreviation for the Agricultural Research Service Culture Collection, an international depositary authority for the purposes of depositing microorganism strains under the BUDAPEST TREATY ON THE INTERNATIONAL RECOGNITION OF THE DEPOSIT OF MICROORGANISMS FOR THE PURPOSES OF PATENT PROCEDURE, having the address National Center for Agricultural Utilization Research, Agricultural Research Service, U.S. Department of Agriculture, 1815 North University Street, Peoria, Ill. 61604, USA.

The antimicrobial activity of numerous *Paenibacillus* strains, i. a. a *P. peoriae* strain, against numerous bacterial, fungal and yeast pathogens has been reported elsewhere (Lett. Appl. Microbiol. 43, 541-547, 2006).

Raza et al. (Brazilian Arch. Biol. Techol. 53, 1145-1154, 2010; Eur. J. Plant Pathol. 125: 471-483, 2009) described a fusaricidin-type compound-producing *Paenibacillus polymyxa* strain SQR-21 effective against *Fusarium oxysporum*.

Fusaricidins are a group of antibiotics isolated from *Paenibacillus* spp., which belong to the class of cyclic lipodepsipeptides. Their common structural features which are conserved throughout the family are as follows: a macrocyclic ring consisting of 6 amino acid residues, three of which are L-Thr, D-allo-Thr and D-Ala, as well as the 15-guanidino-3-hydroxypentadecanoic acid tail attached to the N-terminal L-Thr residue by an amide bond (ChemMedChem 7, 871-882, 2012; J. Microbiol. Meth. 85, 175-182, 2011, Table 1 herein). These compounds are cyclized by a lactone bridge between the N-terminal L-Thr hydroxyl group and the C-terminal D-Ala carbonyl group. The position of the amino acid residues within the depsipeptide cycle are usually numbered starting with the abovementioned L-Thr which itself also carries the GHPD chain and ending with the C-terminal D-Ala. Non-limiting examples of fusaricidins isolated from *Paenibacillus* are designated LI-F03, LI-F04, LI-F05, LI-F07 and LI-F08 (J. Antibiotics 40(11), 1506-1514, 1987; Heterocycles 53(7), 1533-1549, 2000; Peptides 32, 1917-1923, 2011) and fusaricidins A (also called LI-F04a), B (also called LI-F04b), C (also called LI-F03a) and D (also called LI-F03b) (J. Antibiotics 49(2), 129-135, 1996; J. Antibiotics 50(3), 220-228, 1997). The amino acid chain of a fusaricidin is not ribosomally generated but is generated by a non-ribosomal peptide synthetase. Structural formulae of known fusaricidins are shown in Table 1 (Biotechnol Lett. 34, 1327-1334, 2012; FIG. 1 therein). The compounds designated as LI-F03a, LI-F03b up to LI-F08a and LI-F08b are herein also referred to as fusaricidins LI-F03a, LI-F03b up to LI-F08a and LI-F08b due to their structure within the fusaricidin family (see Table 1).

TABLE 1

Structures of the fusaricidin family.

| Fusaricidin | X² | X³ | X⁵ |
|---|---|---|---|
| A (LI-F04a) | D-Val | L-Val | D-Asn |
| B (LI-F04b) | D-Val | L-Val | D-Gln |
| C (LI-F03a) | D-Val | L-Tyr | D-Asn |
| D (LI-F03b) | D-Val | L-Tyr | D-Gln |
| LI-F05a | D-Val | L-Ile | D-Asn |
| LI-F05b | D-Val | L-Ile | D-Gln |
| LI-F06a | D-allo-Ile | L-Val | D-Asn |
| LI-F06b | D-allo-Ile | L-Val | D-Gln |
| LI-F07a | D-Val | L-Phe | D-Asn |
| LI-F07b | D-Val | L-Phe | D-Gln |
| LI-F08a | D-Ile | L-allo-Ile | D-Asn |
| LI-F08b | D-Ile | L-allo-Ile | D-Gln |

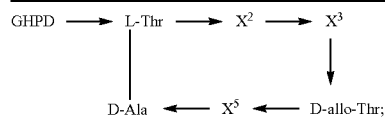

wherein an arrow defines a single (amide) bond either between the carbonyl moiety of GHPD and the amino group of L-Thr (L-threonine) or between the carbonyl group of one amino acid and the amino group of a neighboring amino acid, wherein the tip of the arrow indicates the attachment to the amino group of said amino acid L-Thr or of said neighboring amino acid; and wherein the single line (without an arrow head) defines a single (ester) bond between the carbonyl group of D-Ala (D-alanine) and the hydroxyl group of L-Thr; and wherein GHPD is 15-guanidino-3-hydroxypentadecanoic acid.

Among isolated fusaricidin antibiotics, fusaricidin A has shown the most promising antimicrobial activity against a variety of clinically relevant fungi and gram-positive bacteria such a *Staphylococcus aureus* (MIC value range: 0.78-3.12 µg/ml) (ChemMedChem 7, 871-882, 2012). The synthesis of fusaricidin analogues that contain 12-guanidino-dodecanoic acid (12-GDA) or 12-amino-dodecanoic acid (12-ADA) instead of naturally occurring GHPD has been established but the replacement of GHPD by 12-ADA resulted in complete loss of the antimicrobial activity while the replacement of GHPD by 12-GDA retained antimicrobial activity (Tetrahedron Lett. 47, 8587-8590, 2006; ChemMedChem 7, 871-882, 2012).

Fusaricidins A, B, C and D are also reported to inhibit plant pathogenic fungi such as *Fusarium oxysporum, Aspergillus niger, Aspergillus oryzae*, and *Penicillum thomii* (J. Antibiotics 49(2), 129-135, 1996; J. Antibiotics 50(3), 220-228, 1997). Fusaricidins such as LI-F05, LI-F07 and LI-F08 have been found to have certain antifungal activity against various plant pathogenic fungi such as *Fusarium moniliforme, F. oxysporum, F. roseum, Giberella fujkuroi, Helminthosporium sesamum* and *Penicillium expansum* (J. Antibiotics 40(11), 1506-1514, 1987). Fusaricidins also have antibacterial activity to Gram-positive bacteria including *Staphylococcus aureus* (J. Antibiotics 49, 129-135, 1996; J. Antibiotics 50, 220-228, 1997). In addition, fusaricidins have antifungal activity against *Leptosphaeria maculans* which causes black root rot of canola (Can. J. Microbiol. 48, 159-169, 2002). Moreover, fusaricidins A and B and two related compounds thereof, wherein D-allo-Thr is bound via its hydroxyl group to an additional alanine using an ester bridge, produced by certain *Paenibacillus* strains were found to induce resistance reactions in cultured parsley cells and to inhibit growth of *Fusarium oxysporum* (WO 2006/016558; EP 1 788 074 A1).

WO 2007/086645 describes the fusaricidin synthetase enzyme and its encoding gene as isolated from *Paenibacillus polymyxa* strain E681 which enzyme is involved in the synthesis of fusaricidins A, B, C, D, LI-F03, LI-F04, LI-F05, LI-F07 and LI-F08.

The genome of several *Paenibacillus polymyxa* strains has been published so far: inter alia for strain M-1 (NCBI acc. no. NC_017542; J. Bacteriol. 193 (29), 5862-63, 2011; BMC Microbiol. 13, 137, 2013), strain CR1 (GenBank acc. no. CP006941; Genome Announcements 2 (1), 1, 2014) and strain SC2 (GenBank acc. nos. CP002213 and CP002214; NCBI acc. no. NC_014622; J. Bacteriol. 193 (1), 311-312, 2011), for further strains see legend of FIG. 12 herein. The *P. polymyxa* strain M-1 has been deposited in China General Microbiological Culture Collection Center (CGMCC) under acc. no. CGMCC 7581.

Montefusco et al. describe in Int. J. Systematic Bacteriol. (43, 388-390, 1993) a novel bacterial species of the genus *Bacillus* and suggest the name *Bacillus peoriae* which may be distinguished from other *Bacillus* strains as for example *Bacillus badius, B. coagulans, B. polymyxa* and others. Said novel *Bacillus* strain is reported to produce spores, to be gram-positive and to produce catalase, without producing oxidase. Further biochemical characteristics are summarized therein. The strain, which may be isolated from soil or rotting vegetable materials, was designated BD-57 and was deposited at the Agricultural Research Service, USDA, U.S.A. as NRRL B-14750 and also at the DSMZ (see below) as strain DSM 8320. Based on further biochemical and genetic analysis said strain later has been renamed as *Paenibacillus peoriae* (see Int. J. Systematic Bacteriol. 46, 988-1003, 1996). A more recent assessment of the diversity of *Paenibacillus* spp. in the maize rhizosphere using PCR-DGGE method was described in J. Microbiol. Methods 54, 213-231, 2003.

Biopesticides for use against crop diseases have already established themselves on a variety of crops. For example, biopesticides already play an important role in controlling downy mildew diseases. Their benefits include: a 0-Day Pre-Harvest Interval and the ability to use under moderate to severe disease pressure.

A major growth area for biopesticides is in the area of seed treatments and soil amendments. Biopesticidal seed treatments are e. g. used to control soil borne fungal pathogens that cause seed rots, damping-off, root rot and seedling blights. They can also be used to control internal seed borne fungal pathogens as well as fungal pathogens that are on the surface of the seed. Many biopesticidal products also show capacities to stimulate plant host defenses and other physiological processes that can make treated crops more resistant to a variety of biotic and abiotic stresses.

However, biopesticides under certain conditions can also have disadvantages, such as high specificity (requiring an exact identification of the pest/pathogen and the use of multiple products), slow speed of action (thus making them unsuitable if a pest outbreak is an immediate threat to a crop), variable efficacy due to the influences of various biotic and abiotic factors (since biopesticides are usually living organisms, which bring about pest/pathogen control by multiplying within the target insect pest/pathogen), and resistance development.

Therefore there is a need for further bacterial strains and for further antimicrobial metabolites which antagonize phytopathogenic microorganisms, in particular fungi, which are characterized by a broad spectrum of activity against all classes of phytopathogenic fungi.

DESCRIPTION OF THE INVENTION

Said problem was, surprisingly solved by providing novel strains of bacteria of the genus *Paenibacillus* which are characterized by a unique profile of antagonistic activity against phytopathogenic fungi, also extending to plant leaf pathogens, as for example selected from *Alternaria* spp., *Botrytis cinerea, Phytophthora infestans*, and *Sclerotinia sclerotiorum*. Said bacterial strains have been deposited with the International Depositary Authority: Deutsche Sammlung von Mikroorganismen and Zellkulturen GmbH, Inhoffenstraße 7 B, 38124 Braunschweig, Germany (hereinafter DSMZ).

Furthermore, the whole culture broth, the culture medium and cell-free extracts of these bacterial strains showed inhibitory activity at least against *Alternaria* spp., *Botrytis cinerea* and *Phytophthora infestans*. Bioactivity guided fractionation of organic extracts led to the isolation of two novel fusaricidin-type compounds (compounds 1A and 1 B), the structure of which were elucidated by 1D- and 2D-NMR spectroscopy as well as mass spectrometry.

Thus, the present invention relates to an isolated microorganism, being a member of the family *Paenibacillus*, having at least one of the identifying characteristics of one of the following strains:
1) *Paenibacillus* sp. strain Lu16774 deposited with DSMZ under Accession No. DSM 26969,
2) *Paenibacillus* sp. strain Lu17007 deposited with DSMZ under Accession No. DSM 26970, and
3) *Paenibacillus* sp. strain Lu17015 deposited with DSMZ under Accession No. DSM 26971.

As used herein, the term *Paenibacillus*sp. strain is identical to the term *Paenibacillus* strain.

As used herein, "isolate" refers to a pure microbial culture separated from its natural origin, such an isolate obtained by culturing a single microbial colony. An isolate is a pure culture derived from a heterogeneous, wild population of microorganisms.

As used herein, "strain" refers to isolate or a group of isolates exhibiting phenotypic, physiological, metabolic and/or genotypic traits belonging to the same lineage, distinct from those of other isolates or strains of the same species.

A further embodiment relates to a whole culture broth, a supernatant or a cell-free extract or a fraction or at least one metabolite of at least one of the microorganisms as defined above which preferably exhibit antagonistic activity against at least one plant pathogen.

As used herein, "whole culture broth" refers to a liquid culture of a microorganism containing vegetative cells and/or spores suspended in the culture medium and optionally metabolites produced by the respective microorganism.

As used herein, "culture medium", refers to a medium obtainable by culturing the microorganism in said medium, preferably a liquid broth, and remaining when cells grown in the medium are removed, e. g., the supernatant remaining when cells grown in a liquid broth are removed by centrifugation, filtration, sedimentation, or other means well known in the art; comprising e. g. metabolites produced by the respective microorganism and secreted into the culture medium. The "culture medium" sometimes also referred to as "supernatant" can be obtained e. g. by centrifugation at temperatures of about 2 to 30° C. (more preferably at temperatures of 4 to 20° C.) for about 10 to 60 min (more preferably about 15 to 30 min) at about 5,000 to 20,000×g (more preferably at about 15,000×g).

As used herein, "cell-free extract" refers to an extract of the vegetative cells, spores and/or the whole culture broth of a microorganism comprising cellular metabolites produced by the respective microorganism obtainable by cell disruption methods known in the art such as solvent-based (e. g. organic solvents such as alcohols sometimes in combination with suitable salts), temperature-based, application of shear forces, cell disruption with an ultrasonicator. The desired extract may be concentrated by conventional concentration techniques such as drying, evaporation, centrifugation or alike. Certain washing steps using organic solvents and/or water-based media may also be applied to the crude extract preferably prior to use.

As used herein, the term "metabolite" refers to any component, compound, substance or byproduct (including but not limited to small molecule secondary metabolites, polyketides, fatty acid synthase products, non-ribosomal peptides, ribosomal peptides, proteins and enzymes) produced by a microorganism (such as fungi and bacteria, in particular the strains of the invention) that has any beneficial effect as described herein such as pesticidal activity or improvement of plant growth, water use efficiency of the plant, plant health, plant appearance, or the population of beneficial microorganisms in the soil around the plant activity herein.

As used herein, "isolate" refers to a pure microbial culture separated from its natural origin, such an isolate obtained by culturing a single microbial colony. An isolate is a pure culture derived from a heterogeneous, wild population of microorganisms.

As used herein, "strain" refers to isolate or a group of isolates exhibiting phenotypic and/or genotypic traits belonging to the same lineage, distinct from those of other isolates or strains of the same species.

A further embodiment relates to novel compounds of formula I

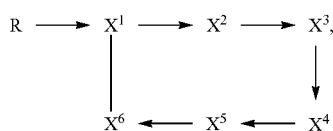

wherein
R is selected from 15-guanidino-3-hydroxypentadecanoic acid (GHPD) and 12-guanidinododecanoic acid (12-GDA);
$X^1$ is threonine;
$X^2$ is isoleucine;
$X^3$ is tyrosine;
$X^4$ is threonine;
$X^5$ is selected from glutamine and asparagine;
$X^6$ is alanine; and
wherein an arrow defines a single (amide) bond either between the carbonyl moiety of R and the amino group of the amino acid $X^1$ or between the carbonyl group of one amino acid and the amino group of a neighboring amino acid, wherein the tip of the arrow indicates the attachment to the amino group of said amino acid $X^1$ or of said neighboring amino acid; and
wherein the single line (without an arrow head) defines a single (ester) bond between the carbonyl group of $X^6$ and the hydroxyl group of $X^1$;
and the agriculturally acceptable salts thereof, and to methods of preparing compounds of formula I of the invention which method comprises culturing the strains of the invention and isolating said compounds of formula I from the whole culture broth.

According to a further embodiment, the invention further relates to compounds 1A and 1B, which are of formula I, wherein R is GHPD and wherein $X^5$ is asparagine in case of compound 1A and $X^5$ is glutamine in case of compound 1B:

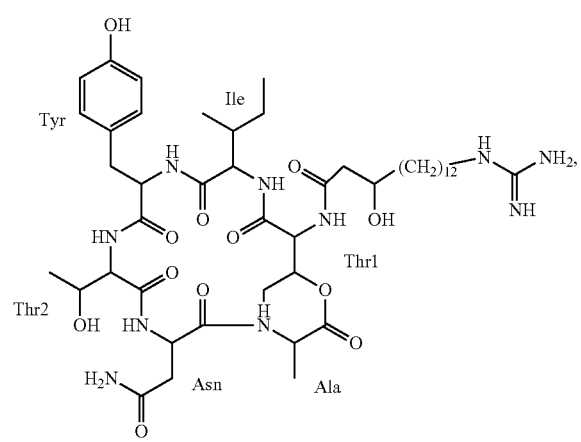

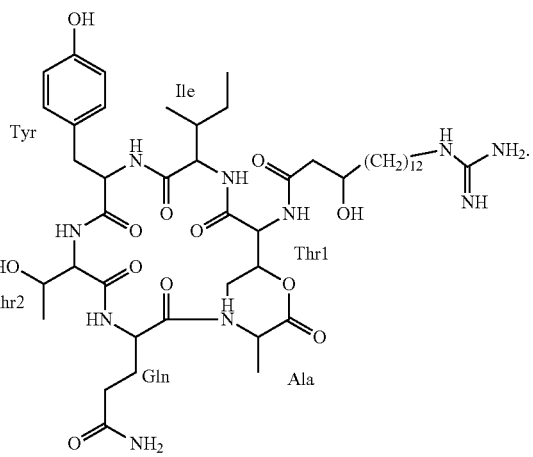

The present invention further relates to compositions comprising the strains, whole culture broth, cell-free extracts, culture media, or compounds of formula I and their salts of the invention, as well as to their use for controlling or suppressing plant pathogens or preventing plant pathogen infection or for protection of materials against infestation destruction by harmful microorganisms, and to corresponding methods which comprise treating the pathogens, their habitat or the materials or plants to be protected against pathogen attack, or the soil or propagation material with an effective amount of the compositions, strains, whole culture broth, cell-free extracts, culture media, or compounds of formula I and their salts of the invention.

Further embodiments of the invention are disclosed in the following detailed description of the invention, the claims and the figures.

The invention relates to the microorganism strains
1) *Paenibacillus* sp. strain Lu16774 deposited with DSMZ under Accession No. DSM 26969,
2) *Paenibacillus* sp. strain Lu17007 deposited with DSMZ under Accession No. DSM 26970, and
3) *Paenibacillus* sp. strain Lu17015 deposited with DSMZ under Accession No. DSM 26971.

The strains Lu16774, Lu17007 and Lu17015 have been isolated from soil samples from a variety of European locations including Germany and deposited under the Budapest Treaty with the Deutsche Sammlung von Mikroorganismen und Zellkulturen (DSMZ) under the abovementioned Accession numbers on Feb. 20, 2013 by BASF SE, Germany.

The genus *Paenibacillus* (formerly rRNA group 3 bacilli) has been characterized phenotypically and physiologically (Antonie van Leeuwenhoek 64, 253-260 (1993)) by:
rod-shaped cells of Gram-positive structure,
weak reaction with Gram's stain, often even stain negatively,
differentiation into ellipsoidal endospores which distinctly swell the sporangium (mother cell),
facultative anaerobic growth with strong growth in absence of air irrespective of whether nitrate is present or not,
fermentation of a variety of sugars,
acid and gas formation from various sugars including glucose,
no acid production from adonitol and sorbitol,
Urease-negative (with exception of *P. validus*), arginine dihydrolase negative,
no utilization of citrate,
no growth in presence of 10% sodium chloride,
secretion of numerous extracellular hydrolytic enzymes degrading DNA, protein, starch; and/or
G+C content of DNA from 40% to 54%.

The genus *Paenibacillus* (formerly rRNA group 3 bacilli) has also been characterized by 16S rDNA analysis (Antonie van Leeuwenhoek 64, 253-260 (1993)):

having a specific 22-base sequence in a variable region V5 of the 16S rDNA (5' to 3'): TCGA-TACCCTTGGTGCCGAAGT (Antonie van Leeuwenhoek 64, 253-260 (1993), see Table 3 therein); and/or
by hybridization of isolated or PCR-amplified chromosomal DNA with BG3 probe (5'-TCGA-TACCCTTGGTGCCGAAGT-3') (see Antonie van Leeuwenhoek 64, 253-260 (1993)).

The deposited strains Lu16774, Lu17007 and Lu17015 of the invention were determined to belong to the genus *Paenibacillus* on the following morphological and physiological observations (see Example 2.3 herein):
rod-shaped cells
ellipsoidal spores
swollen sporangium
anaerobic growth
fermentation of a variety of sugars including glucose, arabinose, xylose, mannit, fructose, raffinose, trehalose and glycerol with acid formation
gas production from glucose
arginine dihydrolase negative
no utilization of citrate
no growth in presence of 5% or more sodium chloride
production of extracellular hydrolytic enzymes degrading starch, gelatine, casein and esculin.

Further, the deposited strains Lu16774, Lu17007 and Lu17015 of the invention were also determined to belong to the genus *Paenibacillus* by 16S rDNA analysis by having the *Paenibacillus*-specific 22-base sequence in 16S rDNA (5' to 3'):

```
5'-TCGATACCCTTGGTGCCGAAGT-3'
```

(see SEQ ID NO:1 (nucleotides 840-861), SEQ ID NO:2 (840-861), SEQ ID NO:3 (844-865) and SEQ ID NO:4 (840-861) in sequence listings herein).

Further, sequencing of the complete 16S rDNA in comparison to 24 different *Paenibacillus* strains resulted in clustering of the deposited strains Lu16774, Lu17007 and Lu17015 with the type strains of *Paenibacillus brasiliensis*, *P. kribbensis*, *P. jamilae*, *P. peoriae*, and *P. polymyxa*, more preferably to *P. peoriae*, in particular *Paenibacillus peoriae* strain BD-62 (see FIGS. 1 and 2 herein). It is known that *P. polymyxa* and *P. peoriae* have 16S rDNA sequence identity values of 99.6 to 99.7% (J. Gen. Appl. Microbiol. 48, 281-285 (2002)).

"Percent Identity" or "percent similarity" between two nucleotide sequences means percent identity of the residues over the complete length of the aligned sequences and is determined by comparing two optimally locally aligned sequences over a comparison window defined by the length of the local alignment between the two sequences, such as, for example, the identity calculated (for rather similar sequences) after manual alignment with the aid of the program AE2 (Alignment Editor 2). Local alignment between two sequences only includes segments of each sequence that are deemed to be sufficiently similar according to the criterion that depends on the algorithm used to perform the alignment (e. g. AE2, BLAST, secondary structure of the rRNA molecule or alike). The percentage identity is calculated by determining the number of positions at which the identical nucleic acid occurs in both sequences to yield the number of matched positions, dividing the number of matched positions by the total number of positions in the window of comparison and multiplying the result by 100.

To determine the percent sequence identity of two nucleic acid sequences (e. g., one of the nucleotide sequences of Table 1 and a homolog thereof), the sequences are aligned for optimal comparison purposes (e. g., gaps can be introduced in the sequence of one nucleic acid for optimal alignment with the other nucleic acid). The bases at corresponding positions are then compared. When a position in one sequence is occupied by the base as the corresponding position in the other sequence then the molecules are identical at that position. It is to be understood that for the purposes of determining sequence identity when comparing a DNA sequence to an RNA sequence, a thymidine nucleotide is equivalent to a uracil nucleotide.

For alignment, the sequence data was put into the program AE2 (http://iubio.bio.indiana.edu/soft/molbio/unix/ae2.readme), aligned manually according to the secondary structure of the resulting rRNA molecule and compared with representative 16S rRNA gene sequences of organisms belonging to the *Firmicutes* (Nucl. Acids Res. 27, 171-173, 1999). To obtain % identity values for multiple sequences, all sequences of were aligned with each other (multiple sequence alignment). Further, to obtain % identity values between two sequences over a longer stretch of aligned sequences in comparison to multiple alignment, a manual pairwise sequence alignment was done as described above using AE2 (pairwise sequence alignment).

Further, standardized, automated ribotyping is performed using the Qualicon RiboPrintersystem with the *Paenibacillus* strains Lu16774, Lu17007 and Lu17015 in comparison to the *P. peoriae* BD-62 using the restriction enzyme EcoRI resulted in similarity of all three novel strains to *P. peoriae* BD-62 of between 0.24 and 0.5 (Example 2.2 and FIG. 12).

In sum, the strains have been designated to the following taxonomic groups.

The *Paenibacillus* strains Lu16774 and Lu17007 both belong to the species *Paenibacillus polymyxa*.

Thus, the invention relates to the microorganism strains
1) *Paenibacillus polymyxa* strain Lu16774 deposited with DSMZ under Accession No. DSM 26969,
2) *Paenibacillus polymyxa* strain Lu17007 deposited with DSMZ under Accession No. DSM 26970, and
3) *Paenibacillus* sp. strain Lu17015 deposited with DSMZ under Accession No. DSM 26971.

According to the results of the phylogenetic analysis presented herein (FIGS. 12 to 22) and unpublished results of Professor Borriss, Germany, it is proposed that the heterogenous species *Paenibacillus polymyxa* requires a new taxonomic classification into two subspecies: 1) *Paenibacillus polymyxa* ssp. *polymyxa* and 2) *Paenibacillus polymyxa* ssp. *plantarum*; and 3) a novel species *Paenibacillus* nov. spec. *epiphyticus*.

The type strain *P. polymyxa* DSM 36 together with the *P. polymyxa* strains SQR-21, CF05, CICC 10580, NRRL B-30509 and A18 form in each of the maximum likelihood dendrograms analysed for five conserved house keeping genes (dnaN, gyrB, recA, recN and rpoA) a separate cluster (FIGS. 17-21).

Very similar results have been obtained by determination of the Average Amino acid Identity (AAI) which is frequently used for determination of phylogenetic relationship amongst bacterial species. This method is based on the calculation of the average identity of a core genome on amino acid level (Proc. Natl. Acad. USA 102, 2567-2572, 2005). According to the resulting AAI-matrix in FIG. 22, *P. polymyxa* DSM 36 forms together with the *P. polymyxa* SQR-21 strain a sub cluster that is different from the two other sub clusters shown therein.

The strains Lu16674 and Lu17007 together with strain *P. polymyxa* M-1, 1-43, SC2 and Sb3-1 form the second sub cluster in each of the maximum likelihood dendrograms analysed for five conserved house keeping genes (dnaN, gyrB, recA, recN and rpoA) (FIGS. 17-21). According to AAI-matrix in FIG. 22 based on the analysis of the core genome, this second sub cluster is confirmed by its representative strains Lu16674 and Lu17007 together with the *P. polymyxa* M-1 and SC2 strains.

The difference between the two sub clusters is not so significant to justify a new species, but the AAI identify levels between the representatives of both clusters is of about 97.5% justifying the classification into two separate subspecies Thus, it is proposed to nominate the first sub cluster according to the type *P. polymyxa* strain DSM 36$^T$ *Paenibacillus polymyxa* ssp. *polymyxa*. Besides strain DSM 36, the *P. polymyxa* strains SQR-21, CF05, CICC 10580, NRRL B-30509 and A18 shall belong to the subspecies *Paenibacillus polymyxa* ssp. *polymyxa*.

Further, it is proposed to nominate the second sub cluster as novel subspecies *Paenibacillus polymyxa* ssp. *plantarum*. Besides the strains Lu16674 and Lu17007, the *P. polymyxa* strains M-1, 1-43, SC2 and Sb3-1 shall belong to *Paenibacillus polymyxa* ssp. *plantarum*.

The strain Lu17015 has only 94.9% identity (AAI) amongst the genes of the core genome with the type strain *Paenibacillus polymyxa* DSM36=ATCC 842 (FIG. 22). Thus, the strain Lu17015 could not have been designated to the species *Paenibacillus polymyxa* nor to any other known *Paenibacillus* species. Similar values are found for the strains E681 (94.7%) and CR2 (94.9%). Amongst each other, these three strains have at least 98.1% identity (AAI). According to the species definition of Konstantinides and Tiedje (Proc Natl. Acad. Sci. USA. 102, 2567-2572, 2005), the strain Lu17015 and also the strains E681 and CR2 can be designated to a novel species. Thus, a new species *Paenibacillus* spec. nov. *epiphyticus* is proposed herewith. Consequently, the *Paenibacillus* strain Lu17015 belongs to *Paenibacillus epiphyticus*. It is proposed that said strain shall be the type strain. Likewise, the dendrograms based on the sequence comparisons of the five house keeping genes (FIGS. 17-21) show that this cluster of distant from all other *P. polymyxa* strains. Besides Lu17015, it is proposed that the *P. polymyxa* strains E681, CR2 TD94, DSM 365 and WLY78 shall belong to *Paenibacillus* spec. nov. *epiphyticus*.

Thus, the invention relates to the microorganism strains
4) *Paenibacillus polymyxa* ssp. *plantarum* strain Lu16774 deposited with DSMZ under Accession No. DSM 26969,
5) *Paenibacillus polymyxa* ssp. *plantarum* strain Lu17007 deposited with DSMZ under Accession No. DSM 26970, and
6) *Paenibacillus epiphyticus* strain Lu17015 deposited with DSMZ under Accession No. DSM 26971.

In addition to the strains Lu16774, Lu17007 and Lu17015, the invention relates to any *Paenibacillus* strain, whether physically derived from the original deposit of any of the strains Lu16774, Lu17007 and Lu17015 or independently isolated, so long as they retain at least one of the identifying characteristics of the deposited *Paenibacillus* strains Lu16774, Lu17007 and Lu17015. Such *Paenibacillus* strains of the invention include any progeny of any of the strains Lu16774, Lu17007 and Lu17015, including mutants of said strains.

The term "mutant" refers a microorganism obtained by direct mutant selection but also includes microorganisms that have been further mutagenized or otherwise manipulated (e. g., via the introduction of a plasmid). Accordingly, embodiments include mutants, variants, and or derivatives of the respective microorganism, both naturally occurring and artificially induced mutants. For example, mutants may be induced by subjecting the microorganism to known mutagens, such as X-ray, UV radiation or N-methyl-nitrosoguanidine, using conventional methods. Subsequent to said treatments a screening for mutant strains showing the desired characteristics may be performed.

Mutant strains may be obtained by any methods known in the art such as direct mutant selection, chemical mutagenesis or genetic manipulation (e. g., via the introduction of a plasmid). For example, such mutants are obtainable by applying a known mutagen, such as X-ray, UV radiation or N-methyl-nitrosoguanidine. Subsequent to said treatments a screening for mutant strains showing the desired characteristics may be performed.

A *Paenibacillus* strain of the invention is in particular one which comprises a DNA sequence exhibiting at least at least 99.6%, preferably at least 99.8%, even more preferably at least 99.9%, and in particular 100.0% nucleotide sequence identity to any one of the 16S rDNA sequences of the strains Lu16774, Lu17007 and Lu17015, i.e. to any one of those nucleotide sequences set forth in the Sequence listing being SEQ ID NO:1, SEQ ID NO:2 and SEQ ID NO:3.

According to a further embodiment, a *Paenibacillus* strain of the invention is in particular one which comprises a DNA sequence exhibiting 100% nucleotide sequence identity to any one of the 16S rDNA sequences of the strains Lu16774, Lu17007 and Lu17015, i.e. to any one of those nucleotide sequences set forth in the Sequence listing being SEQ ID NO:1, SEQ ID NO:2 or SEQ ID NO:3.

According to a further embodiment, a *Paenibacillus* strain of the invention is one whose complete 16S rDNA sequence has after optimal alignment within the aligned sequence window at least 99.6% identity to at least one of the sequences SEQ ID NO:1 and SEQ ID NO:2 or at least 99.8% identity to SEQ ID NO:3; preferably at least 99.8% identity to at least one of the sequences SEQ ID NO:1, SEQ ID:2 and SEQ ID NO:3; more preferably at least 99.9% identity to at least one of the sequences SEQ ID NO:1, SEQ ID NO:2 and SEQ ID NO:3; even more preferably greater than 99.9% identity to at least one of the sequences SEQ ID NO:1, SEQ ID:2 and SEQ ID NO:3; in particular 100% identity to at least one of the sequences SEQ ID NO:1, SEQ ID:2 and SEQ ID NO:3.

According to a further embodiment, a *Paenibacillus* strain of the invention is selected from the group consisting of:
a) strain Lu16774 deposited with DSMZ under Accession No. DSM 26969;
b) strain Lu17007 deposited with DSMZ under Accession No. DSM 26970;
c) strain Lu17015 deposited with DSMZ under Accession No. DSM 26971; and
d) a strain which comprises a DNA sequence exhibiting
  d1) at least 99.6% nucleotide sequence identity to the DNA sequences SEQ ID NO:4 or SEQ ID NO:9; or d2) at least 99.8% nucleotide sequence identity to the
DNA sequence SEQ ID NO:14; or
d3) at least 99.9% nucleotide sequence identity to the
DNA sequences SEQ ID NO:5 or SEQ ID NO:10; or
d4) at least 99.2% nucleotide sequence identity to the
DNA sequence SEQ ID NO:15; or
d5) at least 99.2% nucleotide sequence identity to the
DNA sequences SEQ ID NO:6 or SEQ ID NO:11; or
d6) at least 99.8% nucleotide sequence identity to the
DNA sequence SEQ ID NO:16; or
d7) at least 99.8% nucleotide sequence identity to the
DNA sequences SEQ ID NO:7 or SEQ ID NO:12; or
d8) at least 99.3% nucleotide sequence identity to the
DNA sequence SEQ ID NO:17; or
d9) 100.0% nucleotide sequence identity to the DNA sequences SEQ ID NO:8 or SEQ ID NO:13; or
d10) at least 99.8% nucleotide sequence identity to the
DNA sequence SEQ ID NO:18.

A *Paenibacillus* strain of the invention is in particular one which comprises a dnaN DNA sequence exhibiting at least 99.6% nucleotide sequence identity to the DNA sequences SEQ ID NO:4 or SEQ ID NO:9 or which comprises a DNA sequence exhibiting at least 99.8% nucleotide sequence identity to the DNA sequence SEQ ID NO:14.

According to a further embodiment, a *Paenibacillus* strain of the invention is one whose complete dnaN DNA sequence has after optimal alignment within the aligned sequence window at least 99.6% identity to at least one of the DNA sequences SEQ ID NO:4 and SEQ ID NO:9 or at least 99.8% identity to SEQ ID NO:14; preferably at least 99.9% identity to SEQ ID NO:14; in particular 100% identity to SEQ ID NO:14.

A *Paenibacillus* strain of the invention is in particular one which comprises a DNA sequence exhibiting at least 99.8%, in particular 100.0% nucleotide sequence identity to any one of the dnaN DNA sequences of the strains Lu16774, Lu17007 and Lu17015, i.e. to any one of those DNA sequences SEQ ID NO:4, SEQ ID NO:9 and SEQ ID NO:14.

A *Paenibacillus* strain of the invention is in particular one which comprises a gyrB DNA sequence exhibiting at least 99.9% nucleotide sequence identity to the DNA sequences SEQ ID NO:5 or SEQ ID NO:10 or which comprises a DNA sequence exhibiting at least 99.2% nucleotide sequence identity to the DNA sequence SEQ ID NO:15.

According to a further embodiment, a *Paenibacillus* strain of the invention is one whose complete gyrB DNA sequence has after optimal alignment within the aligned sequence window at least 99.9% identity to at least one of the DNA sequences SEQ ID NO:5 and SEQ ID NO:10 or at least 99.9% identity to SEQ ID NO:15; preferably at least 99.9% identity to SEQ ID NO:15; in particular 100% identity to SEQ ID NO:15.

A *Paenibacillus* strain of the invention is in particular one which comprises a DNA sequence exhibiting 100.0% nucleotide sequence identity to any one of the gyrB DNA sequences of the strains Lu16774, Lu17007 and Lu17015, i.e. to any one of those DNA sequences SEQ ID NO:5, SEQ ID NO:10 and SEQ ID NO:15.

A *Paenibacillus* strain of the invention is in particular one which comprises a recF DNA sequence exhibiting at least 99.2% nucleotide sequence identity to the DNA sequences SEQ ID NO:6 or SEQ ID NO:11 or which comprises a DNA sequence exhibiting at least 99.8% nucleotide sequence identity to the DNA sequence SEQ ID NO:16.

According to a further embodiment, a *Paenibacillus* strain of the invention is one whose complete recF DNA sequence has after optimal alignment within the aligned sequence window at least 99.2% identity to at least one of the DNA sequences SEQ ID NO:6 and SEQ ID NO:11 or at least 99.8% identity to SEQ ID NO:16; preferably at least 99.9% identity to SEQ ID NO:16; in particular 100% identity to SEQ ID NO:16.

A *Paenibacillus* strain of the invention is in particular one which comprises a DNA sequence exhibiting at least 99.8%, in particular 100.0% nucleotide sequence identity to any one of the recF DNA sequences of the strains Lu16774, Lu17007 and Lu17015, i.e. to any one of those DNA sequences SEQ ID NO:6, SEQ ID NO:11 and SEQ ID NO:16.

A *Paenibacillus* strain of the invention is in particular one which comprises a recN DNA sequence exhibiting at least 99.8% nucleotide sequence identity to the DNA sequences SEQ ID NO:7 or SEQ ID NO:12 or which comprises a DNA sequence exhibiting at least 99.3% nucleotide sequence identity to the DNA sequence SEQ ID NO:17.

According to a further embodiment, a *Paenibacillus* strain of the invention is one whose complete recN DNA sequence has after optimal alignment within the aligned sequence window at least 99.8% identity to at least one of the DNA sequences SEQ ID NO:7 and SEQ ID NO:12 or at least 99.3% identity to SEQ ID NO:17; preferably at least 99.6% identity to SEQ ID NO:17; in particular 100% identity to SEQ ID NO:17.

A *Paenibacillus* strain of the invention is in particular one which comprises a DNA sequence exhibiting at least 99.8%, in particular 100.0% nucleotide sequence identity to any one of the recN DNA sequences of the strains Lu16774, Lu17007 and Lu17015, i.e. to any one of those DNA sequences SEQ ID NO:7, SEQ ID NO:12 and SEQ ID NO:17.

A *Paenibacillus* strain of the invention is in particular one which comprises a rpoA DNA sequence exhibiting 100.0% nucleotide sequence identity to the DNA sequences SEQ ID NO:8 or SEQ ID NO:13 or which comprises a DNA sequence exhibiting at least 99.8% nucleotide sequence identity to the DNA sequence SEQ ID NO:18.

According to a further embodiment, a *Paenibacillus* strain of the invention is one whose complete rpoA DNA sequence has after optimal alignment within the aligned sequence window 100.0% identity to at least one of the DNA sequences SEQ ID NO:8 and SEQ ID NO:13 or at least 99.8% identity to SEQ ID NO:18; preferably at least 99.9% identity to SEQ ID NO:17; in particular 100% identity to SEQ ID NO:18.

A *Paenibacillus* strain of the invention is in particular one which comprises a DNA sequence exhibiting 100.0% nucleotide sequence identity to any one of the rpoA DNA sequences of the strains Lu16774, Lu17007 and Lu17015, i.e. to any one of those DNA sequences SEQ ID NO:8, SEQ ID NO:13 and SEQ ID NO:18.

A further embodiment relates to an isolated microorganism, being a member of the family *Paenibacillus*, having at least one of the identifying characteristics of one of the following strains:
1) *Paenibacillus* strain Lu16774 deposited with DSMZ under Accession No. DSM 26969,
2) *Paenibacillus* strain Lu17007 deposited with DSMZ under Accession No. DSM 26970, or
3) *Paenibacillus* strain Lu17015 deposited with DSMZ under Accession No. DSM 26971.

A further embodiment relates to a *Paenibacillus* strain, which is selected from the group consisting of:
1) strain Lu16774 deposited with DSMZ under Accession No. DSM 26969, 2) strain Lu17007 deposited with DSMZ under Accession No. DSM 26970, and
3) strain Lu17015 deposited with DSMZ under Accession No. DSM 26971,
4) strains having at least one of the identifying characteristics of one of said strains Lu16774, Lu17007 and Lu17015.

Another embodiment of the invention relates to an isolated microorganism selected from strains:
1) *Paenibacillus* strain Lu16774 deposited with DSMZ under Accession No. DSM 26969,
2) *Paenibacillus* strain Lu17007 deposited with DSMZ under Accession No. DSM 26970, and
3) *Paenibacillus* strain Lu17015 deposited with DSMZ under Accession No. DSM 26971; showing antagonistic activity against at least one plant pathogen, and being capable of producing at least one fusaricidin-type compound; or a mutant strain thereof retaining said capability, i.e. retaining said antagonistic activity against at least one plant pathogen, and retaining said capability of producing at least one fusaricidin-type compound.

A further embodiment relates to a microorganism selected from:
1) *Paenibacillus* strain Lu16774 deposited with DSMZ under Accession No. DSM 26969,
2) *Paenibacillus* strain Lu17007 deposited with DSMZ under Accession No. DSM 26970, and
3) *Paenibacillus* strain Lu17015 deposited with DSMZ under Accession No. DSM 26971; or a mutant strain thereof having all the identifying characteristics of one of said strains.

An identifying characteristic of the deposited *Paenibacillus* strains Lu16774, Lu17007 and Lu17015 is that they are capable of producing at least one compound of formula I, preferably selected from compounds 1A and 1 B, in particular producing compounds 1A and 1 B, which are metabolites of the respective strains; and the agriculturally acceptable salts thereof.

Thus, according to one aspect of the invention, *Paenibacillus* strains of the invention are capable of producing at least one compound of formula I, more preferably producing compounds 1A or 1 B, in particular producing compounds 1A and 1 B; and the agriculturally acceptable salts thereof.

Thus, according to one aspect of the invention, *Paenibacillus* strains of the invention are capable of producing at least one compound of formula I, more preferably producing compounds 1A or 1 B, in particular producing compounds 1A and 1 B; and the agriculturally acceptable salts thereof, in a growth medium comprising at least one source of carbon and one source of nitrogen as defined herein.

Thus, according to one aspect of the invention, *Paenibacillus* strains of the invention in a growth medium comprising at least one source of carbon and one source of nitrogen as defined herein produce at least one compound of formula I, more preferably produce compounds 1A or 1 B, in particular produce compounds 1A and 1 B; and the agriculturally acceptable salts thereof.

Another embodiment of the invention relates to an isolated microorganism selected from
1) *Paenibacillus* strain Lu16774 deposited with DSMZ under Accession No. DSM 26969,
2) *Paenibacillus* strain Lu17007 deposited with DSMZ under Accession No. DSM 26970, and
3) *Paenibacillus* strain Lu17015 deposited with DSMZ under Accession No. DSM 26971; showing antagonistic activity against at least one plant pathogen, and being capable of producing at least one fusaricidin-type compound of formula I, preferably selected from compounds 1A and 1 B, in particular producing compounds 1A and 1 B; or a mutant strain thereof retaining said capability, i.e. retaining said antagonistic activity against at least one plant pathogen, and retaining said capability of producing at least one fusaricidin-type compound of formula I, preferably selected from compounds 1A and 1 B, in particular producing compounds 1A and 1 B.

Another embodiment of the invention relates to an isolated microorganism selected from
1) *Paenibacillus* strain Lu16774 deposited with DSMZ under Accession No. DSM 26969,
2) *Paenibacillus* strain Lu17007 deposited with DSMZ under Accession No. DSM 26970, and
3) *Paenibacillus* strain Lu17015 deposited with DSMZ under Accession No. DSM 26971; showing antagonistic activity against at least one plant pathogen, and being in a growth medium comprising at least one source of carbon and one source of nitrogen as defined herein capable of producing at least one fusaricidin-type compound of formula I, preferably selected from compounds 1A and 1B, in particular producing compounds 1A and 1B; or a mutant strain thereof retaining said capability, i.e. retaining said antagonistic activity against at least one plant pathogen, and retaining said capability of producing at least one fusaricidin-type compound of formula I, preferably selected from compounds 1A and 1B, in particular producing compounds 1A and 1 B.

Another embodiment of the invention relates to an isolated microorganism selected from
1) *Paenibacillus* strain Lu16774 deposited with DSMZ under Accession No. DSM 26969,
2) *Paenibacillus* strain Lu17007 deposited with DSMZ under Accession No. DSM 26970, and
3) *Paenibacillus* strain Lu17015 deposited with DSMZ under Accession No. DSM 26971; showing antagonistic activity against at least one plant pathogen, and producing at least one fusaricidin-type compound of formula I, preferably selected from compounds 1A and 1B, in particular producing compounds 1A and 1 B; or a mutant strain thereof retaining said capability, i.e. retaining said antagonistic activity against at least one plant pathogen, and retaining said capability of producing at least one fusaricidin-type compound of formula I, preferably selected from compounds 1A and 1 B, in particular producing compounds 1A and 1 B.

A further identifying characteristic of the deposited *Paenibacillus* strains Lu16774, Lu17007 and Lu17015 or a mutant strain thereof is that they are capable of producing at least one compound selected from the group consisting of fusaricidin A, fusaricidin B, fusaricidin C, fusaricidin D, LI-F06a, LI-F06b and LI-F08b in addition to their capability of producing at least one compound of formula I, preferably selected from compounds 1A and 1B, in particular producing compounds 1A and 1B.

Thus, according to a further aspect of the invention, *Paenibacillus* strains of the invention are capable of producing at least one fusaricidin of formula I, preferably selected from compounds 1A and 1 B, in particular producing compounds 1A and 1 B, as disclosed herein, and are capable of producing at least one compound selected from the group consisting of fusaricidin A, fusaricidin B, fusaricidin C, fusaricidin D, LI-F06a, LI-F06b and LI-F08b.

According to a further aspect of the invention, *Paenibacillus* strains of the invention are capable of producing at least one fusaricidin of formula I, preferably selected from compounds 1A and 1 B, in particular producing compounds 1A and 1 B, as disclosed herein, and are capable of producing at least three compounds selected from the group consisting of fusaricidin A, fusaricidin B, fusaricidin C, fusaricidin D, LI-F06a, LI-F06b and LI-F08b.

According to a further aspect of the invention, *Paenibacillus* strains of the invention are capable of producing at least one fusaricidin of formula I, preferably selected from compounds 1A and 1B, in particular producing compounds 1A and 1B, as disclosed herein, and are capable of producing at least five compounds selected from the group consisting of fusaricidin A, fusaricidin B, fusaricidin C, fusaricidin D, LI-F06a, LI-F06b and LI-F08b.

According to a further aspect of the invention, *Paenibacillus* strains of the invention are capable of producing at least one fusaricidin of formula I, preferably selected from compounds 1A and 1B, in particular producing compounds 1A and 1B, as disclosed herein, and are capable of producing fusaricidin A, fusaricidin B, fusaricidin C, fusaricidin D and LI-F08b.

A further identifying characteristic of the deposited *Paenibacillus* strains are their antifungal activity. In particular, these strains were found to be effective against infestation with plant pathogens including *Alternaria* spp., *Botrytis cinerea*, *Phytophthora infestans*, and *Sclerotina sclerotiorum*; wherein *Alternaria* spp. is preferably selected from *A. solani* and *A. alternata*, in particular *A. solani*.

Thus, according to a further aspect of the invention, *Paenibacillus* strains of the invention have antifungal activity, particularly against a plant pathogen selected from the group consisting of *Alternaria* spp., *Botrytis cinerea*, *Phytophthora infestans*, and *Sclerotinia sclerotiorum*, wherein *Alternaria* spp. is preferably selected from *A. solani* and *A. alternata*, in particular *A. solani* More particularly, *Paenibacillus* strains of the invention have antifungal activity against at least two or against all four of said pathogens.

According to a further aspect of the invention, *Paenibacillus* strains of the invention have antifungal activity against the plant pathogens *Alternaria solani*, *Botrytis cinerea*, *Phytophthora infestans*, and *Sclerotinia sclerotiorum*.

Antagonistic activity of the *Paenibacillus* strains against plant pathogens can be shown in an in-vitro confrontation assays using the desired phytopathogenic fungi such as *Alternaria* spp., *Botrytis cinerea*, *Phytophthora infestans*, and *Sclerotinia sclerotiorum* wherein *Alternaria* spp. is preferably selected from *A. solani* and *A. alternata*, in particular *A. solani*:

As growth medium for these phytopathogenic fungi, ISP2 medium is used comprising per litre: 10 g malt extract (Sigma Aldrich, 70167); 4 g Bacto yeast extract (Becton Dickinson, 212750); 4 g glucose monohydrate (Sigma Aldrich, 16301); 20 g Agar (Becton Dickinson, 214510), pH about 7, Aq. bidest. As growth medium for PHYTIN, V8 medium is used comprising per litre: 200 ml of vegetable juice, 3 g calcium carbonate (Merck Millipore, 1020660250); 30 g Agar (Becton Dickinson, 214510), pH 6.8, Aq. bidest.

The *Paenibacillus* strains are point-inoculated on one side of an agar plate. An agar block (approx. 0.3 cm$^2$) containing one actively growing plant pathogen was put in the center of the plate. After incubating for 7-14 days at about 25° C., the growth of the plant pathogen is examined, especially for inhibition zones. The following antagonistic effects can be evaluated: Antibiosis is scored by evaluation of the diameter of the fungi-free zone (zone of inhibition). Competition is scored by comparing the diameter of the growth of the fungal pathogen on plates with bacterial strains in comparison to control plates. Mycoparasitism can be documented in case the bacteria overgrows the fungal pathogen and also mycoparasite the pathogens. This can be visualized by microscopy.

Another identifying characteristic of the deposited *Paenibacillus* strains Lu16774, Lu17007 and Lu17015 is that they are capable of producing and secreting at least one lytic enzyme preferably selected from chitinase, cellulase and amylase (see Example 6), even more preferably at least chitinase and cellulose; in particular in a growth medium comprising at least one source of carbon and one source of nitrogen as defined herein.

Thus, according to a further aspect of the invention, *Paenibacillus* strains of the invention are capable of producing and secreting at least one lytic enzyme preferably selected from chitinase, cellulase and amylase, even more preferably at least chitinase and cellulose; in particular in a growth medium comprising at least one source of carbon and one source of nitrogen as defined herein.

More specifically, the present invention relates to the deposited strains Lu16774, Lu17007 and Lu17015 and any *Paenibacillus* strain having one or more of the identifying characteristics of the deposited strain, wherein the identifying characteristics are selected from the group consisting of:
  (a) antifungal activity against a plant pathogen selected from the group consisting of *Alternaria* spp., *Botrytis cinerea*, *Phytophthora infestans*, and *Sclerotinia sclerotiorum*, wherein *Alternaria* spp. is preferably selected from *A. solani* and *A. alternata*, in particular *A. solani*, as disclosed herein;
  (b) the capability of producing at least one fusaricidin-type compound of formula I, in particular compounds 1A and/or 1 B, as disclosed herein;
  (c) the capability of producing at least one compound selected from the group consisting of fusaricidins A, B, C, D, LI-F06a, LI-F06b and LI-F08b, as disclosed herein; and
  (d) the capability of producing and secreting at least one lytic enzyme selected from the group consisting of chitinase, cellulose and amylase, as disclosed herein.

More preferably, said *Paenibacillus* strain has the capabilities referred to as (b), (c) and (d) in a growth medium comprising at least one source of carbon and one source of nitrogen as defined herein.

In particular, *Paenibacillus* strains of the invention have two or more of the identifying characteristics of the deposited strain, with strains having at least the characteristics (a) and (b) being particularly preferred. For instance, according to a preferred embodiment, the strains of the invention (a) have an antifungal activity against a plant pathogen selected from the group consisting of *Alternaria* spp., *Botrytis cinerea*, *Phytophthora infestans*, and *Sclerotinia sclerotiorum*, wherein *Alternaria* spp. is preferably selected from *A. solani* and *A. alternata*, in particular *A. solani* and (b) are capable of producing at least one compound of formula I, and particularly compound 1 B. According to a further preferred embodiment, the strains of the invention (a) have an antifungal activity against three or against all of the plant pathogens selected from the group consisting of *Alternaria* spp., *Botrytis cinerea*, *Phytophthora infestans*, and *Sclerotinia sclerotiorum*, wherein *Alternaria* spp. is preferably selected from *A. solani* and *A. alternata*, in particular *A. solani* and (b) are capable of producing at least one compound of formula I, more preferably producing compounds 1A or 1 B, in particular of producing compounds 1A and 1 B.

According to an embodiment of the invention, the strains of the invention are provided in isolated or substantially purified form.

The terms "isolated" or "substantially purified" are meant to denote that the strains of the invention have been removed from a natural environment and have been isolated or separated, and are at least 60% free, preferably at least 75% free, and more preferably at least 90% free, even more preferably at least 95% free, and most preferably at least 99% free from other components with which they were naturally associated. An isolate obtained by culturing a single microbial colony is an example of an isolated strain of the invention.

The strains of the invention may be provided in any physiological state such as active or dormant. Dormant strains may be provided for example frozen, dried, or lyophilized or partly desiccated (procedures to produce partly desiccated organisms are given in WO 2008/002371) or in form of spores.

According to an embodiment of the invention, the strains of the invention are provided in the form of spores.

According to a further embodiment of the invention, the strains of the invention are provided as a whole culture broth comprising a strain of the invention.

The culture is preferably an isolated or substantially purified culture.

An "isolated culture" or "substantially purified culture" refers to a culture of the strains of the invention that does not include significant amounts of other materials which normally are found in natural habitat in which the strain grows and/or from which the strain normally may be obtained. Consequently, such "isolated culture" or "substantially purified culture" is at least 60% free, preferably at least 75% free, and more preferably at least 90% free, even more preferably at least 95% free, and most preferably at least 99% free from other materials which normally are found in natural habitat in which the strain grows and/or from which the strain normally may be obtained. Such an "isolated culture" or "substantially purified culture" does normally not include any other microorganism in quantities sufficient to interfere with the replication of the strain of the invention. Isolated cultures of the invention may, however, be combined to prepare a mixed culture of the strains of the invention and a further biopesticide, preferably a microbial pesticide.

The invention relates to methods for the fermentative production of antipathogenic biopesticides as described herein.

The strains as used according to the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The medium that is to be used for cultivation of the microorganism must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981).

These media that can be used according to the invention generally comprise one or more sources of carbon, sources of nitrogen, inorganic salts, vitamins and/or trace elements. Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid. Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture. Inorganic salt compounds that may be present in the media comprise the chloride, phosphate or sulfate salts of calcium, magnesium, sodium, cobalt, molybdenum, potassium, manganese, zinc, copper and iron. Inorganic sulfur-containing compounds, for example sulfates, sulfites, dithionites, tetrathionates, thiosulfates, sulfides, but also organic sulfur compounds, such as mercaptans and thiols, can be used as sources of sulfur. Phosphoric acid, potassium dihydrogenphosphate or dipotassium hydrogenphosphate or the corresponding sodium-containing salts can be used as sources of phosphorus. Chelating agents can be added to the medium, in order to keep the metal ions in solution. Especially suitable chelating agents comprise dihydroxyphenols, such as catechol or protocatechuate, or organic acids, such as citric acid. The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc.

Preferred growth media that can be used according to the invention comprise one or more sources of carbon selected from L-arabinose, N-acetyl-D-glucosamine, D-galactose, L-aspartaic acid, D-trehalose, D-mannose, glycerol, D-gluconic acid, D-xylose, D-mannitol, D-ribose, D-fructose, α-D-glucose, maltose, D-melibiose, thymidine, α-methyl-D-Galactoside, α-D-lactose, lactulose, sucrose, uridine, α-hydroxy glutaric acid-γ-lactone, β-methyl-D-glucoside, adonitol, maltotriose, 2-deoxyadenosine, adenosine, citric acid, mucic acid, D-cellobiose, inosine, L-serine, L-alanyl-glycine, D-galacturonic acid, α-cyclodextrin, β-cyclodextrin, dextrin, inulin, pectin, amygdalin, gentiobiose, lactitol, D-melezitose, α-methyl-D-glucoside, β-methyl-D-galactoside, β-methyl-D-xyloside, palatinose, D-raffinose, stachyose, turanose, γ-amino butyric acid, D-gluosamine, D-lactic acid, L-lysine, 3-hydroxy 2-butanone; and one or more sources of nitrogen selected from ammonia, nitrite, nitrate, L-alaninie, L-asparagine, L-aspartic acid, L-glutamic acid, L-glutamie, glycine, aminoacid dimes: Ala-Asp, AlaGln, Ala-Glu, Ala-His, Gly-Gln, Gly-Glu, Gly-Met, and Met-Ala; in particular nitrate. These media can be supplemented with inorganic salts and vitamins and/or trace elements. The strains are capable to produce compounds 1A and 1B in these growth media.

All components of the medium are sterilized, either by heating (20 min at 2.0 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 36° C., preferably 25° C. to 33° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e. g. fatty acid polyglycol esters, can be used for controlling foaming. To maintain the stability of plasmids, suitable substances with selective action, e. g. antibiotics, can be added to the medium. Oxygen or oxygen-containing gas mixtures, e. g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours.

In particular, the strains of the invention may be cultivated in a medium a variety of standard microbiology media such as Luria-Bertani Broth (LB), trypticase-soy broth (TSB), yeast extract/malt extract/glucose broth (YMG, ISP2) at 15° C. to 36° C. for 18 to 360 h in liquid media or in agar-solidified media on a petri dish. Aeration may be necessary. The bacterial cells (vegetative cells and spores) can be washed and concentrated (e. g. by centrifugation at temperatures of about 15 to 30° C. for about 15 min at 7,000×g).

The invention also relates to culture medium obtainable by culturing the strains of the invention in a medium and separating the medium from the culture broth (thus, remaining when cells grown in the medium are removed from the whole culture broth), e. g., the supernatant of a whole culture broth, i.e., the liquid broth remaining when cells grown in broth and other debris are removed by centrifugation, filtration, sedimentation, or other means well known in the art. The supernatant can be obtained e. g. by centrifugation at temperatures of about 2 to 30° C. (more preferably at temperatures of 4 to 20° C.) for about 10 to 60 min (more preferably about 15 to 30 min) at about 5,000 to 20,000×g (more preferably at about 15,000×g).

Such culture medium contains pesticidal metabolites which are produced by the cultured strain.

The invention also relates to cell-free extracts of the strains of the invention. To produce a cell-free extract, the strains of the invention may be cultivated as described above. The cells can be disrupted also by high-frequency ultrasound, by high pressure, e. g. in a French pres-pressure cell, by osmolysis, by the action of detergents, lytic enzymes or organic solvents, by means of homogenizers or by a combination of several of the methods listed. The extraction can be carried out preferably with an organic solvent or solvent mixture, more preferably an alcohol (e. g. methanol, ethanol, n-propanol, 2-propanol or alike), even more preferably with 2-propanol (e. g. in a 1:1 ratio to the culture volume). Phase separation may be enhanced by addition of salts such as NaCl. The organic phase can be collected and the solvent or solvent mixture may be removed by conventional distillation and/or drying followed by resuspension in methanol and filtration.

Such extract contains pesticidal metabolites which are produced by the cultured strain.

Pesticidal metabolites that are specific to the strains of the invention may be recovered from such medium or extract according to conventional methods in particular when the strains of the invention have been cultivated as described above.

The methodology of the present invention can further include a step of recovering individual pesticidal metabolites.

The term "recovering" includes extracting, harvesting, isolating or purifying the compound from culture media or cell-free extracts. Recovering the compound can be performed according to any conventional isolation or purification methodology known in the art including, but not limited to, treatment with a conventional resin (e. g., anion or cation exchange resin, non-ionic adsorption resin, etc.), treatment with a conventional adsorbent (e. g., activated charcoal, silicic acid, silica gel, cellulose, alumina, etc.), alteration of pH, solvent extraction (e. g., with a conventional solvent such as an alcohol, ethyl acetate, hexane and the like), distillation, dialysis, filtration, concentration, crystallization, recrystallization, pH adjustment, lyophilization and the like. For example the metabolites can be recovered from culture media by first removing the microorganisms. The remaining broth is then passed through or over a cation exchange resin to remove unwanted cations and then through or over an anion exchange resin to remove unwanted inorganic anions and organic acids.

Several metabolites have been found in whole culture broth of the novel *Paenibacillus* strains. Nine metabolites have been studied in detail and identified (see Example 7, FIG. 1). Two of them were found to be novel (compound 1A and compound 1 B). Compounds 1A and 1 B have been found to be produced by all three *Paenibacillus* strains of the invention (see Table 17) but none of them was found in the whole culture broth of the related *Paenibacillus peoriae* strain NRRL BD-62.

Thus the present invention also relates to compounds of formula I

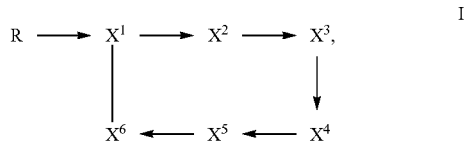

wherein
R is selected from 15-guanidino-3-hydroxypentadecanoic acid (GHPD) and 12-guanidinododecanoic acid (12-GDA);
$X^1$ is threonine;
$X^2$ is isoleucine;
$X^3$ is tyrosine;
$X^4$ is threonine;

$X^5$ is selected from glutamine and asparagine;
$X^6$ is alanine; and
wherein an arrow defines a single (amide) bond either between the carbonyl moiety of R and the amino group of the amino acid $X^1$ or between the carbonyl group of one amino acid and the amino group of a neighboring amino acid wherein the tip of the arrow indicates the attachment to the amino group of said neighboring amino acid; and wherein the single line (without an arrow head) defines a single (ester) bond between the carbonyl group of $X^6$ and the hydroxyl group of $X^1$;
and the agriculturally acceptable salts thereof.

According to a further embodiment, $X^1$ in formula I is preferably L-threonine.

According to a further embodiment, $X^2$ in formula I is preferably D-isoleucine or D-allo-isoleucine.

According to a further embodiment, $X^3$ in formula I is preferably L-tyrosine.

According to a further embodiment, $X^4$ in formula I is preferably D-allo-threonine.

According to a further embodiment, $X^5$ in formula I is preferably D-glutamine or D-asparagine.

According to a further embodiment, R in formula I is preferably GHPD.

The sketch of formula I for compounds of formula I may also be depicted as follows:

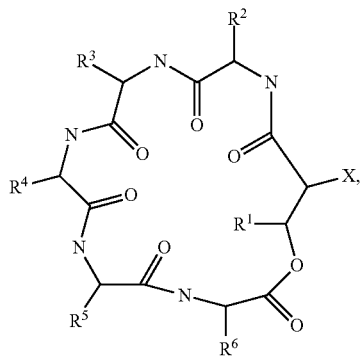

wherein
X is selected from —NH—(C=O)—CH$_2$—CH(OH)—(CH$_2$)$_{12}$—NH—C(=NH)NH$_2$ and —NH—(C=O)—(CH$_2$)$_{11}$—NH—C(=NH)NH$_2$;
$R^1$ is 1-hydroxyethyl;
$R^2$ is 1-methylpropyl (sec-butyl);
$R^3$ is 4-hydroxybenzyl;
$R^4$ is 1-hydroxyethyl;
$R^5$ is selected from carbamoylethyl and carbamoylmethyl;
$R^6$ is methyl.

Likewise, the preferred embodiments based on this alternative sketch of formula I
are as follows:
$R^1$ in this formula I is preferably (1 S,2R)-1-hydroxyethyl.
$R^2$ in this formula I is preferably (1R,2R)-1-methylpropyl or (1R,2S)-1-methylpropyl.
$R^3$ in this formula I is preferably (S)-4-hydroxy-benzyl.
$R^4$ in this formula I is preferably (1 S,2R)-1-hydroxyethyl.
$R^5$ in this formula I is preferably (R)-carbamoylethyl and (R)-carbamoylmethyl.
X in this formula I is preferably —NH—(C=O)—CH$_2$—CH(OH)—(CH$_2$)$_{12}$—NH—C(=NH)NH$_2$.

According to a further embodiment, the invention further relates to compounds 1A and 1B, which are of formula I, wherein R is GHPD and wherein $X^4$ is asparagine in case of compound 1A and $X^4$ is glutamine in case of compound 1B:

Compound 1A

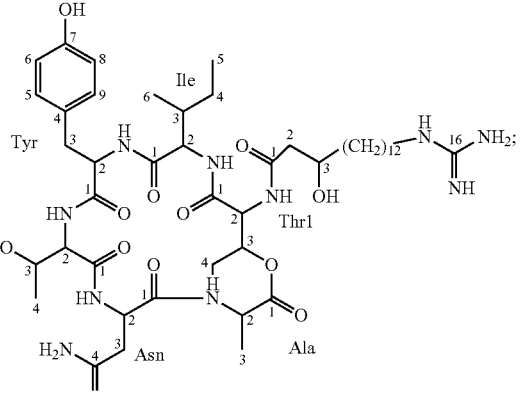

Compound 1B

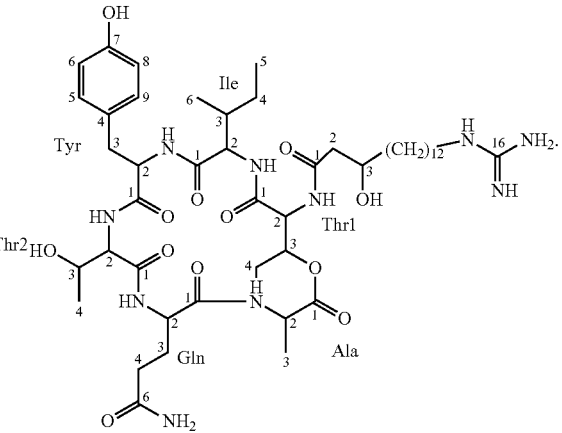

The pesticidal metabolites from the strains of the invention are preferably selected from compounds of formula I wherein R is GHPD, in particular selected from compounds 1A and 1 B, which can be obtained by extraction and isolation from cultures, i.e. whole culture broths, of the strains of the invention.

Further, the fusaricidin-type compounds of formula I including those wherein R is GHTD can be synthesized in analogy to methods known in the art (Biopolymers 80(4), 541, 2005; J. Peptide Sci. 12S, 219, 2006; Tetrahedron Lett. 47(48), 8587-90, 2006; Biopolymers 88(4), 568, 2007; ChemMedChem 7, 871-882, 2012).

The invention also relates to the agriculturally acceptable salts, particularly acid addition salts of said fusaricidin-type compounds of formula I. Said salts can be obtained by conventional methods well known in the art, e. g. by reacting the compounds of the invention with a suitable acid to form an acid addition salt. Anions of useful acid addition salts are primarily chloride, bromide, fluoride, iodide, hydrogensulfate, methylsulfate, sulfate, dihydrogenphosphate, hydrogen-phosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Consequently, the invention also relates to a whole culture broth of a microorganism comprising at least one compound of formula I or an agriculturally acceptable salt thereof, preferably selected from compounds 1A and 1B or an agriculturally acceptable salt thereof, in particular said whole culture broth comprises compounds 1A and 1B or an agriculturally acceptable salt thereof.

According to a further embodiment, the invention also relates to a whole culture broth of a microorganism of the genus *Paenibacillus* comprising at least one compound of formula I or an agriculturally acceptable salt thereof, preferably selected from compounds 1A and 1B or an agriculturally acceptable salt thereof, in particular said whole culture broth comprises compounds 1A and 1B or an agriculturally acceptable salt thereof.

According to a further embodiment, the invention also relates to a whole culture broth of at least one *Paenibacillus* strain of the invention as identified and defined above comprising at least one compound of formula I or an agriculturally acceptable salt thereof, preferably selected from compounds 1A and 1B or an agriculturally acceptable salt thereof, in particular said whole culture broth comprises compounds 1A and 1B or an agriculturally acceptable salt thereof.

Said fusaricidin-type compounds are secreted into the culture medium of the respective microorganism capable of producing it.

Consequently, the invention also relates to a culture medium and/or a cell-free extract of a microorganism comprising at least one compound of formula I or an agriculturally acceptable salt thereof, preferably selected from compounds 1A and 1B or an agriculturally acceptable salt thereof, in particular said culture medium and/or a cell-free extract comprises compounds 1A and 1B or an agriculturally acceptable salt thereof.

According to a further embodiment, the invention also relates to a culture medium and/or a cell-free extract of a microorganism of the genus *Paenibacillus* comprising at least one compound of formula I or an agriculturally acceptable salt thereof, preferably selected from compounds 1A and 1B or an agriculturally acceptable salt thereof, in particular said culture medium and/or a cell-free extract comprises compounds 1A and 1B or an agriculturally acceptable salt thereof.

According to a further embodiment, the invention also relates to culture medium and/or a cell-free extract of at least one *Paenibacillus* strain of the invention as identified and defined above comprising at least one compound of formula I or an agriculturally acceptable salt thereof, preferably selected from compounds 1A and 1B or an agriculturally acceptable salt thereof, in particular said culture medium and/or a cell-free extract comprises compounds 1A and 1B or an agriculturally acceptable salt thereof.

The invention further relates to agrochemical compositions comprising an auxiliary as defined below and at least one or more of the strains, whole culture broths, cell-free extracts, culture media and compounds of formula I, of the invention, respectively.

As used herein, "composition" in reference to a product (microbial strain, agent or formulation) of the present invention refers to a combination of ingredients, wherein "formulating" is the process of using a formula, such as a recipe, for a combination of ingredients, to be added to form the formulation. Such composition is also referred herein to as formulation.

The strains, whole culture broths, cell-free extracts, culture media, compounds of formula I, and compositions of the invention, respectively, are suitable as antifungal agents or fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The strains, whole culture broths, cell-free extracts, culture media, compounds of formula I, and compositions of the invention, respectively, are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e. g. conifers; and on the plant propagation material, such as seeds, and the crop material of these plants.

Preferably, the strains, whole culture broths, cell-free extracts culture media, compounds of formula I; and compositions of the invention, respectively, are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with the strains, whole culture broths, cell-free extracts culture media, compounds of formula I; and compositions of the invention, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacte-bacterial genus *Bacillus*, particularly from *Bacillus thuringiensis*, such as δ-endotoxins, e. g. CryIA(b), CryIA (c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The strains, whole culture broths, cell-free extracts, culture media, compounds of formula I, and compositions of the invention, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossy-gossypii*), corn (e. g. *C. graminicola*:Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*. Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. taxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria* blotch) on wheat or *M. fijiens* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meiborniae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Phy-Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans* late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici*(*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *ThielaviopsiS* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Usti-Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The strains, whole culture broths, cell-free extracts, culture media, compounds of formula I, and compositions of the invention, respectively, are also suitable for controlling harmful pathogens, especially fungi, in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisiae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The strains, whole culture broths, cell-free extracts, culture media, compounds of formula I, and compositions of the invention, respectively, may be used for improving the health of a plant. The invention also relates to a method for improving plant health by treating a plant, its propagation material and/or the locus where the plant is growing or is to grow with an effective amount of the strains, whole culture broths, cell-free extracts, culture media, compounds of formula I, and compositions.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

Healthier plants are desirable since they result among others in better yields and/or a better quality of the plants or crops, specifically better quality of the harvested plant parts. Healthier plants also better resist to biotic and/or abiotic stress. A high resistance against biotic stresses in turn allows the person skilled in the art to reduce the quantity of pesticides applied and consequently to slow down the development of resistances against the respective pesticides.

It has to be emphasized that the above mentioned effects of the strains, whole culture broths, cell-free extracts, culture media, compounds of formula I, and compositions of the invention, respectively, i.e. enhanced health of the plant, are also present when the plant is not under biotic stress and in particular when the plant is not under pest pressure.

For example, for seed treatment and soil applications, it is evident that a plant suffering from fungal or insecticidal attack shows reduced germination and emergence leading to poorer plant or crop establishment and vigor, and consequently, to a reduced yield as compared to a plant propagation material which has been subjected to curative or preventive treatment against the relevant pest and which can grow without the damage caused by the biotic stress factor. However, the methods according to the invention lead to an enhanced plant health even in the absence of any biotic stress. This means that the positive effects of the strains, whole culture broths, cell-free extracts, culture media, compounds of formula I, and compositions of the invention, respectively, cannot be explained just by the pesticidal activities of strains, whole culture broths, cell-free extracts, culture media, compounds of formula I, and compositions of the invention, respectively, but are based on further activity profiles. Accordingly, the application of the strains, whole culture broths, cell-free extracts, culture media, compounds of formula I, and compositions of the invention, respectively, can also be carried out in the absence of pest pressure.

In an equally preferred embodiment, the present invention relates to a method for improving the health of plants grown from said plant propagation material, wherein the plant propagation material is treated with an effective amount of at least one strains, whole culture broths, cell-free extract, culture medium, compound of formula I, or a composition of the invention.

Each plant health indicator listed below, which is selected from the groups consisting of yield, plant vigor, quality and tolerance of the plant to abiotic and/or biotic stress, is to be understood as a preferred embodiment of the present invention either each on its own or preferably in combination with each other.

According to the present invention, "increased yield" of a plant means that the yield of a product of the respective plant is increased by a measurable amount over the yield of the same product of the plant produced under the same conditions, but without the application of the strains, whole culture broths, cell-free extracts, culture media, compounds of formula I, and compositions of the invention, respectively.

For seed treatment e. g. as inoculant and/or foliar application forms, increased yield can be characterized, among others, by the following improved properties of the plant: increased plant weight; and/or increased plant height; and/or increased biomass such as higher overall fresh weight (FW); and/or increased number of flowers per plant; and/or higher grain and/or fruit yield; and/or more tillers or side shoots (branches); and/or larger leaves; and/or increased shoot growth; and/or increased protein content; and/or increased oil content; and/or increased starch content; and/or increased pigment content; and/or increased chlorophyll content (chlorophyll content has a positive correlation with the plant's photosynthesis rate and accordingly, the higher the chlorophyll content the higher the yield of a plant) and/or increased quality of a plant.

"Grain" and "fruit" are to be understood as any plant product which is further utilized after harvesting, e. g. fruits in the proper sense, vegetables, nuts, grains, seeds, wood (e. g. in the case of silviculture plants), flowers (e. g. in the case of gardening plants, ornamentals) etc., that is anything of economic value that is produced by the plant.

According to the present invention, the yield is increased by at least 4%. In general, the yield increase may even be higher, for example 5 to 10%, more preferable by 10 to 20%, or even 20 to 30%

According to the present invention, the yield—if measured in the absence of pest pressure—is increased by at least 2% In general, the yield increase may even be higher, for example until 4% to 5% or even more.

Another indicator for the condition of the plant is the plant vigor. The plant vigor becomes manifest in several aspects such as the general visual appearance.

For foliar applications, improved plant vigor can be characterized, among others, by the following improved properties of the plant: improved vitality of the plant; and/or improved plant growth; and/or improved plant development; and/or improved visual appearance; and/or improved plant stand (less plant verse/lodging and/or bigger leaf blade; and/or bigger size; and/or increased plant height; and/or increased tiller number; and/or increased number of side shoots; and/or increased number of flowers per plant; and/or increased shoot growth; and/or enhanced photosynthetic activity (e. g. based on increased stomatal conductance and/or increased $CO_2$ assimilation rate)); and/or earlier flowering; and/or earlier fruiting; and/or earlier grain maturity; and/or less non-productive tillers; and/or less dead basal leaves; and/or less input needed (such as fertilizers or water); and/or greener leaves; and/or complete maturation under shortened vegetation periods; and/or easier harvesting; and/or faster and more uniform ripening; and/or longer shelf-life; and/or longer panicles; and/or delay of senescence; and/or stronger and/or more productive tillers; and/or better extractability of ingredients; and/or improved quality of seeds (for being seeded in the following seasons for seed production); and/or reduced production of ethylene and/or the inhibition of its reception by the plant.

Another indicator for the condition of the plant is the "quality" of a plant and/or its products. According to the present invention, enhanced quality means that certain plant characteristics such as the content or composition of certain ingredients are increased or improved by a measurable or noticeable amount over the same factor of the plant produced under the same conditions, but without the application of the strains, whole culture broths, cell-free extracts, culture media, compounds of formula I, and compositions of the invention, respectively. Enhanced quality can be characterized, among others, by following improved properties of the plant or its product: increased nutrient content; and/or increased protein content; and/or in-increased oil content; and/or increased starch content; and/or increased content of fatty acids; and/or increased metabolite content; and/or increased carotenoid content; and/or increased sugar content; and/or increased amount of essential amino acids; and/or improved nutrient composition; and/or improved protein composition; and/or improved composition of fatty acids; and/or improved metabolite composition; and/or improved carotenoid composition; and/or improved sugar composition; and/or improved amino acids composition; and/or improved or optimal fruit color; and/or improved leaf color; and/or higher storage capacity; and/or better processability of the harvested products.

Another indicator for the condition of the plant is the plants tolerance or resistance to biotic and/or abiotic stress factors. Biotic and abiotic stress, especially over longer terms, can have harmful effects on plants.

Biotic stress is caused by living organisms while abiotic stress is caused for example by environmental extremes. According to the present invention, "enhanced tolerance or resistance to biotic and/or abiotic stress factors" means (1.) that certain negative factors caused by biotic and/or abiotic stress are diminished in a measurable or noticeable amount as compared to plants exposed to the same conditions, but without being treated with the strains, whole culture broths, cell-free extracts, culture media, compounds of formula I, and compositions of the invention, respectively, and (2.) that the negative effects are not diminished by a direct action of the strains, whole culture broths, cell-free extracts, culture media, compounds of formula I, and compositions of the invention, respectively, on the stress factors, e. g. by its fungicidal or insecticidal action which directly destroys the microorganisms or pests, but rather by a stimulation of the plants' own defensive reactions against said stress factors.

Negative factors caused by biotic stress such as pathogens and pests are widely known and are caused by living organisms, such as competing plants (for example weeds), microorganisms (such as phytopathogenic fungi and/or bacteria) and/or viruses.

Negative factors caused by abiotic stress are also well-known and can often be observed as reduced plant vigor (see above), for example:

less yield and/or less vigor, for both effects examples can be burned leaves, less flowers, pre-mature ripening, later crop maturity, reduced nutritional value amongst others.

Abiotic stress can be caused for example by: extremes in temperature such as heat or cold (heat stress/cold stress); and/or strong variations in temperature; and/or temperatures unusual for the specific season; and/or drought (drought stress); and/or extreme wetness; and/or high salinity (salt stress); and/or radiation (for example by increased UV radiation due to the decreasing ozone layer); and/or increased ozone levels (ozone stress); and/or organic pollution (for example by phytotoxic amounts of pesticides); and/or inorganic pollution (for example by heavy metal contaminants).

As a result of biotic and/or abiotic stress factors, the quantity and the quality of the stressed plants decrease. As far as quality (as defined above) is concerned, reproductive development is usually severely affected with consequences on the crops which are important for fruits or seeds. Synthesis, accumulation and storage of proteins are mostly affected by temperature; growth is slowed by almost all types of stress; polysaccharide synthesis, both structural and storage is reduced or modified: these effects result in a decrease in biomass (yield) and in changes in the nutritional value of the product.

As pointed out above, the above identified indicators for the health condition of a plant may be interdependent and may result from each other. For example, an increased resistance to biotic and/or abiotic stress may lead to a better plant vigor, e. g. to better and bigger crops, and thus to an increased yield. Inversely, a more developed root system may result in an increased resistance to biotic and/or abiotic stress. However, these interdependencies and interactions are neither all known nor fully understood and therefore the different indicators are described separately.

In one embodiment the strains, whole culture broths, cell-free extracts, culture media, compounds of formula I, and compositions of the invention, respectively, effectuate an increased yield of a plant or its product. In another embodiment the strains, whole culture broths, cell-free extracts, culture media, compounds of formula I, and compositions of the invention, respectively, effectuate an increased vigor of a plant or its product. In another embodiment the strains, whole culture broths, cell-free extracts, culture media, compounds of formula I, and compositions of the invention, respectively, effectuate in an increased quality of a plant or its product. In yet another embodiment the strains, whole culture broths, cell-free extracts, culture media, compounds of formula I, and compositions of the invention, respectively, effectuate an increased tolerance and/or resistance of a plant or its product against biotic stress. In yet another embodiment the strains, whole culture broths, cell-free extracts, culture media, compounds of formula I, and compositions of the invention, respectively, effectuate an increased tolerance and/or resistance of a plant or its product against abiotic stress.

The strains, whole culture broths, cell-free extracts, culture media and compounds of formula I, respectively, are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

The term "effective amount" denotes an amount which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the strains, whole culture broths, cell-free extracts, culture media and compounds of formula I or salt thereof, of the invention, respectively, used.

Plant propagation materials may be treated with the strains, whole culture broths, cell-free extracts, culture media, compounds of formula I, and compositions of the invention, respectively, prophylactically either at or before planting or transplanting.

The strains of the invention can be formulated as an inoculant for a plant. The term "inoculant" means a composition that includes an isolated strain of the invention and optionally a carrier, which may include a biologically acceptable medium.

Such inoculants and other suitable compositions can be prepared as compositions comprising besides the active ingredients at least one auxiliary (inert ingredient) by usual means (see e. g. H. D. Burges: Formulation of Microbial Biopesticides, Springer, 1998).

To produce a dry formulation, bacterial cells, preferably spores can be suspended in a suitable dry carrier (e. g. clay). To produce a liquid formulation, cells, preferably spores, can be re-suspended in a suitable liquid carrier (e. g. water-based) to the desired spore density. The spore density number of spores per ml can be determined by identifying the number of colony-forming units (CFU) on agar medium e. g. potato dextrose agar after incubation for several days at temperatures of about 20 to about 30° C.

According to one embodiment, individual components of the composition according to the invention such as parts of a kit or parts of a binary or ternary mixture may be mixed by the user himself in a spray tank or any other kind of vessel used for applications (e.g seed treater drums, seed pelleting machinery, knapsack sprayer) and further auxiliaries may be added, if appropriate. When living microorganisms, such as the *Paenibacillus* strains of the invention, form part of such kit, it must be taken care that choice and amounts of the other parts of the kit (e. g. chemical pesticidal agents) and of the further auxiliaries should not influence the viability of the microbial pesticides in the composition mixed by the user. Especially for bactericides and solvents, compatibility with the respective microbial pesticide has to be taken into account.

The strains, whole culture broths, cell-free extracts, culture media and/or compounds of formula I of the invention can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzylalcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methylpyrrolidone, fatty acid dimethylamides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethyleneamines.

Suitable adjuvants are compounds, which have a negligible or even no pesticidal activity themselves, and which improve the biological performance of cell-free extract, culture medium or metabolite on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones. Suitable anti-freezing agents are ethylene glycol, propylene glycol, urea and glycerin. Suitable anti-foaming agents are silicones, long chain alcohols, and salts of fatty acids. Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants). Suitable tackifiers or binders are polyvinyl pyrrolidones, polyvinyl acetates, polyvinyl alcohols, polyacrylates, biological or synthetic waxes, and cellulose ethers.

When living microorganisms, such as *Paenibacillus* strains of the invention in form of cells or spores, form part of the compositions, such compositions can be prepared as compositions comprising besides the active ingredients at least one auxiliary (inert ingredient) by usual means (see e. g. H. D. Burges: Formulation of Microbial Biopesticides, Springer, 1998). Suitable customary types of such compositions are suspensions, dusts, powders, pastes, granules, pressings, capsules, and mixtures thereof. Examples for composition types are suspensions (e. g. SC, OD, FS), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). Herein, it has to be taken into account that each formulation type or choice of auxiliary should not influence the viability of the microorganism during storage of the composition and when finally applied to the soil, plant or plant propagation material. Suitable formulations are e. g. mentioned in WO 2008/002371, U.S. Pat. Nos. 6,955,912, 5,422,107.

Examples for suitable auxiliaries are those mentioned earlier herein, wherein it must be taken care that choice and amounts of such auxiliaries should not influence the viability of the microbial pesticides in the composition. Especially for bactericides and solvents, compatibility with the respective microorganism of the respective microbial pesticide has to be taken into account. In addition, compositions with microbial pesticides may further contain stabilizers or nutrients and UV protectants. Suitable stabilizers or nutrients are e. g. alpha-tocopherol, trehalose, glutamate, potassium sorbate, various sugars like glucose, sucrose, lactose and maltodextrine (H. D. Burges: Formulation of Microbial Biopesticides, Springer, 1998). Suitable UV protectants are e. g. inorganic compounds like titanium dioxide, zinc oxide and iron oxide pigments or organic compounds like benzophenones, benzotriazoles and phenyltriazines. The compositions may in addition to auxiliaries mentioned for compositions comprising compounds I herein optionally comprise 0.1-80% stabilizers or nutrients and 0.1-10% UV protectants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Examples for composition types and their preparation are:

i) Water-Soluble Concentrates (SL, LS)

10-60 wt % of a whole culture broth, cell-free extract, culture medium or metabolite of the invention and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible Concentrates (DC)

5-25 wt % of a whole culture broth, cell-free extract, culture medium or metabolite of the invention and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable Concentrates (EC)

15-70 wt % of a whole culture broth, cell-free extract, culture medium or metabolite of the invention and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a whole culture broth, cell-free extract, culture medium or metabolite of the invention and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a whole culture broth, cell-free extract, culture medium or metabolite of the invention are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a whole culture broth, cell-free extract, culture medium or metabolite of the invention are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a whole culture broth, cell-free extract, culture medium or metabolite of the invention are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a whole culture broth, cell-free extract, culture medium or metabolite of the invention are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a whole culture broth, cell-free extract, culture medium or metabolite of the invention are added to 5-30 wt % organic solvent blend (e. g. fatty acid dimethylamide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a whole culture broth, cell-free extract, culture medium or metabolite of the invention, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization initiated by a radical initiator results in the formation of poly(meth)acrylate microcapsules.

Alternatively, an oil phase comprising 5-50 wt % of a whole culture broth, cell-free extract, culture medium or metabolite of the invention, 0-40 wt % water insoluble organic solvent (e. g. aromatic hydrocarbon), and an isocyanate monomer (e. g. diphenylmethane-4,4'-diisocyanate) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a whole culture broth, cell-free extract, culture medium or metabolite of the invention are ground finely and mixed intimately with solid carrier (e. g. finely divided kaolin) ad 100 wt %.

xii) Granules (GR, FG)

0.5-30 wt % of a whole culture broth, cell-free extract, culture medium or metabolite of the invention are ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a whole culture broth, cell-free extract, culture medium or metabolite of the invention are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds.

Preferred examples of seed treatment formulation types or soil application for pre-mix compositions are of WS, LS, ES, FS, WG or CS-type.

Typically, a pre-mix formulation for seed treatment application comprises 0.5 to 99.9 percent, especially 1 to 95 percent, of the desired ingredients, and 99.5 to 0.1 percent, especially 99 to 5 percent, of a solid or liquid adjuvant (including, for example, a solvent such as water), where the auxiliaries can be a surfactant in an amount of 0 to 50 percent, especially 0.5 to 40 percent, based on the pre-mix formulation. Whereas commercial products will preferably be formulated as concentrates (e. g., pre-mix composition (formulation)), the end user will normally employ dilute formulations (e. g., tank mix composition).

Seed treatment methods for applying or treating the strains, whole culture broths, cell-free extracts, culture media, compounds of formula I and compositions of the invention, respectively, to plant propagation material, especially seeds, are known in the art, and include dressing, coating, filmcoating, pelleting and soaking application methods of the propagation material. Such methods are also applicable to the combinations according to the invention. In a preferred embodiment, the strains, whole culture broths, cell-free extracts, culture media, compounds of formula I, and compositions of the invention, respectively, are applied or treated onto the plant propagation material by a method such that the germination is not negatively impacted. Accordingly, examples of suitable methods for applying (or treating) a plant propagation material, such as a seed, is seed dressing, seed coating or seed pelleting and alike.

It is preferred that the plant propagation material is a seed, seed piece (i.e. stalk) or seed bulb.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in the strains, whole culture broths, cell-free extracts, culture media, compounds of formula I, and compositions of the invention, respectively, and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognizable.

An aspect of the present invention includes application of the strains, whole culture broths, cell-free extracts, culture media, compounds of formula I, and compositions of the invention, respectively, onto the plant propagation material in a targeted fashion, including positioning the ingredients in the combination onto the entire plant propagation material or on only parts thereof, including on only a single side or a portion of a single side. One of ordinary skill in the art would understand these application methods from the description provided in EP954213B1 and WO06/112700.

The strains, whole culture broths, cell-free extracts, culture media, compounds of formula I and compositions of the invention, respectively, can also be used in form of a "pill" or "pellet" or a suitable substrate and placing, or sowing, the treated pill, or substrate, next to a plant propagation material. Such techniques are known in the art, particularly in EP1124414, WO07/67042, and WO 07/67044. Application of the strains, whole culture broths, cell-free extracts, culture media, compounds of formula I and compositions, respectively, described herein onto plant propagation material also includes protecting the plant propagation material treated with the combination of the present invention by placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide. Such techniques are known in the art, particularly in WO2005/120226.

Application of the strains, whole culture broths, cell-free extracts, culture media, compounds of formula I and compositions of the invention, respectively, onto the seed also includes controlled release coatings on the seeds, wherein the ingredients of the combinations are incorporated into materials that release the ingredients over time. Examples of controlled release seed treatment technologies are generally known in the art and include polymer films, waxes, or other seed coatings, wherein the ingredients may be incorporated into the controlled release material or applied between layers of materials, or both.

Seed can be treated by applying thereto the strains, whole culture broths, cell-free extracts, culture media, compounds of formula I, and compositions of the invention, respectively, in any desired sequence or simultaneously.

The seed treatment occurs to an unsown seed, and the term "unsown seed" is meant to include seed at any period between the harvest of the seed and the sowing of the seed in the ground for the purpose of germination and growth of the plant. Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the strains, whole culture broths, cell-free extracts, culture media, compounds of formula I and compositions of the invention, respectively. In particular, seed coating or seed pelleting are preferred. As a result of the treatment, the ingredients are adhered on to the seed and therefore available for pest control.

The treated seeds can be stored, handled, sowed and tilled in the same manner as any other active ingredient treated seed.

In particular, the present invention relates to a method for protection of plant propagation material from pests and/or improving the health of plants grown from said plant propagation material, wherein the soil, wherein plant propagation material is sown, is treated with an effective amount of a strain, cell-free extract, culture medium, metabolite or composition of the invention, respectively.

In particular, the present invention relates to a method for protection of plant propagation material from pests, wherein the soil, wherein plant propagation material is sown, is treated with an effective amount of a strain, cell-free extract, culture medium, metabolite or composition of the invention, respectively.

In particular, the present invention relates to a method for protection of plant propagation material from harmful fungi, wherein the soil, wherein plant propagation material is sown, is treated with an effective amount of a strain, cell-free extract, culture medium, metabolite or composition of the invention, respectively.

In particular, the present invention relates to a method for protection of plant propagation material from animal pests (insects, acarids or nematodes), wherein the soil, wherein plant propagation material is sown, is treated with an effective amount of a strain, cell-free extract, culture medium, metabolite or composition of the invention, respectively.

The user applies the compositions of the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

When it comes to the treatment of plant propagation material, especially seeds, the compositions disclosed herein give, after two-to-tenfold dilution, active components concentrations of from 0.01 to 60% by weight, preferably from 0.1 to 40%, in the ready-to-use preparations. Application can be carried out before or during sowing. Methods for applying a strain, cell-free extract, culture medium, metabolite or composition of the invention, respectively, onto plant propagation material, especially seeds, include dressing, coating, pelleting, dusting, soaking and in-furrow application methods of the propagation material. Preferably, the strains, whole culture broths, cell-free extracts, culture media, compounds of formula I or compositions of the invention, respectively, are applied onto the plant propagation material by a method such that germination is not induced, e. g. by seed dressing, pelleting, coating and dusting.

When the strains of the invention are employed in crop protection, wherein the strains are applied as foliar treatment or to the soil, the application rates usually range from about $1 \times 10^6$ to $5 \times 10^{15}$ (or more) CFU/ha, preferably from about $1 \times 10^7$ to about $1 \times 10^{13}$ CFU/ha, even more preferably from $1 \times 10^9$ to $5 \times 10^{12}$ CFU/ha.

When the strains of the invention are employed in seed treatment, the application rates with respect to plant propagation material usually range from about $1 \times 10^1$ to $1 \times 10^{12}$ (or more) CFU/seed, preferably from about $1 \times 10^3$ to about $1 \times 10^{10}$ CFU/seed, and even more preferably from about $1 \times 10^3$ to about $1 \times 10^6$ CFU/seed. Alternatively, the application rates with respect to plant propagation material preferably range from about $1 \times 10^7$ to $1 \times 10^{16}$ (or more) CFU per 100 kg of seed, preferably from $1 \times 10^9$ to about $1 \times 10^{15}$ CFU per 100 kg of seed, even more preferably from $1 \times 10^{11}$ to about $1 \times 10^{15}$ CFU per 100 kg of seed.

When cell-free extracts, culture media and/or compounds of formula I are employed, the solid material (dry matter) are considered as active components, e. g. to be obtained after drying or evaporation of the extraction medium or the suspension medium in case of liquid formulations. When employed in plant protection, the amounts of active components applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e. g. by dusting, coating or drenching seed, amounts of active components of from 0.1 to 1000 g, preferably from 1 to 1000 g, more preferably from 1 to 100 g and most preferably from 5 to 100 g, per 100 kilogram of plant propagation material (preferably seeds) are generally required. When used in the protection of materials or stored products, the amount of active components applied depends on the kind of application area and on the desired effect. Amounts customarily applied in the protection of materials are 0.001 g to 2 kg, preferably 0.005 g to 1 kg, of active components per cubic meter of treated material.

According to one embodiment, individual components of the composition of the invention such as parts of a kit or parts of a binary or ternary mixture may be mixed by the user himself in a spray tank or any other kind of vessel used for applications (e.g seed treater drums, seed pelleting machinery, knapsack sprayer) and further auxiliaries may be added, if appropriate.

If living microorganisms, such as the strains of the invention, form part of such kit, it must be taken care that choice and amounts of the components (e. g. chemical pesticidal agents) and of the further auxiliaries should not influence the viability of the microorganisms in the composition mixed by the user. Especially for bactericides and solvents, compatibility with the respective microorganisms has to be taken into account.

Various types of oils, wetters, adjuvants, fertilizer, or micronutrients, and further pesticides (e. g. herbicides, insecticides, fungicides, growth regulators, safeners, biopesticides) may be added to the strains, cell-free extracts, culture media, metabolites, compounds of formula I and composition of the invention, respectively as premix or, if appropriate not until immediately prior to use (tank mix). These agents can be admixed with the compositions according to the invention in a weight ratio of 1:100 to 100:1, preferably 1:10 to 10:1. Preferably, a composition of the invention comprises a further biopesticide. Even more preferably, a composition of the invention comprises besides an auxiliary and at least one compound of formula I, a microbial pesticide.

A pesticide is generally a chemical or biological agent (such as a virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term pesticides includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology to increase plant growth, biomass, yield or any other quality parameter of the harvestable goods of a crop plant.

EXAMPLES

The present invention will be described in greater detail by means of the following examples. The following examples are for illustrative purposes and are not intended to limit the scope of the invention.

Example 1: Isolation of Novel Bacterial Strains of the Invention

Soil samples from a variety of European locations including Germany were collected. By applying commonly known microbial isolation procedures to these soils, the inventors obtained a variety of bacteria that were further subjected to conventional isolation techniques for providing pure isolates as described herein.

Standard microbial enrichment technique (C. A. Reddy, T. J. Beveridge, J. A. Breznak, G. A. Marzluf, T. M. Schmidt, and L. R. Snyder (eds.). Methods for General and Molecular Microbiology, Am. Soc. Microbiol., Washington, D.C.) was followed to isolate each type of bacteria.

The following strains have been isolated and deposited under Budapest Treaty with the *Deutsche Sammlung von Mikroorganismen and Zellkulturen* (DSMZ) on Feb. 20, 2013:

a) Lu16774 as deposited with DSMZ having the deposit number DSM 26969
b) Lu17007 as deposited with DSMZ having the deposit number DSM 26970
c) Lu17015 as deposited with DSMZ having the deposit number DSM 26971.

Example 2—Characterization of Novel Bacterial Strains

Example 2.1: 16S-rDNA Sequencing

The 16S rRNA gene sequences of the *Paenibacillus* strains were determined by direct sequencing of PCR-amplified 16S rDNA at the DSMZ, Braunschweig, Germany.

Genomic DNA extraction was carried out using the MasterPure™ Gram Positive DNA Purification Kit from Epicentre Biotechnologies according to the manufacturer's instructions. PCR-mediated amplification of the 16S rDNA and purification of the PCR product was carried out as described previously (Int. J. Syst. Bacteriol. 46, 1088-1092, 1996). Purified PCR products were sequenced using the Big Dye® Terminator v1.1 Cycle Sequencing Kit (Applied Biosystems) as directed in the manufacturers protocol. Sequence reactions were electrophoresed using the 3500xL Genetic Analyzer from Applied Biosystems. Sequence ambiguities may be due to the existence of several cistrons encoding 16S rRNAs with different sequences within a single genome (J. Bacteriol. 178(19), 5636-5643, 1996).

The resulting sequence data from the strains was put into the alignment editor AE2 (http://iubio.bio.indiana.edu/soft/molbio/unix/ae2.readme), aligned manually according to the secondary structure of the resulting rRNA molecule and compared with representative 16S rRNA gene sequences of organisms belonging to the *Firmicutes* (Nucl. Acids Res. 27, 171-173, 1999). For comparison, 16S rRNA sequences were obtained from the EMBL and RDP data bases.

The 16S rDNA sequences of the strains of the invention are set forth in the Sequence Listing as indicated in Table 2.

TABLE 2

Sequence listing references of the 16S rDNA of the *Paenibacillus* strains.

| Strain | SEQ ID NO |
| --- | --- |
| Lu16774 | 1 |
| Lu17007 | 2 |
| Lu17015 | 3 |

The 16S rDNA gene identity values in % were calculated by pairwise comparison of the sequences within the alignment of the sequences compared.

Comparison performed of only two sequences based on pairwise sequence alignment are denoted herein as binary values. The other values are based on a multiple sequence alignment of all sequences within the comparison. Higher identity values from multi-sequence comparisons result from the problem that the sequence data of the compared sequences were of different length resulting in a shorter alignment.

The % identity from pair-wise comparisons of the complete rDNA sequences among the three novel strains Lu16774, Lu17007 and Lu17015 was between 99.5 and 99.9% (Table 3, binary values).

TABLE 3

Identity in % of the complete 16S rRNA sequences of the three novel *Paenibacillus* strains (binary values in brackets).

| Strains | Identity of the complete 16S rRNA sequence of the novel *Paenibacillus* strains (%) | | |
|---|---|---|---|
| | Lu16774 | Lu17015 | Lu17007 |
| Lu16774 | — | | |
| Lu17015 | 99.7 (99.5) | — | |
| Lu17007 | 99.9 (99.8) | 99.8 (99.5) | — |

The comparison of the complete 16S rRNA sequence of the three novel strains Lu16774, Lu17007 and Lu17015 with related taxa (see FIG. 9) revealed a high percentage of identity to *Paenibacillus peoriae* (type-strain DSM 8320) with 99.8%. The binary values for pairwise-sequence alignments of *P. peoriae* with the novel strains were as follows: Lu16774: 99.5%, Lu17007: 99.5%; and Lu17015: 99.7% identity, respectively.

A final evaluation of species to which the novel *Paenibacillus* strains Lu16774, Lu17015 and Lu17007 belong was based on the 16S rRNA sequence data not possible.

The sequencing of the complete rDNA resulted for *Paenibacillus peoriae* NRRL BD-62 in 100.0% identity to *P. peoriae* (type strain DSM 8320) confirming the species designation *P. peoriae* for this strain BD-62 (see FIG. 9).

The close relationship of all three novel *Paenibacillus* strains Lu16774, Lu17007 and Lu17015 to *P. peoriae* was confirmed by the comparison with the 16S rRNA sequence of *P. peoriae* strain BD-62 which resulted in identity values of 99.8% (see FIG. 9).

For construction of the phylogenetic dendrogram operations of the ARB package (Nucl. Acids Res. 35, 7188-7196, 2007) were used: based on the evolutionary distance values the phylogenetic tree was constructed by the neighbor-joining method (Jukes, T. H. & Cantor C. R. (1969). Evolution of protein molecules. In Mammalian protein metabolism, pp. 21-132. Edited by H. N. Munro. New York: Academic press) using the correction of Jukes and Cantor (Mol. Biol. Evol. 4, 406-425, 1987). The root of the tree was determined by including the 16S rRNA gene sequence of *Cohnella thermotolerans* into the analysis. The scale bar below the dendrogram indicates 1 nucleotide substitutions per 100 nucleotides. The results are given in FIG. 10.

The phylogenetic dendrogram of these sequences (FIG. 10) shows that the three novel strains Lu16774, Lu17007 and Lu17015 are most-closely related to each other and that their closest relative known to each of them was the *Paenibacillus peoriae* strain NRRL BD-62.

Example 2.2: RiboPrint-Analysis

Standardized, automated ribotyping is performed using the Qualicon RiboPrintersystem. The RiboPrinter system combines molecular processing steps for ribotyping in a stand-alone, automated instrument. The procedure includes cell lysis, digestion of chromosomal DNA with restriction enzyme EcoRI, separation of fragments by electrophoresis, transfer of DNA fragments to a nylon membrane, hybridization to a probe generated from the rrnB operon from *E. coli*, chemiluminescent detection of the probe to the fragments containing rrn operon sequences, image detection and computerized analysis of RiboPrint patterns (Food Technology 50(1), 77-81, 1996; Proc. Natl. Acad. Sci. USA 92, 5229-5233, 1995; Int. Journ. Syst. Bact. 44(3), 454-460, 1994).

Ribotyping have been executed by the DSMZ, Germany with the novel *Paenibacillus* strains Lu16774, Lu17007 and Lu17015 in comparison to the *P. peoriae* strain BD-62 using the restriction enzyme EcoRI. The resulting patterns have been compared using the Software of the RiboPrinter system, the integrated DuPont Identification Library as well as the BioNumerics Software (Applied Maths, Belgium).

Similarity of all three novel strains to BD-62 was between 0.24 and 0.5 (FIG. 11). The three novel strains group in two groups, first comprising Lu17015, whereas the second group comprises the strains Lu16774 and Lu17007. None of the novel strains has a similarity higher than 0.84 to any strain within the DuPont Identification Library and was therefore not identified automatically.

The strain BD-62 has been identified as *Paenibacillus peoriae* based on the entry DUP13142 of the DuPont identification library (entry based on *Paenibacillus peoriae* DSM 8320).

Example 2.3: Morphological and Physiological Characterization

The strains were characterized at the DSMZ in analogy to methods described in Gordon, R. E., Haynes, W. C. & Pang. C. H.-N. (1973): The Genus *Bacillus*, Agriculture Handbook no. 427. Washington D.C.: US Department of Agriculture. The results are given in Table 4.

TABLE 4

Characterization Data of the *Paenibacillus* strains of the invention and comparison to known *Paenibacillus peoriae* strain NRRL BD-62.

| | *Paenibacillus* strains | | | |
|---|---|---|---|---|
| Identification | Lu16774 | Lu17007 | Lu17015 | BD-62 |
| Characteristics | | | | |
| cell form | rod-shaped | rod-shaped | rod-shaped | rod-shaped |
| width [μm] | 0.9-1.0 | 0.9-1.0 | 0.9-1.0 | 0.9-1.0 |
| length [μm] | 3->5.0 | 3-5.0 | 3-5.0 | 2.5-5.0 |
| ellipsoid spores | + | + | + | + |
| swollen sporangium | + | + | + | + |
| Catalase | + | + | + | + |
| Oxidase | − | − | − | − |
| anaerobic growth | + | + | + | + |
| VP reaction | + | + | + | + |
| pH in VP-Medium | 5.2 | 5.7 | 4.8 | 5.2 |
| maximum temperature | | | | |
| positive growth at ° C. | 40 | 40 | 40 | 40 |
| negative growth at ° C. | 50 | 50 | 50 | 50 |
| Growth in: | | | | |
| Medium pH 5.7 | + | + | + | + |
| NaCl 2% | + | + | + | + |
| NaCl 5% | − | − | − | − |
| NaCl 7% | − | − | − | − |
| Acid formation from: | | | | |
| D-Glucose | + | + | + | + |
| L-Arabinose | + | + | + | + |
| D-Xylose | + | + | + | + |
| D-Mannitol | + | + | + | + |
| D-Fructose | + | + | + | + |
| Raffinose | + | + | + | + |
| Trehalose | + | + | + | − |
| Glycerol | + | + | + | + |
| Gas from glucose | + | + | + | + |

TABLE 4-continued

Characterization Data of the *Paenibacillus* strains of the invention and comparison to known *Paenibacillus peoriae* strain NRRL BD-62.

| | *Paenibacillus* strains | | | |
|---|---|---|---|---|
| Identification | Lu16774 | Lu17007 | Lu17015 | BD-62 |
| Hydrolysis of | | | | |
| starch | + | + | + | + |
| gelatin | + | + | + | + |
| casein | + | + | + | ? |
| Tween 80 | − | − | − | − |
| esculin | + | + | + | + |
| Utilisation of | | | | |
| citrate | n.g.* | n.g. | n.g. | n.g. |
| propionate | n.g. | n.g. | n.g. | n.g. |
| NO$_3$ to NO$_2$ | + | + | + | + |
| Indole reaction | − | − | − | − |
| Lecithinase | + | + | + | − |
| Phenylalanine desaminase | − | − | − | − |
| Arginine dihydrolase | − | − | − | − |
| Lysozyme | + | + | + | + |

*n.g. = no growth.

Analysis of the cellular fatty acids performed at the DSMZ resulted that all strains showed at typical profile for *Paenibacillus* spp.

Using the available genetic, physiological and biochemical data, it is shown that the strains Lu16774, Lu17007 and Lu17015 belong to the genus *Paenibacillus*. As the strains Lu16774, Lu17007 and Lu17015 as well as BD-62 do produce gas from glucose, none of them belongs to *Paenibacillus jamilae*.

A phenotypic differentiation between *Paenibacillus peoriae* and *Paenibacillus polymyxa* is primarily possible using characteristics of acid production from certain substrates (Int. J. Syst. Bacteriol. 43(2), 388-390, 1993; In. J. Syst. Bacteriol. 46(6), 988-1003, 1996). None of the novel strains did completely match with its characteristics outlined in Table 4 completely to any of these two species, but in sum of the available genetic, physiological and biochemical data most likely point to the species *Paenibacillus peoriae* and *P. polymyxa* or at least to another species very closely related to *Paenibacillus peoriae* and *P. polymyxa*.

Due to the multitude of *Paenibacillus* species described so far, it is impossible to determine the correct taxonomic species of the three isolates tested based on physiological and morphological criteria from Table 4 (Rainer Borriss, Humboldt University Berlin, unpublished results).

Nevertheless, it was not possible to completely determine the species within this genus. The most closely related species and strain was found to be *Paenibacillus peoriae* BD-62 based on 16S-rDNA analysis (see e. g. FIG. 11).

Example 2.4: Phylogenetic Analysis Based on Genes Coding for DnaN, GyrB, RecF, RecN and RpoA The nucleotide sequences of the genes coding for DnaN, GyrB, RecF, RecN and RpoA have been extracted from complete genome sequences or from public databases (Sequence listings as outlined in Table 28).

The identity tables (FIGS. 12 to 16) have been generated with an all against all approach where every sequence is aligned with every other sequence. The sequence alignment was performed with a program needle (EMBOSS package 6.6.0; Trends in Genetics 16 (6), 276-277). Standard parameters where used (gap creation 10.0; gap extension 0.5). Identity Scores are calculated on the basis of the alignments without taking any gaps into account.

For the phylogenetic trees (FIGS. 17 to 21), multiple sequence alignments that have been performed with Clustal Omega (version 1.2.0; Molecular Systems Biology 7: 539, doi:10.1038/msb.2011.75). The phylogenetic trees are calculated by maximum likelyhood method with the software Dnaml (implemented in the Phylip 3.696 package; Felsenstein 1981, http://evolution.genetics.washington.edu/phylip.html). The dendrograms have been established using a F84 distance model while applying a transition—transversion ratio of two (2). The trees are plotted with the tool Dendroscope (http://dendroscope.org/).

TABLE 28

Sequence listing references of the dnaN, gyrB, recF, recN and rpoA DNA sequences of the *Paenibacillus* strains.

| Strain | Gene | SEQ ID NO |
|---|---|---|
| Lu16774 | dnaN | 4 |
| Lu17007 | dnaN | 5 |
| Lu17015 | dnaN | 6 |
| Lu16774 | gyrB | 7 |
| Lu17007 | gyrB | 8 |
| Lu17015 | gyrB | 9 |
| Lu16774 | recF | 10 |
| Lu17007 | recF | 11 |
| Lu17015 | recF | 12 |
| Lu16774 | recN | 13 |
| Lu17007 | recN | 14 |
| Lu17015 | recN | 15 |
| Lu16774 | rpoA | 16 |
| Lu17007 | rpoA | 17 |
| Lu17015 | rpoA | 18 |

Example 2.5: Core Genome Comparisons and AAI Matrix

Genome comparisons have be performed using the software package EDGAR of the university Gießen (BMC Bioinformatics 10, 154, 2009; (https://edgar.computational-.bio.unigiessen.de/cgi-bin/edgar.cgi). The determination of the core genome, the phylogenetic dendrograms on the basis of the complete genome sequences and the AAI matrix values have been performed using the software package EDGAR. Results are shown in FIG. 22.

Example 3: Growth (Fermentability) of Strains for In-Vivo Tests

For green-house and field trials, the *Paenibacillus* strains were first grown on ISP2 plates (ready-to-use agar from BD [USA], catalog number 277010). Afterwards, baffled shake flasks containing liquid ISP2 medium were inoculated with a colony from the agar plate and incubated for 5-7 days at 150 rpm and 25° C. Depending on the test, either whole culture broth, or the centrifuged and H$_2$O-washed cell pellet, or the supernatant was applied to the plants. A scale-up to 10 L fermenters was possible.

*Paenibacillus* strains were grown in ISP2 liquid media (10 g/L malt extract, 4 g/L Bacto yeast extract, 4 g/L glucose monohydrate) for 6 days at 22° C. at 150 rpm. OD$_{600nm}$ indicating bacterial growth was measured at different time points.

TABLE 5

Bacterial growth of *Paenibacillus* strains in liquid ISP2 medium.

| *Paenibacillus* strain | OD at 600 nm | | |
|---|---|---|---|
| | 0 d | 3 d | 6 d |
| Lu17007 | 0.011 | 3.110 | 3.050 |
| BD-62 | 0.013 | 0.442 | 0.446 |

Example 4—In-Vitro Confrontation Assay for Antifungal Activity

Antagonistic activity of the *Paenibacillus* strains against plant pathogens was shown in in-vitro confrontation assay. The phytopathogenic fungi used are *Sclerotina sclerotiorum* (SCLSCL), *Botrytis cinerea* (BOTRCI), *Alternaria* sp. (ALTESP) and *Phytophthora infestans* (PHYTIN).

As growth medium for BOTRCI, ALTESP, SCLSCL, ISP2 medium is used comprising per litre: 10 g malt extract (Sigma Aldrich, 70167); 4 g Bacto yeast extract (Becton Dickinson, 212750); 4 g glucose monohydrate (Sigma Aldrich, 16301); 20 g Agar (Becton Dickinson, 214510), pH about 7, Aq. bidest. As growth medium for PHYTIN, V8 medium is used comprising per litre: 200 ml of vegetable juice, 3 g calcium carbonate (Merck Millipore, 1020660250); 30 g Agar (Becton Dickinson, 214510), pH 6.8, Aq. bidest.

The *Paenibacillus* strains were point-inoculated on one side of an agar plate. An agar block (approx. 0.3 cm$^2$) containing one actively growing plant pathogen was put in the center of the plate. After incubating for 7-14 days at 25° C., the growth of the plant pathogen was examined, especially for inhibition zones.

Thereafter, the agar plates are incubated at ° C. for about 7-14 days before evaluation. Antibiosis is scored by evaluation of the diameter of the fungi-free zone (zone of inhibition). Competition is scored by comparing the diameter of the growth of the fungal pathogen on plates with bacterial strains in comparison to control plates. Mycoparasitism can be documented in case the bacteria overgrows the fungal pathogen and also parasitize the pathogens. This can be visualized by microscopy.

The novel *Paenibacillus* strains showed antifungal activity against all tested plant pathogens.

TABLE 6

In-vitro confrontation assay results.

| *Paenibacillus* strain | Diameter of zone of inhibition [mm] | | | |
|---|---|---|---|---|
| | PHYTIN | BOTRCI | ALTESP | SCLSCL |
| Lu16774 | 8 | 2 | 2 | 2 |
| Lu17007 | 8 | 8 | 5 | 2 |
| Lu17015 | 8 | 5 | 5 | 2 |
| BD-62 | 2 | 5 | 0 | 0 |

Example 5—Glasshouse Tests for Activity Against Plant Pathogenic Fungi

Use Example 5.1: Activity Against Late Blight on Tomato Caused by *Phytophthora infestans* with Protective Application Commercially available young tomato seedlings ("Goldene Königin") were used for the described greenhouse trial. 2 replications (pots with 1 plant each) were used per treatment. Plants were grown in commercially available substrate (Universal, Floragard) at approx. 22° C. in the greenhouse. The humidity was controlled using a special device (~90% humidity). The plants were sprayed to runoff with crude/whole culture broth of 6 days old cultures of the respective *Paenibacillus* strain (depending on the setup) using a spray cabinet. Culture conditions for the strains are described in Example 3. One day after application the treated plants were inoculated with a suspension of sporangia of *Phytophthora infestans* (PHYTIN). After inoculation, the trial plants were immediately transferred to a humid chamber. The extent of fungal attack on the leaves was visually assessed 5-7 days after inoculation. Fungal attack in the untreated control was between 80-100% and set to 100% for comparison reason.

TABLE 7

| *Paenibacillus* strain | PHYTIN (% fungal attack) |
|---|---|
| Lu17007 | 4 |
| Lu16774 | 20 |
| BD-62 | 53 |

Use Example 5.2: Activity Against Grey Mold on Pepper Caused by *Botrytis cinerea* with Protective Application Commercially available young pepper seedlings ("Neusiedler Ideal") were used for the described greenhouse trial. 2 replications (pots with 1 plant each) were used per treatment. Plants were grown in commercially available substrate (Universal, Floragard) at approx. 22° C. in the greenhouse. The humidity was controlled using a special device (~90% humidity). The plants were sprayed to runoff with crude culture broth of 6 days old cultures of the respective *Paenibacillus* strain (depending on the setup) using a spray cabinet. Culture conditions for the strains are described in Example 3. One day after application the treated plants were inoculated with a suspension of spores of *Botrytis cinerea* (BOTRCI). After inoculation, the trial plants were immediately transferred to a humid chamber. The extent of fungal attack on the leaves was visually assessed 5-7 days after inoculation. Fungal attack in the untreated control was between 80-100% and set to 100% for comparison reason.

TABLE 8

| *Paenibacillus* strain | BOTRCI (% fungal attack) |
|---|---|
| Lu17007 | 2 |
| Lu16774 | 16 |
| Lu17015 | 20 |
| BD-62 | 97 |

Use Example 5.3: Activity Against Early Blight on Tomato Caused by *Alternaria solani* with Protective Application Commercially available young tomato seedlings ("Goldene Königin") were used for the described greenhouse trial. 2 replications (pots with 1 plant each) were used per treatment. Plants were grown in commercially available substrate (Universal, Floragard) at approx. 22° C. in the greenhouse. The humidity was controlled using a special device (~90% humidity). The plants were sprayed to runoff with crude/whole culture broth of 6 days old cultures of the respective *Paenibacillus* strain (depending on the setup) using a spray cabinet. Culture conditions for the strains are described in Example 3. One day after application the treated plants were inoculated with a suspension of spores of *Alternaria solani* (ALTESO). After inoculation, the trial plants were immediately transferred to a humid chamber. The extent of fungal attack on the leaves was visually assessed 5-7 days after inoculation. Fungal attack in the untreated control was between 80-100% and set to 100% for comparison reason.

TABLE 9

| *Paenibacillus* strain | ALTESO (% fungal attack) |
|---|---|
| Lu17007 | 3 |
| Lu17015 | 16 |
| BD-62 | 96 |

Use Example 5.4: Activity Against Soybean Rust on Soybean Caused by *Phakopsora pachyrhizi* with Protective Application Commercially available young soybean seedlings ("Mentor") were used for the described greenhouse trial. 2 replications (pots with 1 plant each) were used per treatment. Plants were grown in commercially available substrate (Universal, Floragard) at approx. 22° C. in the greenhouse. The humidity was controlled using a special device (~90% humidity). The plants were sprayed to runoff with crude culture broth of 2-6 days old cultures of *Paenibacillus* spp. (depending on the setup) using a spray cabinet. One day after application the treated plants were inoculated with a suspension of spores of *Phakopsora pachyrhizi* (PHAKPA). After inoculation, the trial plants were immediately transferred to a humid chamber. The extent of fungal attack on the leaves was visually assessed 5-7 days after inoculation.

Use Example 5.5: Activity Against *Fusarium* Head Blight on Wheat Caused by *Fusarium Graminearum* with Protective Application Commercially available young wheat seedlings were used for the described greenhouse trial. 2 replications (pots with 1 plant each) were used per treatment. Plants were grown in commercially available substrate (Universal, Floragard) at approx. 22° C. in the greenhouse. The humidity was controlled using a special device (~90% humidity). The plants were sprayed to runoff with crude culture broth of 2-6 days old cultures of *Paenibacillus* spp. (depending on the setup) using a spray cabinet. Culture conditions are described in Example 3. One day after application the treated plants were inoculated with a suspension of spores of *Fusarium graminearum* (GIBBZE). After inoculation, the trial plants were immediately transferred to a humid chamber. The extent of fungal attack on the leaves was visually assessed 5-7 days after inoculation.

Use Example 5.6: Activity Against Speckled Leaf Blotch on Wheat Caused by *Septoria Tritici* with Protective Application Commercially available young wheat seedlings were used for the described greenhouse trial. 2 replications (pots with 1 plant each) were used per treatment. Plants were grown in commercially available substrate (Universal, Floragard) at approx. 22° C. in the greenhouse. The humidity was controlled using a special device (~90% humidity). The plants were sprayed to runoff with crude culture broth of 2-6 days old cultures of *Paenibacillus* spp. (depending on the setup) using a spray cabinet. Culture conditions are described in Example 3. One day after application the treated plants were inoculated with a suspension of spores of *Septoria tritici* (SEPTTR). After inoculation, the trial plants were immediately transferred to a humid chamber. The extent of fungal attack on the leaves was visually assessed 21-28 days after inoculation.

Use Example 5.7: Activity of the *Paenibacillus* Cells and of the Supernatant Against Various Pathogens with Protective Application Whole culture broth from 6 days old cultures of *Paenibacillus* strain Lu17007 was obtained according to Use Example 3 and used as in the experimental setup of Use Example 5.1 to 5.3. Alternatively, such whole culture broth was filtered through a filter with 0.2 μm pore size to obtain the culture medium and the crude cell fraction. The crude cell fraction could further be washed three times with the original volumes of phosphate-buffered saline to obtain washed cells.

The glasshouse trials were performed as described in the Use Examples 5.1, 5.2 and 5.3 above for the respective pathogens *Phytophthora infestans, Botrytis cinerea* and *Alternaria* solani. The extent of fungal attack on the leaves was visually assessed 5-7 days after inoculation. Fungal attack in the untreated control was between 80-100% and set to 100% for comparison reason.

TABLE 10

| *Paenibacillus* culture | % fungal attack by | | |
|---|---|---|---|
| component | BOTRCI | ALTESO | PHYTIN |
| Whole culture broth | 0 | 2 | 7 |
| Culture medium | 3 | 40 | 3 |
| Crude cell fraction | 0 | 5 | 4 |
| Washed cells | 1 | 10 | 1 |

Example 6—Enzymatic Tests

Use Example 6.1: Chitinase

Chitinase Test Solid Medium:

2 g/l $NaNO_3$, 1 g/l $K_2HPO_4$, 0.5 g/l $MgSO_4$, 0.5 g/l KCl, 0.2 g/l pepton, 15 g/l agar, 10 g/l chitin from crab shells (Sigma-Aldrich C7170).

Test solid medium is autoclaved and filled into 9 cm Petri dishes. *Paenibacillus* strains are inoculated in the center of the plates and incubated for two days at 27° C. Thereafter, the plates are stained with a 1:3 diluted Lugol solution (Carl Roth N052.2) for 5 to 10 min. Lugol solution is poured out and the plates are photographed and evaluated. Growth of the different strains was no more than 5-10 mm. Non-stained zones (correlating with chitinase activity) varied from 0 mm (no activity; "–" in Table 11) to several cm ("+" in Table 11).

Use Example 6.2: Cellulase

Cellulase Test Solid Medium:
2 g/l NaNO$_3$, 1 g/l K$_2$HPO$_4$, 0.5 g/l MgSO$_4$, 0.5 g/l KCl, 0.2 g/l pepton, 15 g/l agar, carboxymethyl cellulose, sodium salt (Sigma-Aldrich 419273).

Medium is autoclaved poured into 9 cm Petri dishes. *Paenibacillus* strains are inoculated in the center of the plates and incubated for two days at 27° C. After incubation plates are stained with a 1:3 diluted Lugol solution (Carl Roth N052.2) for 5 to 10 min. Lugol solution is poured out and plates photographed.

Use Example 6.3: Amylase

Amylase Test Solid Medium:
2 g/l NaNO$_3$, 1 g/l K$_2$HPO$_4$, 0.5 g/l MgSO$_4$, 0.5 g/l KCl, 0.2 g/l pepton, 15 g/l agar, 10 g/l soluble starch (Merck 1.01252).

Medium is autoclaved poured into 9 cm Petri dishes. *Paenibacillus* strains are inoculated in the center of the plates and incubated for two days at 27° C. After incubation plates are stained with a 1:3 diluted Lugol solution (Carl Roth N052.2) for 5 to 10 min. Lugol solution is poured out and plates photographed.

TABLE 11

Chitinase, cellulose and amylase activities of *Paenibacillus* strains.

| Strain | Chitinase | Cellulase | Amylase |
|---|---|---|---|
| Lu16774 | + | + | − |
| Lu17007 | ++ | + | + |
| Lu17015 | + | + | + |
| BD-62 | − | − | − |

−, no activity;
(+), low activity;
+, regular activity;
++, high activity.

Example 7—Fusaricidin-Type Metabolites Obtained from *Paenibacillus* Strains

Example 7.1: Large Scale Cultivation of Bacterial Isolates and Extraction of Fusaricidin-Type Metabolites a) Cultivation The *Paenibacillus* strains were cultivated on agar plates containing GYM medium (10 g/l glucose, 4 g/l yeast extract, 10 g/l malt extract; pH 5.5, adjusted before autoclaving) and 20 g/l agar. Cultivation was performed for 10 to 20 days at room temperature. For maintenance agar slants with the same medium were used and stored at 4° C.

Small scale liquid cultures (250 ml GYM medium in 500 ml flasks) were inoculated with 4-5 pieces of a well grown agar culture and cultivated in an orbital shaker at 120 rpm at room temperature (20-23° C.).

Large scale fermentations were performed in 20 l fermenters with 15 l GYM medium (total capacity of fermenters was not used because of foam formation) inoculated with 250 ml well grown liquid culture and fermentation was carried out at room temperature (20-23° C.) with agitation (120 rpm) and aeration (3 l/min) for 5 to 8 days.

b) Extraction

One equal volume of isopropanol was added to the whole culture broth (no separation of biomass from liquid culture was performed). After agitation and incubation for 2 to 16 hours, common table salt (sodium chloride—100 to 200 g/l) was added to the mixture until phase separation of the organic and aqueous phase was visible.

The isopropanol phase was concentrated in vacuo. The resulting extract, still containing large amount of salt, was dissolved in methanol, centrifuged for better precipitation of salt residues, and the organic phase was concentrated again. This step was repeated until no salt precipitate was present anymore.

c) Purification i) Silica Gel Chromatography 30 grams of extract were dissolved in methanol and bound to 50 g silica gel (Merck, K60, 70-230 mesh), dried at 40° C. and layered onto 1 kg of silica gel (column 10 cm diameter, 30 cm high approx.).

Elution was carried out in four steps as following:
Step 1-4 l ethyl acetate
Step 2-4 l ethyl acetate:methanol (3:1, v/v)
Step 3-7 l ethyl acetate:methanol (1:1, v/v)
Step 4-4 l methanol The third fraction (intermediate 1), containing the active compounds, was dried in vacuo and dissolved in 40% methanol (MeOH) in 0.1% formic acid (FA) (concentration: 100 mg/ml). The other fractions were discarded.

ii) Chromabond HR-X Fractionation 20 ml of intermediate 1 was loaded onto a previously equilibrated (with 40% MeOH in 0.1% FA) Chromabond HR-X cartridge (Macherey-Nagel, 1000 mg, ref 730941). The cartridge was washed with 100 ml 40% MeOH in 0.1% FA and eluted with 60 ml 70% MeOH in 0.1% FA. This intermediate 1-1 was then dried in vacuo.

iii) Preparative HPLC on a Sunfire C18 Column

Intermediate 1-1 was dissolved in DMSO (concentration: 200 mg/ml) and 300 μl of intermediate 1-1 were chromatographed on a Sunfire C18 column (19×250 mm, 5 μm, Waters) as follows:
16 min at 10 ml/min, isocratic 70% 0.2 FA; 30% acetonitrile (ACN),
1 min at 14 ml/min, gradient to 65% 0.2% FA; 35% ACN,
5 min at 14 ml/min, isocratic 65% 0.2% FA; 35% ACN.

Five fractions could be detected. All five resulting fractions were dried in vacuo and dissolved in DMSO (concentration: 125 mg/ml). Further purification was performed using the same column and isocratic conditions (flow: 10.5 ml/min) adjusted for every fraction (12.5 mg per run):

Fraction 1:69% 0.2 FA; 31% ACN; two peaks detected (1-1 and 1-2)
Fraction 2: 69% 0.2 FA; 31% ACN; two peaks detected (2-1 and 2-2)
Fraction 3: 69% 0.2 FA; 31% ACN; three peaks detected (3-1, 3-2 and 3-3)
Fraction 4/5: 67% 0.2 FA; 33% ACN; one peak detected (4/5)
Fraction 6: 65% 0.2 FA; 35% ACN; two peaks detected (6-1 and 6-2)

The purity and quantity of the following samples was sufficient for NMR analysis and structure elucidation: peaks 1-2, 2-1, 3-2, 4/5 and 6-1.

Example 7.2: Structural Elucidation of Novel Compounds 1A and 1 B

From peak 2-1 of fraction 2, a mixture of compounds 1A and 1 B (ratio about 3:7) was obtained as a brown oil ($[\alpha]_D^{25}$=+20.9 (c=0.6, DMSO-d$_6$)).

The molecular formula $C_{47}H_{78}N_{10}O_{12}$ of the major component, compound 1 B, was deduced from the HR-ESI-MS spectrum which gave a peak at m/z 975.5863 [M+H]$^+$; ESI-MS: 975.6 (100%, [M+H]$^+$), 488.4 (51%, [M+2H]$^{2+}$).

Besides, the mixture also contained as minor component, the lighter homologue 1A, and the mass difference between both compounds was 14 amu. This observation was supported by a second peak observed in the ESI-MS spectrum at m/z 961.6.

The NMR spectra (Table 12) included in addition to signals of exchangeable protons between δ 6.83 and 8.58, resonances of carbonyl in the range of δ 166.0-174.5 and methine signals between δ 47.8 and δ 60.4 indicative for a peptide.

Extensive analysis of the 1 D- and 2D-NMR data of compound 1 B revealed the presence of six amino acids including tyrosine (Tyr), glutamine (Gln), alanine (Ala), two threonines (Thr1 and Thr2) and isoleucine (Ile). Their sequence was found using two or three bonds correlations across amide functions. Thus, COSY, NOESY (FIG. 2) and HMBC (FIG. 3) spectra depicted correlations from the nitrogen-proton of Thr2 at δ 8.58 to the signal of methine proton of Thr2 at δ 3.84 and the carbonyl at δ 166.7 of Tyr while the same relationship was noted between the nitrogen-proton of Tyr at δ 8.52 and the signal of methylene proton of Tyr at δ 2.60 and the carbonyl at δ 170.4 of Ile. Furthermore, the methine hydrogen of Ile at δ 4.16 had a strong correlation with the carbonyl signal of Ile at δ 170.4 and a weak contact with that of Thr1 at δ 168.6; the signal of the β-methine proton at δ 5.30 of Thr1 correlated with the carbonyl signal at δ 170.4 of Ala. Additionally to the aforementioned correlations, others were displayed from the N-proton at δ 7.27 of Ala to the methine proton at δ 4.20 of the same amino acid while this latter proton had the same interaction with the carbonyl of its amino and the one of Gln. Besides, a cross peak was revealed from the exchangeable proton at δ 8.20 of Gln to the methine hydrogen at δ 3.87 of Gln and the carbonyl of Thr2 at δ 170.6; these above-mentioned data suggested the cyclodepsipeptidic structure for compound 1 B.

This cyclodepsipeptide 1 B contained a terminal guanidine β-hydroxy fatty acid attached to Thr1 since a key correlation was observed between the signal of its α-methine proton at δ 4.39 and the resonance of a carbonyl at δ 171.9; HMBC contacts from that carbonyl at δ 171.9 to the α-methylene protons at δ 2.35 and the β-methine proton at δ 3.77 were further observed as well as between the methylene protons at δ 3.03 and the guanidine carbon at δ 157.2. The side chain was deduced to contain twelve methylene groups between the 3-hydroxy and the guani-guanidine group on the basis of the fragment ion observed in the APCI-MS-MS spectrum of the parent [M+H]$^+$ ion at m/z 256.2. Likewise, this spectrum provided information (FIG. 4b) which confirmed the connection sequence of amino acids and led to elucidate the structure of compound 1B as shown in FIG. 1.

Signals of a $CH_2$ group at 2.80, 2.52/36.3 in the 1D- and 2D-spectra corresponded presumably to the β-$CH_2$ group of asparagine (Asn) in compound 1A. This conclusion was supported by reported data (Heterocycles 53, 1533-1549, 2000) in conjunction to fragments obtained from MS/MS of the parent peak at m/z 961.6 (FIG. 4a). Likewise, the latter analyses provided information (FIGS. 4a, 4b) which confirmed the connection sequence of amino acids in both compounds and led to elucidate the structure of compounds 1A and 1B as shown in FIG. 1.

Example 7.3: Structural Identification of Compounds 2A and 2B as Fusaricidins C and D From peak 1-2 of fraction 1, a mixture of compounds 2A and 2B (ratio about 1:1) was obtained as a brown oil. The molecular formula of the heavier component, compound 2B, was determined to be $C_{46}H_{76}N_{10}O_{12}$ on the basis of the low resolution mass spectrometry. Analysis of the NMR data (Table 13) allowed to identify compound 2B as fusaricidin D. The lighter component of the mixture, compound 2A, was likewise identified as fusaricidin C, in which the Gln residue of fusaricidin C is replaced by Asn.

The mass spectrometric fragmentation pattern of the parent ions of m/z 961.6 and 947.6 for compounds 2B and 2A, respectively, (FIGS. 5a, 5b) confirmed the length of the substituted fatty acid side chain to be identical as in compound 1B. Fusaricidins C and D have formerly been reported by Kajimura et al. (J. Antibiot. 50, 220-228, 1997).

Example 7.4: Structural Identification of Compound 3 as LI-F08b

From peak 6-1 of fraction 6, compound 3 was isolated as a brown oil and its low resolution presented a peak at m/z 925.6 [M+H]$^+$ which, combined with NMR data (Table 14), led to the molecular formula $C_{44}H_{80}N_{10}O_{11}$. Compound 3 showed similar features in the NMR spectra as compound 1B and compound 2B (fusaricidin D) except for the presence of aromatic signals (Table 14). Thus, characteristic resonances of a peptide were observed namely ten signals of protons attached to nitrogen between δ 6.89 and 8.49, eight resonances of carbonyl ranged between δ 168.1 and 174.3, and six signals of N-methine comprised between δ 48.0 and 59.5. A detailed analysis of the HMQC, COSY and TOCSY spectra revealed the presence of six amino acids including Gln, two units of Thr, two units of Ile and Ala. Furthermore, these spectra showed chemical shifts attributable to the same 3-hydroxyl fatty acid with a terminal guanidine as in compounds 1A, 1B and fusaricidins C (2A) and D (2B). The position of this side chain was determined on the basis of a long range correlation found on the HMBC spectrum between the proton signal of N-methine at δ 4.44 of Thr1 and the carbonyl signal at δ 172.1 of the fatty acid. The sequence of the amino acids was deduced from NOESY interactions and the fragmentation pattern (FIG. 6).

The combination of the NMR data (Table 14) and mass spectrometry led to identify the metabolite compound 3 as LI-F08b, herein also called fusaricidin LI-F08b, reported for the first time by Kuroda et al. (Heterocycles 53, 1533-1549, 2000).

Example 7.5: Structural Identification of Compounds 4A and 4B as LI-F06a and LI-F06b and of Compounds 5A and 5B as Fusaricidin A and B, Respectively From peak 4/5 of fraction 4/5, a mixture of two further metabolites, compounds 4A and 4B (ratio about 1:3), was obtained which gave two peaks at m/z 897.5 (4A) and 911.6 (4B) in the ESI-MS spectrum, suggesting two further homologous cyclodepsipeptides. Resonances indicative for peptides were observed in their NMR spectra (Table 15) as well as those of a β-hydroxyl fatty acid terminating in a guanidine group. The fragmentation patterns of both parent ions found for compounds 4A and 4B (FIGS. 7a, 7b) allowed to determine the sequence of amino acids and to identify the constituents of the mixture as LI-F06a (4A) and LI-F06b (4B), respectively.

Obtained from peak 3-2 of fraction 3, the mixture of compounds 5A and 5B (ratio about 1:3) was analyzed in the same manner. The ESI mass spectrum of the mixture showed two peaks at m/z 883.6 (5A) and 897.5 (5B) and the fragmentation patterns of these parent ions (FIGS. 8a, 8b) in conjunction to NMR data (Table 16) allowed to identify the components as fusaricidin A (5A) and fusaricidin B (5B). The data found for 4A, 4B, 5A and 5B matched those previously reported. (J. Antibiot. 50, 220-228, 1997; Heterocycles 53, 1533-1549, 2000).

TABLE 12

$^1$H (DMSO-$d_6$, 600 MHz) and $^{13}$C-NMR (DMSO-$d_6$, 150 MHz) data of compounds 1A and 1B.

Compounds 1

| | Compound 1A | | | Compound 1B | |
|---|---|---|---|---|---|
| *Pos. | $\delta_H$ | $\delta_C$ | Pos. | $\delta_H$ | $\delta_C$ |
| Thr1 | | | Thr1 | | |
| NH | 7.79 (br) | — | NH | 8.18 (br s) | — |
| 1 | — | 168.6 | 1 | — | 168.6 |
| 2 | 4.46 (br d, 8.5) | 56.4 | 2 | 4.39 (br d, 8.7) | 56.9 |
| 3 | 5.30 (overlapped) | 70.2 | 3 | 5.30 (m) | 70.2 |
| 4 | 1.13 (overlapped) | 16.6 | 4 | 1.13 (d, 6.4) | 16.7 |
| Ala | | | Ala | | |
| NH | 7.22 (br) | — | NH | 7.27 (br s) | — |
| 1 | — | nf* | 1 | — | 170.4 |
| 2 | 4.13 (overlapped) | 47.7 | 2 | 4.20 (m) | 47.8 |
| 3 | 1.11 (overlapped) | 17.8 | 3 | 1.17 (d, 7.1) | 17.8 |
| Asn | | | Gln | | |
| NH | 8.33 (overlapped) | — | NH | 8.20 (br s) | — |
| 1 | — | 169.7 | 1 | — | 170.4 |
| 2 | 4.20 (1H, m) | 50.6 | 2 | 3.87 (m) | 53.2 |
| 3 | 2.52 (m), 2.80 (dd, 5.9, 15.1) | 36.3 | 3 | 1.96 (m), 2.08 (m) | 26.2 |
| 4 | — | 172.5 | 4 | 2.08 (m), 2.18 (m) | 32.0 |
| 5 | — | — | 5 | — | 174.3 |
| NH$_2$ | 6.99 (br s), 7.42 (br s) | — | NH$_2$ | 6.83 (br s), 7.26 (br s) | — |
| Thr2 | | | Thr2 | | |
| NH | 8.50 (overlapped) | — | NH | 8.58 (br s) | — |
| 1 | — | 170.6 | 1 | — | 170.6 |
| 2 | 3.94 (m) | 59.9 | 2 | 3.84 (m) | 60.5 |
| 3 | 3.94 (m) | 65.5 | 3 | 3.85 (m) | 65.8 |
| 4 | 1.05 (br) | 20.3 | 4 | 1.08 (overlapped) | 20.0 |
| Tyr | | | Tyr | | |
| NH | 8.48 (overlapped) | — | NH | 8.52 (br s) | — |
| 1 | — | nf | 1 | — | 166.7 |
| 2 | 4.60 (m) | 54.2 | 2 | 4.51 (m) | 54.5 |
| 3 | 2.60 (overlapped) 2.88 (overlapped) | 36.8 | 3 | 2.60 (m), 2.88 (m) | 36.9 |
| 4 | — | 127.7 | 4 | — | 127.8 |
| 5 and 9 | 7.07 (d, 8.7) | 130.2 | 5 and 9 | 7.06 (d, 8.5) | 130.2 |
| 6 and 8 | 6.60 (overlapped) | 114.7 | 6 and 8 | 6.60 (d, 8.5) | 114.7 |
| 7 | — | 155.9 | 7 | — | 155.9 |
| Ile | | | Ile | | |
| NH | 7.28 (br s) | — | NH | 7.42 (br s) | — |
| 1 | — | nf | 1 | — | 170.4 |
| 2 | 4.16 (overlapped) | 56.5 | 2 | 4.16 (br d, 8.5) | 56.5 |
| 3 | 1.34 (overlapped) | 37.2 | 3 | 1.34 (m) | 37.2 |
| 4 | 1.34 (overlapped) | 25.4 | 4 | 1.22 (m), 1.34 (m) | 25.4 |
| 5 | 0.52 (overlapped) | 14.4 | 5 | 0.53 (overlapped) | 14.4 |
| 6 | 0.59 (overlapped) | 11.4 | 6 | 0.61 (overlapped) | 11.4 |
| *FA | | | FA | | |
| 1 | — | 171.9 | 1 | — | 171.9 |
| 2 | 2.35 (overlapped) | 43.1 | 2 | 2.35 (m) | 43.3 |
| 3 | 3.77 (overlapped) | 67.5 | 3 | 3.77 (m) | 67.5 |
| 4 | 1.34 (overlapped) | 36.8 | 4 | 1.34 (m) | 36.9 |
| 5-12 | 1.19-1.30 (br s) | 29.0-29.2 | 5-12 | 1.19-1.30 (br s) | 29.0-29.2 |
| 13 | 1.25 (br s) | 21.2 | 13 | 1.25 (br s) | 21.2 |
| 14 | 1.43 (overlapped) | 28.7 | 14 | 1.43 (m) | 28.5 |
| 15 | 3.03 (overlapped) | 40.6 | 15 | 3.03 (q, 6.6) | 40.6 |
| *Gu | | | Gu | | |
| NH | nf | — | NH | 8.40 (br s) | — |
| 16 | — | 157.2 | 16 | — | 157.2 |

*Pos. = position; FA = fatty acid; Gu = Guanidine; nf = not found.
Legend applies also to Tables 13 to 16.

TABLE 13

$^1$H (DMSO-$d_6$, 600 MHz) and $^{13}$C-NMR (DMSO-$d_6$, 150 MHz) data of compounds 2A and 2B.
Compounds 2 = fusaricidins C and D

| | Compound 2A = fusaricidin C | | | Compound 2B = fusaricidin D | |
|---|---|---|---|---|---|
| Pos. | $\delta_H$ | $\delta_C$ | Pos. | $\delta_H$ | $\delta_C$ |
| Thr1 | | | Thr1 | | |
| NH | 7.66 (d, 7.1) | — | NH | 8.17 (br s) | — |
| 1 | — | 168.5 | 1 | — | 168.6 |
| 2 | 4.44 (br d, 8.9) | 56.6 | 2 | 4.40 (br d, 8.9) | 57.0 |
| 3 | 5.31 (m) | 70.2 | 3 | 5.30 (m) | 70.3 |
| 4 | 1.13 (overlapped) | 16.5 | 4 | 1.14 (overlapped) | 16.7 |
| Ala | | | Ala | | |
| NH | 7.21 (br) | — | NH | 7.60 (br s) | — |
| 1 | — | nf | 1 | — | 170.6 |
| 2 | 4.12 (m) | 47.7 | 2 | 4.19 (m) | 47.8 |
| 3 | 1.12 (overlapped) | 17.8 | 3 | 1.17 (d, 7.2) | 17.7 |
| Asn | | | Gln | | |
| NH | 8.26 (br) | — | NH | 8.08 (br s) | — |
| 1 | — | 169.7 | 1 | — | 170.4 |
| 2 | 4.21 (m) | 50.5 | 2 | 3.86 (m) | 53.2 |
| 3 | 2.53 (overlapped), 2.80 (dd, 6.3, 15.0) | 36.3 | 3 | 1.98 (m), 2.09 (m) | 26.1 |
| 4 | — | 172.6 | 4 | 2.10 (m), 2.18 (m) | 31.9 |
| 5 | | | 5 | — | 174.3 |
| NH$_2$ | nf | — | NH$_2$ | 6.84 (br s), 7.28 (br s) | — |
| Thr2 | | | Thr2 | | |
| NH | 8.52 (overlapped) | — | NH | 8.47 (overlapped) | — |
| 1 | — | 170.3 | 1 | — | 170.6 |
| 2 | 3.85 (m) | 60.5 | 2 | 3.94 (m) | 59.9 |
| 3 | 3.86 (m) | 65.8 | 3 | 3.92 (m) | 65.7 |
| 4 | 1.09 (d, 5.7) | 19.9 | 4 | 1.05 (d, 5.8) | 20.2 |
| OH-3 | 4.96 (br d, 4.2) | — | OH-3 | 5.05 (d, 2.9) | — |
| Tyr | | | Tyr | | |
| NH | 8.46 (overlapped) | — | NH | 8.52 (overlapped) | — |
| 1 | — | nf | 1 | — | 172.3 |
| 2 | 4.60 (m) | 54.2 | 2 | 4.52 (m) | 54.6 |
| 3 | 2.63 (overlapped) 2.87 (overlapped) | 36.9 | 3 | 2.63 (m), 2.87 (m) | 36.9 |
| 4 | — | 127.7 | 4 | — | 127.7 |
| 5 and 9 | 7.08 (overlapped) | 130.2 | 5 and 9 | 7.06 (d, 8.4) | 130.2 |
| 6 and 8 | 6.60 (overlapped) | 114.7 | 6 and 8 | 6.60 (d, 8.4) | 114.7 |
| 7 | — | 155.8 | 7 | — | 155.8 |
| OH | nf | — | OH | 9.13 (br s) | — |
| Val | | | Val | | |
| NH | 7.30 (overlapped) | — | NH | 7.42 (br s) | — |
| 1 | — | nf | 1 | — | 170.3 |
| 2 | 4.12 (br s) | 57.5 | 2 | 4.12 (br s) | 57.5 |
| 3 | 1.59 (m) | 30.9 | 3 | 1.59 (m) | 31.0 |
| 4 | 0.56 (d, 6.4) | 18.2 | 4 | 0.57 (d, 6.3) | 18.3 |
| 5 | 0.35 (d, 6.5) | 18.7 | 5 | 0.40 (d, 6.6) | 18.7 |
| FA | | | FA | | |
| 1 | — | nf | 1 | — | 172.0 |
| 2 | 2.37 (overlapped) | 43.1 | 2 | 2.37 (m) | 43.3 |
| 3 | 3.79 (overlapped) | 67.5 | 3 | 3.79 (m) | 67.6 |
| 4 | 1.35 (overlapped) | 36.9 | 4 | 1.35 (m) | 36.9 |
| 5 | 1.22 (overlapped) | 25.3 | 5 | 1.22 (br s) | 25.3 |
| 6-12 | 1.20-1.27 (br s) | 29.1-29.2 | 6-12 | 1.20-1.27 (br s) | 29.1-29.2 |
| 13 | 1.26 (br s) | 26.1 | 13 | 1.26 (br s) | 26.1 |
| 14 | 1.44 (overlapped) | 28.5 | 14 | 1.44 (m) | 28.7 |
| 15 | 3.07 (overlapped) | 40.7 | 15 | 3.07 (q, 6.7) | 40.7 |
| Gu | | | Gu | | |
| NH | nf | — | NH | 7.60 (br s) | — |
| 16 | — | 156.8 | 16 | — | 156.8 |

TABLE 14

$^1$H (DMSO-d$_6$, 600 MHz) and $^{13}$C-NMR (DMSO-d$_6$, 150 MHz) data of compound 3 being LI-F08b.
Compound 3 = LI-F08b

| Pos. | $\delta_H$ | $\delta_C$ |
|---|---|---|
| Thr1 | | |
| NH | 7.55 (br s) | — |
| 1 | — | 168.1 |
| 2 | 4.44 (br d, 8.4) | 56.6 |
| 3 | 5.33 (m) | 70.2 |
| 4 | 1.15 (d, 6.5) | 16.7 |
| Ala | | |
| NH | 7.53 (br s) | — |
| 1 | — | 170.6 |
| 2 | 4.05 (m) | 48.0 |
| 3 | 1.22 (br s) | 17.2 |
| Gln | | |
| NH | 7.93 (br s) | — |
| 1 | — | 170.5 |
| 2 | 3.94 (m) | 52.7 |
| 3 | 1.98 (m), 2.09 (m) | 26.5 |
| 4 | 2.12 (m), 2.20 (m) | 31.9 |
| 5 | — | 174.3 |
| NH$_2$ | 6.89 (br s), 7.32 (br s) | — |
| Thr2 | | |
| NH | 8.48 (br s) | — |
| 1 | — | 170.7 |
| 2 | 4.03 (m) | 59.5 |
| 3 | 3.98 (m) | 65.7 |
| 4 | 1.08 (d, 6.1) | 19.8 |
| Ile1 | | |
| NH | 8.49 (br s) | — |
| 1 | — | 172.5 |
| 2 | 4.15 (t, 7.6) | 57.3 |
| 3 | 1.81 (m) | 35.4 |
| 4 | 1.17 (m), 1.41 (m) | 24.4 |
| 5 | 0.80 (t, 6.3) | 10.6 |
| 6 | 0.81 (d, 7.2) | 15.5 |
| Ile2 | | |
| NH | 7.30 (br s) | — |
| 1 | — | 171.3 |
| 2 | 4.53 (m) | 55.3 |
| 3 | 1.65 (m) | 38.2 |
| 4 | 1.01 (m), 1.37 (m) | 25.5 |
| 5 | 0.83 (t, 6.4) | 11.4 |
| 6 | 0.70 (d, 7.4) | 14.2 |
| FA | | |
| 1 | — | 172.1 |
| 2 | 2.37 (d, 5.7) | 43.4 |
| 3 | 3.77 (m) | 67.6 |
| 4 | 1.37 (m) | 36.9 |
| 5-12 | 1.20-1.28 (br s) | 29.0-29.2 |
| 13 | 1.25 (br s) | 26.2 |
| 14 | 1.43 (m) | 28.7 |
| 15 | 3.03 (q, 6.7) | 40.6 |
| Gu | | |
| NH | 8.37 (br s) | — |
| 16 | — | 157.2 |

TABLE 15

$^1$H (DMSO-d$_6$, 600 MHz) and $^{13}$C-NMR (DMSO-d$_6$, 150 MHz) data of compounds 4A and 4B.
Compounds 4 = LI-F06a and LI-F06b

| | Compound 4A = LI-F06a | | Compound 4B = LI-F06b | | |
|---|---|---|---|---|---|
| Pos. | $\delta_H$ | $\delta_C$ | Pos. | $\delta_H$ | $\delta_C$ |
| Thr1 | | | Thr1 | | |
| NH | 8.31 (br) | — | NH | 7.59 (br s) | — |
| 1 | — | 168.5 | 1 | — | 168.4 |
| 2 | 4.40 (m) | 56.9 | 2 | 4.44 (m) | 56.7 |
| 3 | 5.30 (m) | 70.5 | 3 | 5.32 (m) | 70.3 |
| 4 | 1.14 (m) | 16.6 | 4 | 1.15 (m) | 16.6 |
| Ala | | | Ala | | |
| NH | nf | — | NH | 7.53 (br s) | — |
| 1 | — | 170.6 | 1 | — | 170.7 |
| 2 | 3.97 (m) | 47.9 | 2 | 4.07 (m) | 48.0 |
| 3 | 1.15 (overlapped) | 17.3 | 3 | 1.21 (d, 7.3) | 17.4 |
| Asn | | | Gln | | |
| NH | 8.06 (br) | — | NH | 7.96 (br s) | — |
| 1 | — | 169.8 | 1 | — | 170.7 |
| 2 | 4.28 (m) | 50.5 | 2 | 3.93 (m) | 52.9 |
| 3 | 2.55 (m), 2.75 (dd, 6.7, 15.1) | 36.9 | 3 | 1.97 (m), 2.10 (m) | 26.5 |
| 4 | — | 172.6 | 4 | 2.12 (m), 2.21 (m) | 32.0 |
| 5 | — | — | 5 | — | 174.4 |
| NH$_2$ | nf | — | NH$_2$ | 6.88 (br s), 7.33 (br s) | — |
| Thr2 | | | Thr2 | | |
| NH | 8.54 (br) | — | NH | 8.48 (br) | — |
| 1 | — | 170.4 | 1 | — | 170.6 |
| 2 | 3.91 (m) | 60.5 | 2 | 4.02 (m) | 59.7 |
| 3 | 3.92 (m) | 65.6 | 3 | 3.99 (m) | 65.7 |
| 4 | 1.09 (d, 6.4) | 19.6 | 4 | 1.08 (d, 6.4) | 19.8 |
| Val | | | Val | | |
| NH | 7.28 (m) | — | NH | 7.39 (m) | — |
| 1 | — | nf | 1 | — | 171.0 |
| 2 | 4.40 (overlapped) | 57.3 | 2 | 4.39 (m) | 57.0 |
| 3 | 1.83 (overlapped) | 32.0 | 3 | 1.83 (m) | 31.6 |

TABLE 15-continued $^1$H (DMSO-$d_6$, 600 MHz) and $^{13}$C-NMR (DMSO-$d_6$, 150 MHz) data of compounds 4A and 4B.
Compounds 4 = LI-F06a and LI-F06b

| Compound 4A = LI-F06a | | | Compound 4B = LI-F06b | | |
|---|---|---|---|---|---|
| Pos. | $\delta_H$ | $\delta_C$ | Pos. | $\delta_H$ | $\delta_C$ |
| 4 | 0.75 (d, 6.6) | 18.1 | 4 | 0.74 (d, 6.6) | 18.4 |
| 5 | 0.84 (overlapped) | 19.3 | 5 | 0.80 (overlapped) | 19.2 |
| Ile | | | Ile | | |
| NH | 7.31 (overlapped) | — | NH | 7.23 (overlapped) | — |
| 1 | — | nf | 1 | — | 171.2 |
| 2 | 4.51 (overlapped) | 55.5 | 2 | 4.51 (1H, m) | 55.6 |
| 3 | 1.65 (overlapped) | 38.1 | 3 | 1.65 (m) | 38.1 |
| 4 | 1.02 (m), 1.36 (m) | 25.4 | 4 | 1.02 (m), 1.36 (m) | 25.5 |
| 5 | 0.82 (overlapped) | 15.6 | 5 | 0.82 (overlapped) | 15.6 |
| 6 | 0.72 (overlapped) | 14.4 | 6 | 0.71 (overlapped) | 14.3 |
| FA | | | FA | | |
| 1 | — | 172.1 | 1 | — | 172.2 |
| 2 | 2.44 (dd) | 43.1 | 2 | 2.37 (m) | 43.4 |
| 3 | 3.81 (m) | 67.7 | 3 | 3.78 (m) | 67.7 |
| 4 | 1.37 (overlapped) | 36.9 | 4 | 1.37 (m) | 36.9 |
| 5-12 | 1.22-1.24 (br s) | 29.1-29.2 | 5 | 1.22-1.24 (br s) | 29.1-29.2 |
| 13 | 1.25 (br s) | 26.4 | 13 | 1.25 (br s) | 26.2 |
| 14 | 1.43 (m) | 28.5 | 14 | 1.43 (m) | 28.5 |
| 15 | 3.03 (q, 6.7) | 40.7 | 15 | 3.03 (q, 6.7) | 40.7 |
| Gu | | | Gu | | |
| NH | nf | — | NH | 8.34 (br s) | — |
| 16 | — | 157.2 | 16 | — | 157.2 |

TABLE 16

$^1$H (DMSO-$d_6$, 600 MHz) and $^{13}$C-NMR (DMSO-$d_6$, 150 MHz) data of compounds 5A and 5B.
Compounds 5 = fusaricidins A and B, LI-F04a and LI-F04b

| Compound 5A = fusaricidin A | | | Compound 5B = fusaricidin B | | |
|---|---|---|---|---|---|
| Pos. | $\delta_H$ | $\delta_C$ | Pos. | $\delta_H$ | $\delta_C$ |
| Thr1 | | | Thr1 | | |
| NH | 7.66 (br) | — | NH | 8.30 (d, 8.0) | — |
| 1 | — | 168.5 | 1 | — | 168.4 |
| 2 | 4.46 (m) | 56.6 | 2 | 4.40 (br d, 8.5) | 57.0 |
| 3 | 5.32 (m) | 70.4 | 3 | 5.31 (m) | 70.3 |
| 4 | 1.16 (overlapped) | 16.3 | 4 | 1.15 (d, 5.7) | 16.6 |
| Ala | | | Ala | | |
| NH | 7.26 (br) | — | NH | 7.53 (br s) | — |
| 1 | — | 170.6 | 1 | — | 170.6 |
| 2 | 4.00 (m) | 47.8 | 2 | 4.10 (m) | 47.9 |
| 3 | 1.15 (overlapped) | 17.4 | 3 | 1.20 (d, 7.2) | 17.5 |
| Asn | | | Gln | | |
| NH | 8.10 (br) | — | NH | 8.53 (d, 4.3) | — |
| 1 | — | 169.8 | 1 | — | 170.6 |
| 2 | 4.28 (q, 6.6) | 50.5 | 2 | 3.92 (m) | 52.9 |
| 3 | 2.53 (m), 2.76 (dd, 6.6, 15.0) | 36.7 | 3 | 1.98 (m), 2.09 (m) | 26.4 |
| 4 | — | 172.5 | 4 | 2.10 (m), 2.20 (m) | 31.9 |
| 5 | — | — | 5 | — | 174.3 |
| NH$_2$ | nf | — | NH$_2$ | 6.86 (br s), 7.30 (br s) | — |
| Thr2 | | | Thr2 | | |
| NH | 8.54 (br s) | — | NH | 8.46 (d, 6.9) | — |
| 1 | — | nf | 1 | — | 170.5 |
| 2 | 3.91 (m) | 60.4 | 2 | 4.02 (m) | 59.7 |
| 3 | 3.91 (m) | 65.6 | 3 | 3.99 (m) | 65.5 |
| 4 | 1.09 (d, 5.6) | 19.6 | 4 | 1.07 (d, 6.0) | 19.9 |
| Val | | | Val | | |
| NH | nf | — | NH | 7.29 (br s) | — |
| 1 | — | nf | 1 | — | 171.2 |
| 2 | 4.40 (m) | 57.1 | 2 | 4.40 (m) | 57.1 |
| 3 | 1.82 (m) | 31.4 | 3 | 1.82 (m) | 31.5 |
| 4 | nf | nf | 4 | 0.76 (d, 6.6) | 18.4 |
| 5 | 0.82 (d, 6.0) | 19.1 | 5 | 0.81 (d, 6.2) | 19.1 |

TABLE 16-continued $^1$H (DMSO-$d_6$, 600 MHz) and $^{13}$C-NMR (DMSO-$d_6$, 150 MHz) data of compounds 5A and 5B.
Compounds 5 = fusaricidins A and B, LI-F04a and LI-F04b

| | Compound 5A = fusaricidin A | | | Compound 5B = fusaricidin B | |
|---|---|---|---|---|---|
| Pos. | $\delta_H$ | $\delta_C$ | Pos. | $\delta_H$ | $\delta_C$ |
| Val | | | Val | | |
| NH | 8.41 (br s) | — | NH | 8.37 (d, 7.6) | — |
| 1 | — | 172.1 | 1 | — | 173.1 |
| 2 | 4.13 (m) | 58.3 | 2 | 4.23 (m) | 57.8 |
| 3 | 2.02 (m) | 29.7 | 3 | 1.99 (m) | 30.2 |
| 4 | 0.86 (d, 6.7) | 18.2 | 4 | 0.86 (d, 6.7) | 18.2 |
| 5 | 0.84 (7.0) | 19.3 | 5 | 0.84 (7.0) | 19.3 |
| FA | | | FA | | |
| 1 | — | 172.1 | 1 | — | 172.0 |
| 2 | 2.37 (br d, 5.8) | 43.4 | 2 | 2.34 (dd, 7.0, 13.5), 2.44 (dd, 4.9, 13.5) | 43.4 |
| 3 | 3.80 (m) | 67.6 | 3 | 3.80 (m) | 67.6 |
| 4 | 1.37 (m) | 36.9 | 4 | 1.37 (m) | 36.8 |
| 5-12 | 1.22-1.25 (br s) | 26.2-29.2 | 5-12 | 1.22-1.25 (br s) | 26.2-29.2 |
| 13 | 1.25 (br s) | 26.2 | 13 | 1.25 (br s) | 26.2 |
| 14 | 1.43 (m) | 28.7 | 14 | 1.43 (m) | 28.5 |
| 15 | 3.03 (q, 6.7) | 40.6 | 15 | 3.03 (q, 6.7) | 40.6 |
| Gu | | | Gu | | |
| NH | nf | — | NH | 8.47 (br s) | — |
| 16 | — | 157.2 | 16 | — | 157.2 |

No hydrolysis experiments were carried out to determine the configuration of the constituting amino acids.

Example 8—Metabolites Produced by *Paenibacillus* Strains

Example 8.1: Production of Metabolites by *Paenibacillus* Strains

The presence of fusaricidins in general and in particular of the known fusaricidins A, B, C, D, LI-F06a, LI-F06b and LI-F08b as well as the novel fusaricidin-type compounds 1A and 1B was determined for the *Paenibacillus* strains following the procedural steps which are described in Example 7.1 above.

TABLE 17

Fusaricidin-type metabolite production of the *Paenibacillus* strains.

| | Compound/Fusaricidin | | | | | | | |
|---|---|---|---|---|---|---|---|---|
| Strains | 1A | 1B | 2A 2B C D | 3 LI-F08b | 4A LI-F06a | 4B LI-F06b | 5A A | 5B B |
| Lu16774 | + | ++ | ++ ++ | ++ | − | − | ++ | ++ |
| Lu17007 | + | ++ | ++ ++ | ++ | + | ++ | ++ | ++ |
| Lu17015 | ++ | ++ | ++ ++ | ++ | ++ | ++ | ++ | ++ |
| BD-62 | − | − | − − | − | − | − | − | − |

Legend: −, compound not detectable; +, compound detectable; ++, compound detectable at higher amounts compared to scale +.

The whole culture broth of all of the novel *Paenibacillus* strains Lu16774, Lu17007 and Lu17015 contained at least one the fusaricidin-type metabolites identified in Example 7 (Table 17). None of these fusaricidin-type metabolites were detected in the whole culture broth of *P. peoriae* strain BD-62.

The whole culture broth of the novel *Paenibacillus* strains Lu16774, Lu17007 and Lu17015 all contained the novel fusaricidin-type compounds 1A and 1B. Further, the whole culture broth of the novel *Paenibacillus* strains Lu16774, Lu17007 and Lu17015 all contained the fusaricidins A, B, C and D as well as LI-F08b. In addition, the whole culture broth of the novel *Paenibacillus* strains Lu17007 and Lu17015 contained fusaricidins LI-F06a and LI-F06b.

Compounds 1A and 1 B were not detected in the whole culture broth of the closely related *P. peoriae* strain BD-62. Fusaricidins A, B, C and D, LI-F06a, LI-F06b and LI-F08b were also not in the whole culture broth of *P. peoriae* strain BD-62.

Example 9: Activity of Metabolites by *Paenibacillus* Strains Against Various Fungal Pathogens The compounds 1A and 1B, fusaricidin A, B and D and were obtained were used in the following experiments.

Fungal growth assays were performed in 96 well plates with spore suspension of the pathogen *Botrytis cinerea* (BOTRCI, in YBA [10 g Bacto peptone (Becton Dickinson 211677), 10 g yeast extract (Becton Dickinson 212750), 20 g sodium acetate, ad 1000 mL aqua bidest] or *Alternaria solani*(ALTESO, in YBG [10 g Bacto peptone (Becton Dickinson 211677), 10 g yeast extract (Becton Dickinson 212750),20 g glycerine 99%, ad 1000 mL aqua bidest]). Fusaricidins and compounds 1A and 1B were dissolved and diluted in DMSO. Different concentrations ranging from 60 µM down to 0.3 µM were pipetted into the microtiter plate. An aqueous suspension of $10^4$ spores/ml was added. The plates were incubated at about 18° C. Fungal growth was determined by measuring the optical density at 600 nm in a microplate reader 3 and 7 days after the inoculation of the spores and compared to the untreated control (DMSO). $IC_{50}$ (concentration [µM] of the respective metabolite required for 50% inhibition of fungal growth) has been determined thereafter.

Notably, the compounds 1A and 1B showed the highest antifungal efficacy with $IC_{50}$ values of 0.4-0.6 µM (Tab. 18).

TABLE 18

Antifungal growth inhibition of *Paenibacillus* metabolites $IC_{50}$ values

| Pathogen (Evaluation day) | Compound/Fusaricidin | | | | |
|---|---|---|---|---|---|
| | 1A | 1B | 2B Fus. D | 5A Fus. A | 5B Fus. B |
| | Fungal growth inhibition (IC50 [μM]) | | | | |
| ALTESO (3 d) | 0.6 | 0.6 | 1.1 | 1.3 | 1.1 |
| ALTESO (7 d) | 0.5 | 0.4 | 0.6 | 0.7 | 0.6 |
| BOTRCI (7 d) | 0.3 | 0.4 | 0.5 | 0.5 | 0.6 |

"—" means that growth inhibition in tested concentration range not sufficient to determine $IC_{50}$.

In addition, glasshouse trials were performed with Compounds 1A and 1B as described in the Use Examples 5.1 to 5.5 above for the respective pathogens *Botrytis cinerea* (BOTRCI), *Alternaria solani* (ALTESO), *Phytophthora infestans* (PHYTIN), *Phakopsora pachyrhizi* (PHAKPA) and *Fusarium graminearum* (GIBBZE). The extent of fungal attack on the leaves was visually assessed 5-7 days after inoculation.

Notably, compounds 1A and 1B were effective in controlling important fungal diseases on crop plants already at dose levels as low as 7.2 ppm and showed higher antifungal efficacy than Fusaricidin A, B and D (Tables 19 to 21).

TABLE 19

Antifungal efficacy of metabolites determined in planta.

| Metabolite tested | Conc. | % efficacy (% fungal attack) | | | | |
|---|---|---|---|---|---|---|
| | | BOTRCI | ALTESO | PHYTIN | PHAKPA | GIBBZE |
| Untreated | — | 0 (100) | 0 (100) | 0 (100) | 0 (100) | 0 (100) |
| Compound 1A | 360 ppm | 99 | | 100 | 95 | 49 |
| Compound 1A | 36 ppm | 97 | 74 | | | |
| Compound 1B | 360 ppm | 100 | | 100 | 97 | |
| Compound 1B | 36 ppm | 97 | | | | |

TABLE 20

Efficacy of metabolites against late blight on tomato caused by *Phytophthora* infestans with protective application.

| Metabolite tested | Conc. | % efficacy (% fungal attack) |
|---|---|---|
| Untreated | — | 0 (100) |
| Fusaricidin A | 7.2 ppm | 15 |
| Fusaricidin B | 7.2 ppm | 4 |
| Fusaricidin D | 7.2 ppm | 0 |
| Compound 1B | 7.2 ppm | 44 |

TABLE 21

Efficacy of metabolites against head blight on wheat caused by *Fusarium graminearum* with protective application.

| Metabolite tested | Conc. | % efficacy (% fungal attack) |
|---|---|---|
| Untreated | — | 0 (100) |
| Fusaricidin A | 360 ppm | 31 |
| Fusaricidin B | 360 ppm | 0 |
| Compound 1A | 360 ppm | 49 |

TABLE 22

Efficacy of metabolites against head blight on wheat caused by *Septoria tritici* with protective application.

| Metabolite tested | Conc. | % efficacy (% fungal attack) |
|---|---|---|
| Untreated | — | 0 (100) |
| Fusaricidin D | 360 ppm | 50 |
| Compound 1B | 360 ppm | 80 |

Example 10: Comparison of Activity of *Paenibacillus polymyxa* Nov. Ssp. *Plantarum* Strains Lu16674 and Lu17007 of According to the Invention with *Paenibacillus polymyxa* Nov. Ssp. *Plantarum* M-1 Against Various Pathogens in Glass House Trials Whole culture broth from 6 days old cultures of *Paenibacillus* strain Lu17007, Lu16674 and M1 was obtained according to Use Example 3 and used as in the experimental setup of Use Example 5.1 to 5.5. The glasshouse trials were performed as described in the Use Examples 5.1 to 5.5 above for the respective pathogens. The extent of fungal attack on the leaves was visually assessed 5-7 days after inoculation.

Notably, the *Paenibacillus* strains Lu16774 and Lu17007 were effective in controlling important fungal diseases on crop plants even at high dilution factors and showed higher antifungal efficacy than the closely related strain M-1 (Tables 22 to 27).

TABLE 22

| *Paenibacillus* strain | Dilution factor of whole culture broth | BOTRCI % efficacy (% fungal attack) |
|---|---|---|
| Untreated | | 0 (100) |
| Lu16674 | 1:10 | 95 |
| M-1 | 1:10 | 86 |
| Lu16674 | 1:50 | 76 |
| Lu17007 | 1:50 | 98 |
| M-1 | 1:50 | 51 |

TABLE 23

| *Paenibacillus* strain | Dilution factor of whole culture broth | BOTRCI % efficacy (% fungal attack) |
|---|---|---|
| Untreated | | 0 (100) |
| Lu17007 | undiluted | 92 |
| M-1 | undiluted | 87 |
| Lu17007 | 1:10 | 84 |
| M-1 | 1:10 | 53 |
| Lu17007 | 1:50 | 63 |
| M-1 | 1:50 | 32 |

TABLE 24

| Paenibacillus strain | Dilution factor of whole culture broth | ALTESO % efficacy (% fungal attack) |
|---|---|---|
| Untreated | | 0 (100) |
| Lu16674 | 1:10 | 77 |
| M-1 | 1:10 | 41 |

TABLE 25

| Paenibacillus strain | Dilution factor of whole culture broth | PHYTIN % efficacy (% fungal attack) |
|---|---|---|
| Untreated | | 0 (100) |
| Lu17007 | 1:10 | 83 |
| M-1 | 1:10 | 42 |
| Lu16674 | 1:50 | 13 |
| Lu17007 | 1:50 | 30 |
| M-1 | 1:50 | 0 |

TABLE 26

| Paenibacillus strain | Dilution factor of whole culture broth | PHAKPA % efficacy (% fungal attack) |
|---|---|---|
| Untreated | | 0 (100) |
| Lu17007 | undiluted | 94 |
| M-1 | Undiluted | 87 |

TABLE 27

| Paenibacillus strain | Dilution factor of whole culture broth | GIBBZE % efficacy (% fungal attack) |
|---|---|---|
| Untreated | | 0 (100) |
| Lu17007 | undiluted | 70 |
| M-1 | undiluted | 31 |
| Lu16674 | 1:50 | 52 |
| Lu17007 | 1:50 | 33 |
| M-1 | 1:50 | 24 |

The documents as cited herein are incorporated by reference.

BRIEF DESCRIPTION OF THE FIGURES

FIG. 9 shows the percentage identity of the complete 16S rDNA sequence of the *Paenibacillus* strains of the invention to related taxa after multiple sequence alignment.
Legend: * Strain numbers: 1=*Paenibacillus* strain Lu16774; 2=*Paenibacillus* strain Lu17015; 3=*Paenibacillus* strain Lu17007; 4=*Paenibacillus peoriae* NRRL BD-62; 5=*Paenibacillus americanus* M H21; 6=*Paenibacillus brasiliensis* PB172; 7=*Paenibacillus* campinasensis 324; 8=*Paenibacillus* chibensis JCM 9905; 9=*Paenibacillus glucanolyticus* DSM 5162; 10=*Paenibacillus* hunanensis FeL05; 11=*Paenibacillus* jamilae CECT 5266; 12=*Paenibacillus* kribbensis AM49; 13=*Paenibacillus lactis* MB 1871; 14=*Paenibacillus lautus* JCM 9073; 15=*Paenibacillus macerans* IAM 12467; 16=*Paenibacillus massiliensis* 2301065; 17=*Paenibacillus pabuli* HSCC 492; 18=*Paenibacillus peoriae* DSM 8320 (BD-57); 19=*Paenibacillus* pini 522; 20=*Paenibacillus polymyxa* IAM 13419; 21=*Paenibacillus puripatii* ES_MS17; 22=*Paenibacillus sediminis* GT-H3; 23=*Paenibacillus terrae* AM141; 24=*Paenibacillus terrigena* A35; 25=*Paenibacillus* timonensis 2301032; 26=*Paenibacillus turicensis* MOL722; 27=*Paenibacillus uliginis* N3/975; 28=*Cohnella thermotolerans* CCUG 47242. Strains 6 to 28 are type strains for the respective species.

Similarities of the novel strains with *Paenibacillus peoriae* (NRRL BD-62 and DSM 8320) have been marked in bold letters.

Figure 1:
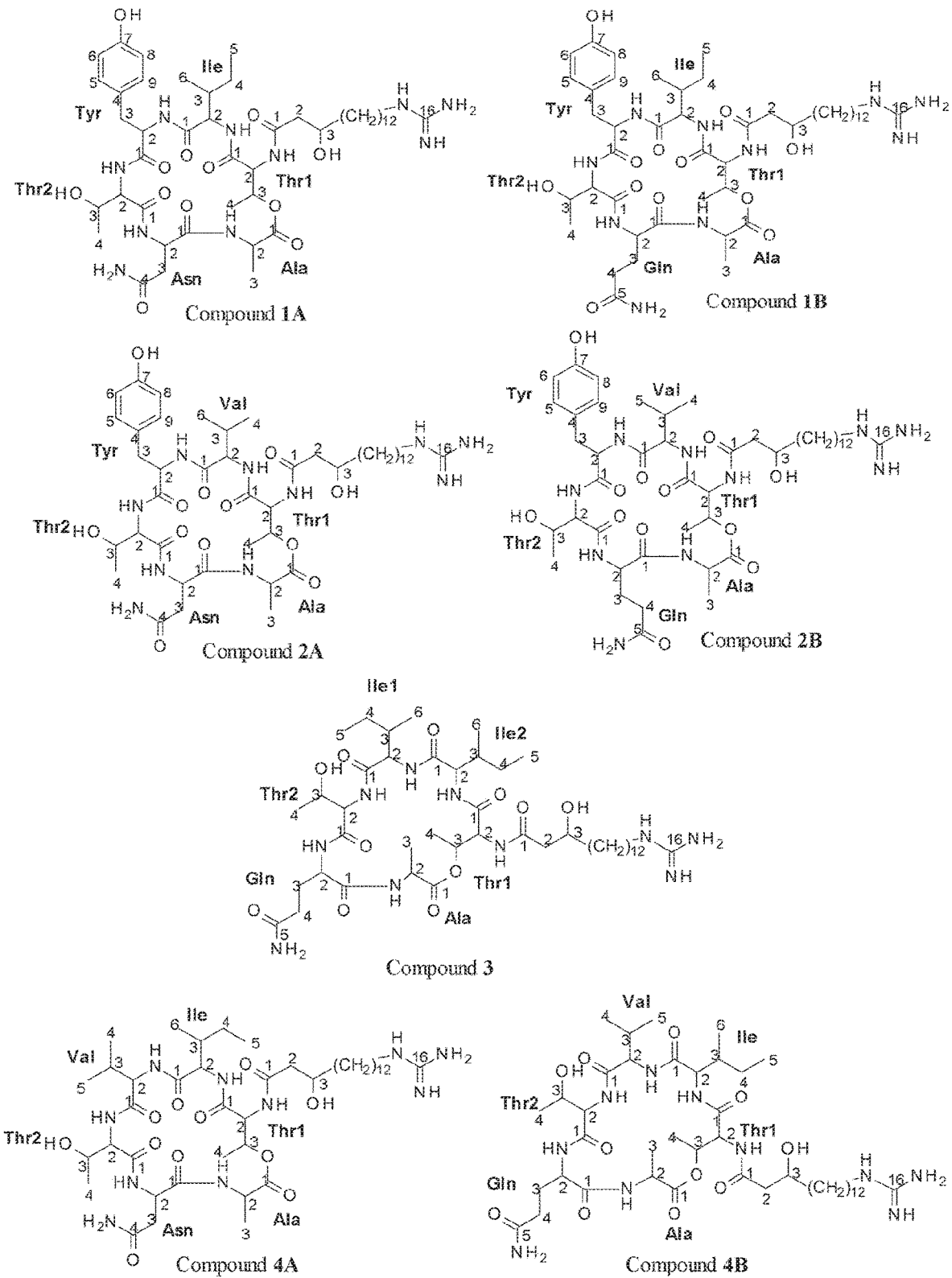
FIG. 1. Compounds 1A, 1B, 2A, 2B, 3, 4A, 4B, 5A and 5B.
Figure 1:
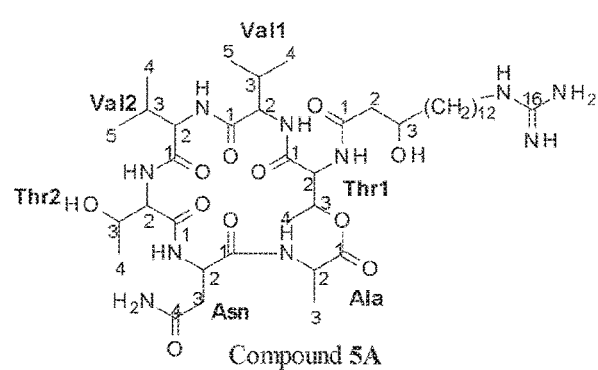
Figure 1:
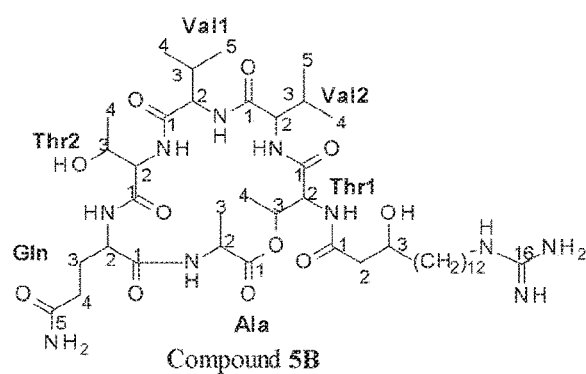
Figure 2:
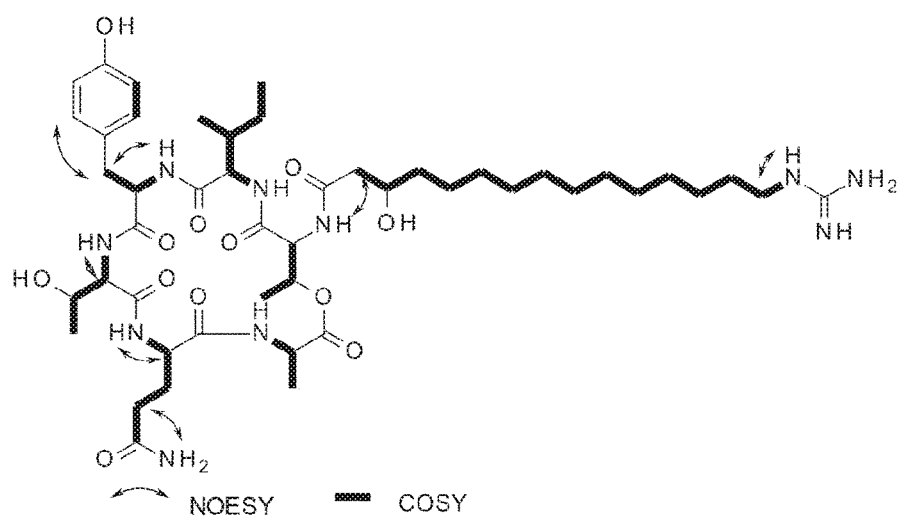
FIG. 2. Key NOESY and COSY correlations of compound 1B.
Figure 3:
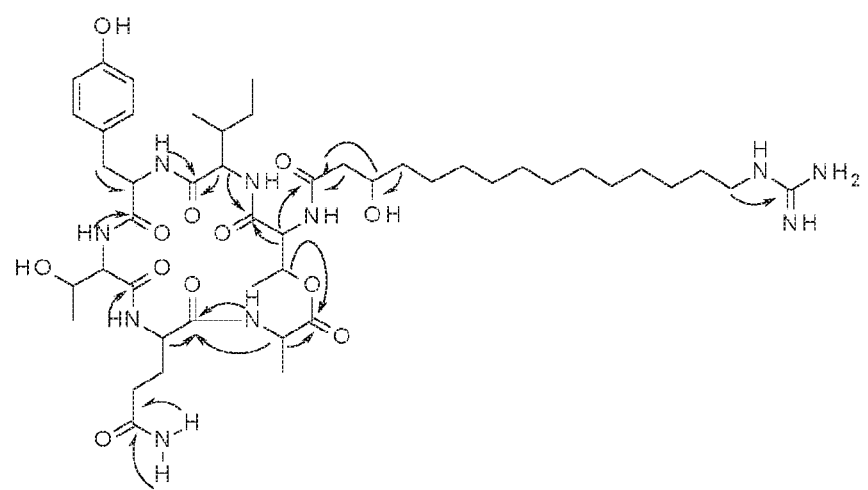
FIG. 3. HMBC correlation of compound 1B.
Figure 4:
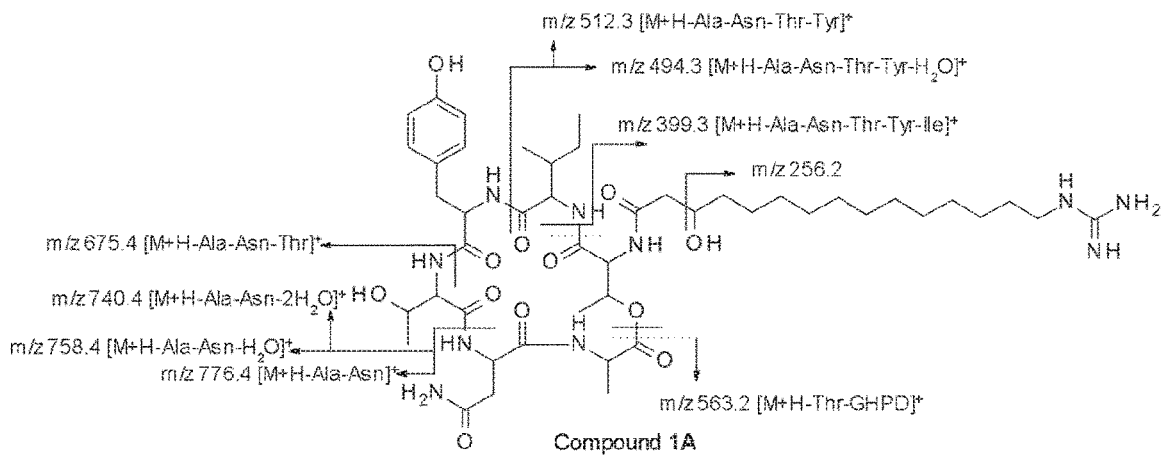
FIG. 4. Fragmentation patterns a) of compound 1A and b) of compound 1B.
Figure 4:
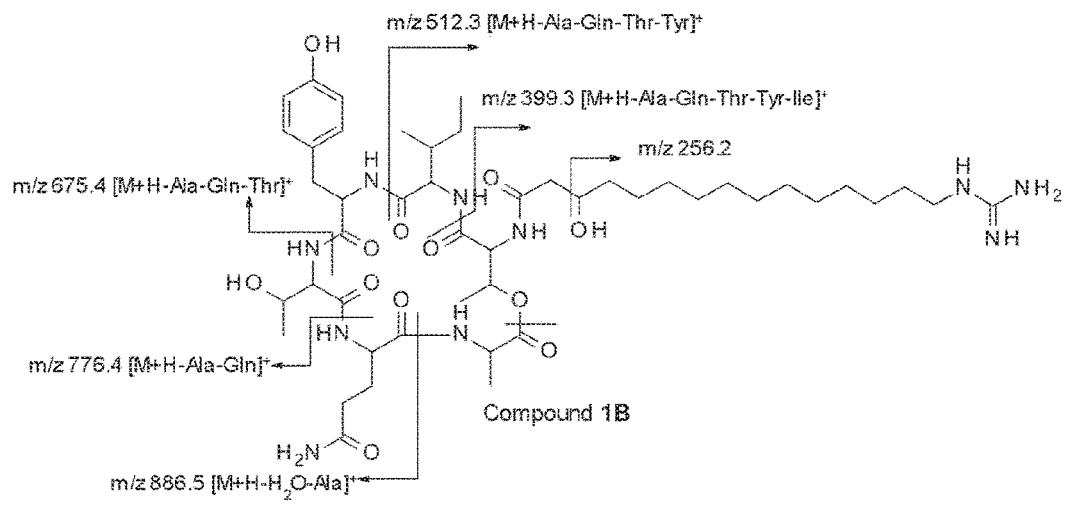
Figure 5:
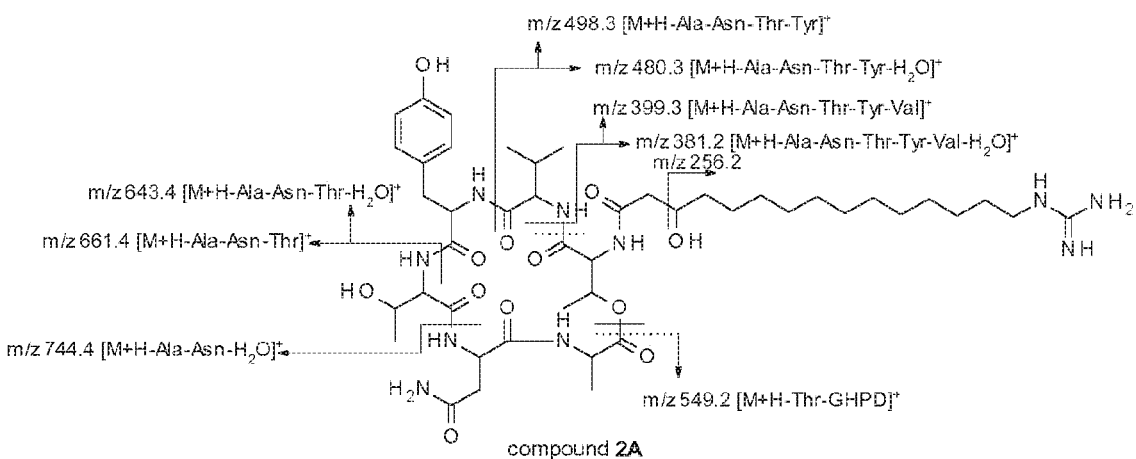
FIG. 5. Fragmentation patterns a) of compound 2A (fusaricidin C) and b) of compound 2B (fusaricidin D).
Figure 5:
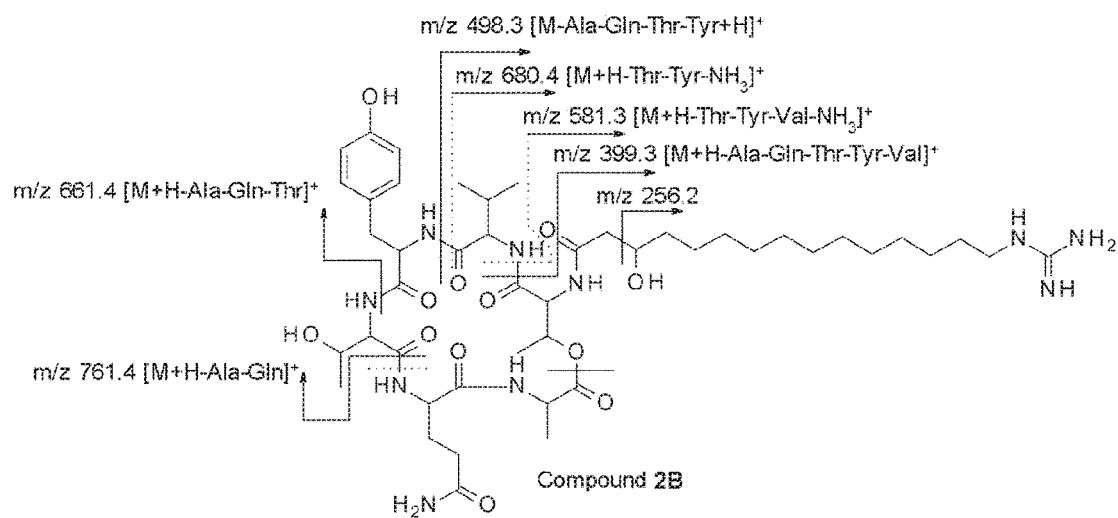
Figure 6:
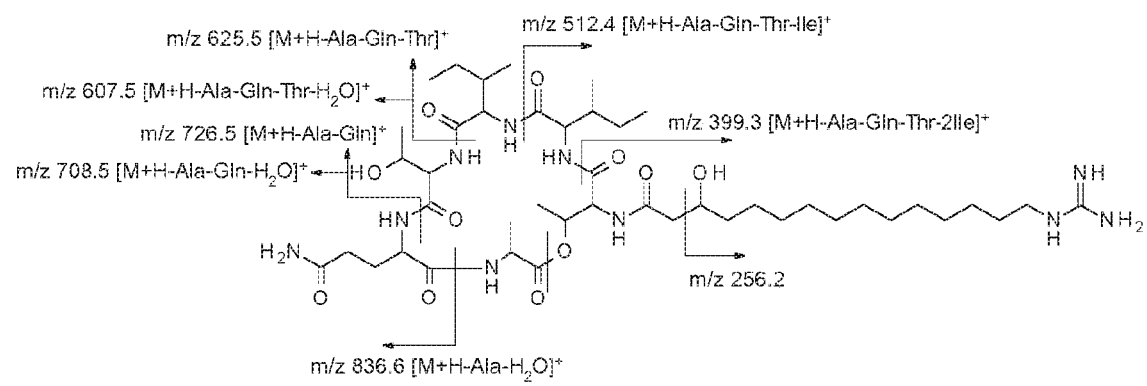
FIG. 6. Fragmentation pattern of compound 3 (LI-F08b).
Figure 7:
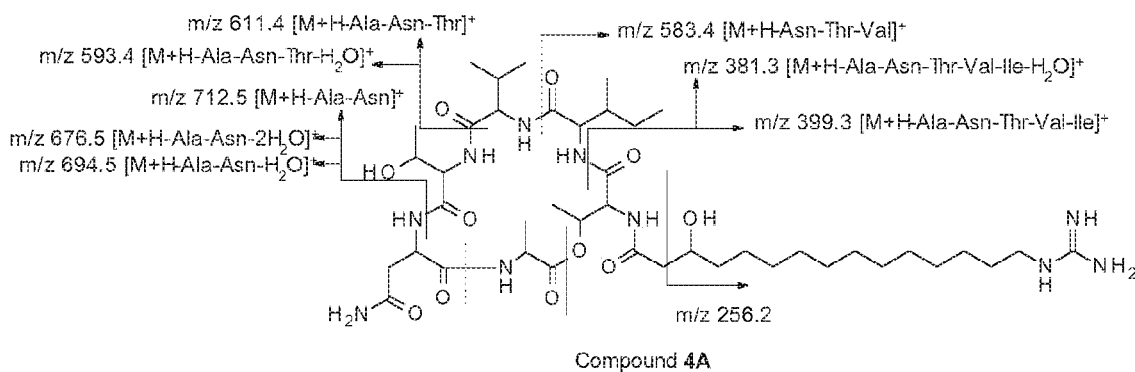
FIG. 7. Fragmentation patterns a) of compound 4A (LI-F06a) and b) of compound 4B (LI-F06b).
Figure 7:
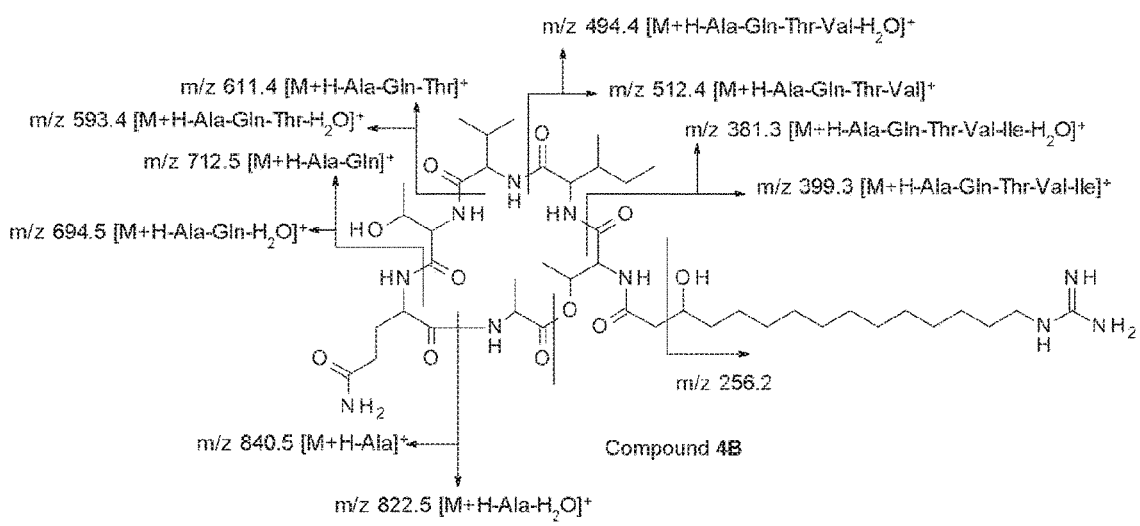
Figure 8:
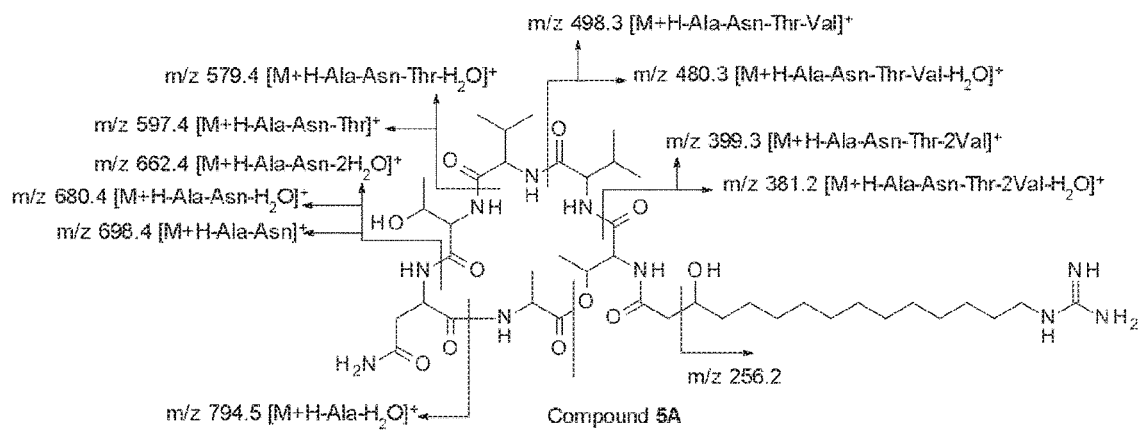
FIG. 8. Fragmentation patterns a) of compound 5A (fusaricidin A) and b) of compound 5B (fusaricidin B).
Figure 8:
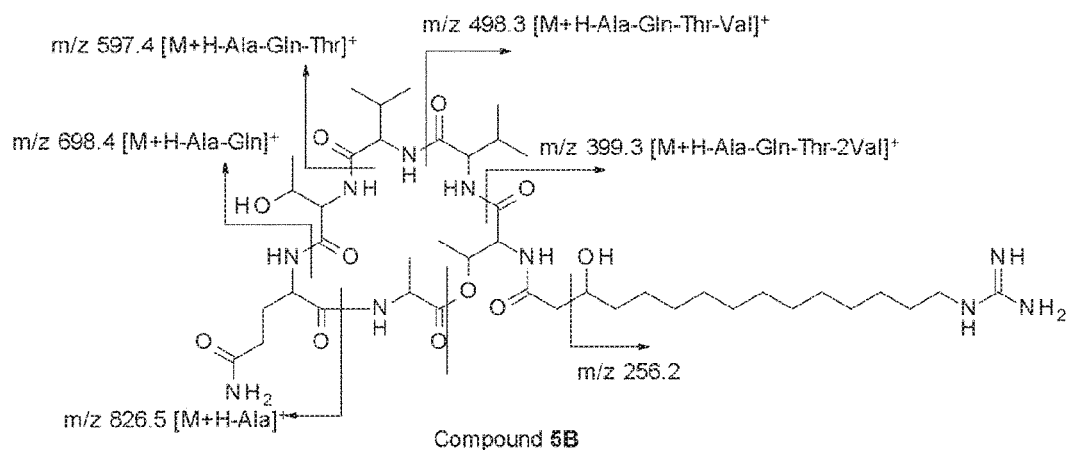
Figure 10:
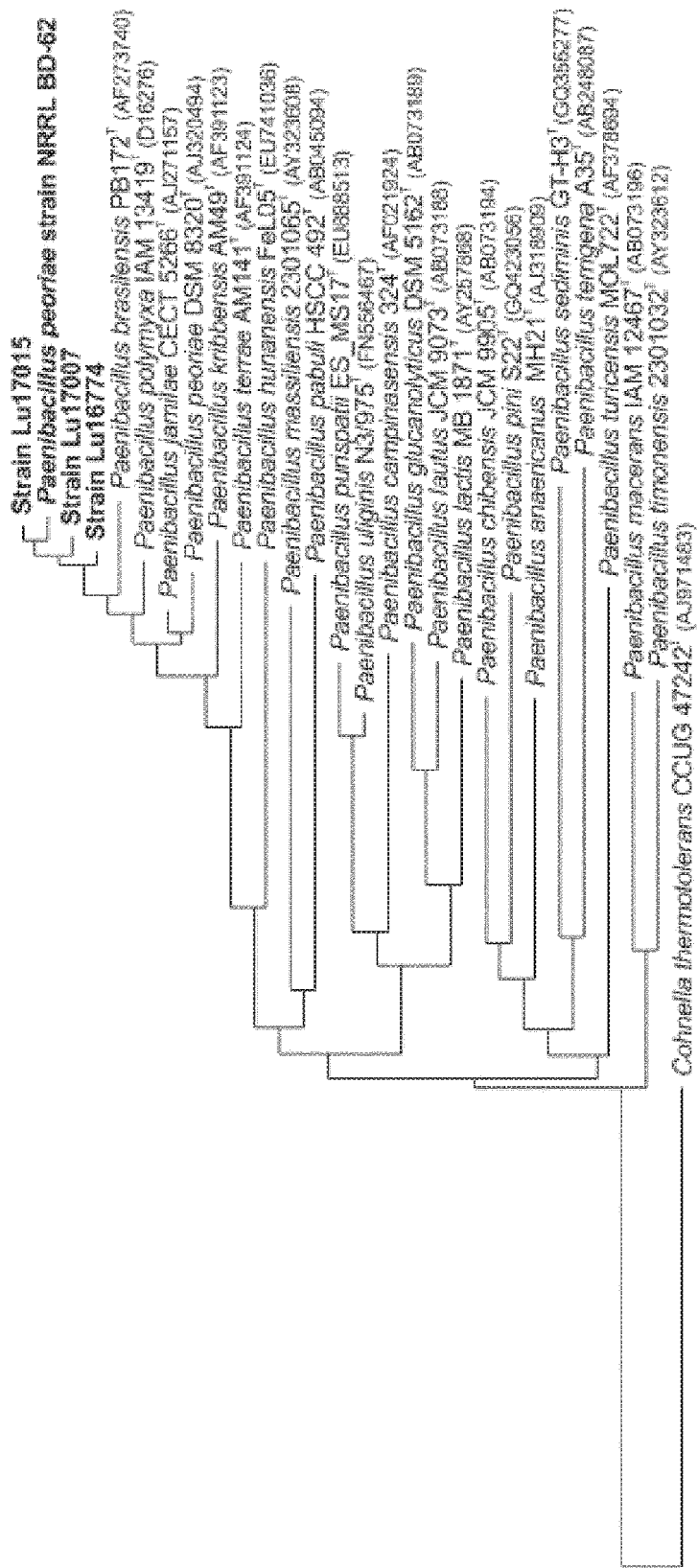

FIG. 10 shows a phylogenetic dendrogram calculated from the % identity of 16S-rDNA sequences of the *Paenibacillus* strains of the invention with other taxa (FIG. 9). The root of the tree was determined by including the 16S rRNA gene sequence of *Cohnella thermotolerans* into the analysis. The scale bar below the dendrogram indicates 1 nucleotide substitutions per 100 nucleotides.

Figure 11:
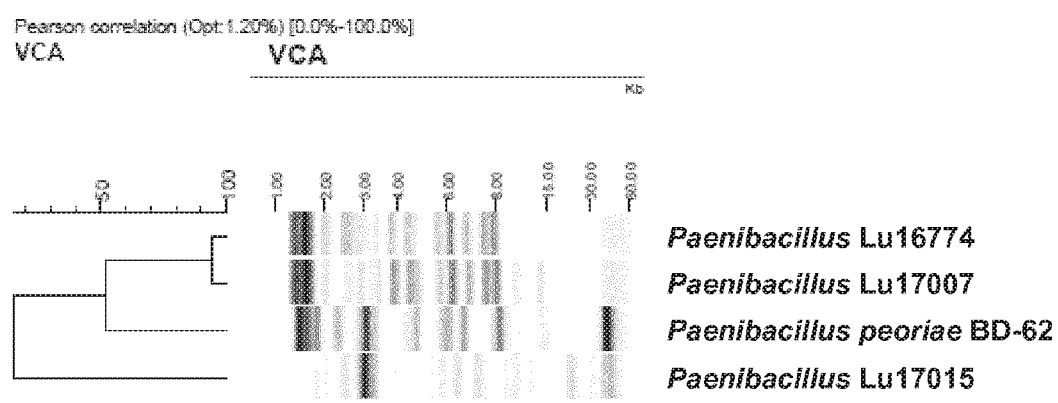

FIG. 11 shows the RiboPrint pattern obtained from samples of the *Paenibacillus* strains of the invention in comparison to a sample of the closely related *P. peoriae* strain BD-62 using RiboPrinter Microbial Characterization System and a phylogenetic dendrogram resulting therefrom.

FIG. 12 shows the percentage identity of the DNA sequence of the dnaN gene of the *Paenibacillus* strains of the invention to related *Paenibacillus* strains after multiple sequence alignment.
Legend: * Strain numbers: 1=*Paenibacillus* strain Lu16774; 2=*Paenibacillus* strain Lu17007; 3=*Paenibacillus* strain Lu17015; 4=*P. peoriae* DSM 8320$^T$=KCTC 3763$^T$ (GenBank acc. no. AGFX00000000; J. Bacteriol. 194, 1237-1238, 2012); 5=*P. polymyxa* 1-43 (GenBank acc. no. ASRZ01000000; deposition no. GCMCC 4965; CN 102352332 B); 6=*P. polymyxa* A18 (GenBank acc. no JWJJ00000000.1; NCBI Project ID 225496); 7=*P. polymyxa* ATCC 842$^T$=DSM 36$^T$=KCTC 3858$^T$ (GenBank acc. no. AFOX00000000; J. Bacteriol. 193(18), 5026-5027, 2011); 8=*P. polymyxa* CF05 (GenBank acc. no. CP009909; Genome Announc 3(2):e00198-15. Doi:10.1128/genomeA.00198-15); 9=*P. polymyxa* CICC 10580 (GenBank acc. no. JNCB00000000; Genome Announc. 2(4):e00854-14. doi:10.1128/genomeA.00854-14); 10=*P. polymyxa* DSM 365 (GenBank acc. no. JMIQ00000000; J. Biotechnol. 195, 72-73, 2015); 11=*P. polymyxa* E681 (GenBank acc. no. CP000154; GenomeNet Ref Seq NC_014483.2; J. Bacteriol. 192(22), 6103-6104, 2010); 12=*P. polymyxa* M-1 (GenBank acc. no. HE577054.1; GenomeNet Ref Seq NC_017542.1); 13=*P. polymyxa* NRRL B-30509 (GenBank acc. no. JTHO00000000; Genome Announc. 2015 March-April; 3(2): e00372-15); 14=*P. polymyxa* SC2 (GenBank acc. no. CP002213; J. Bacteriol. 193 (1), 311-312, 2011); 15=*P. polymyxa* SQR-21 (GenBank acc. no. CP006872; GenomeNet Ref Seq NZ_CP006872.1; Genome Announc. 2014 March-April; 2(2): e00281-14); 16=*P. polymyxa* Sb3-1 (GenBank acc. no. CP010268; Genome Announc. 2015 March-April; 3(2): e00052-15); 17=*P. polymyxa* TD94 (GenBank acc. no. ASSA00000000); 17=*P. polymyxa* WLY78 (GenBank acc. no. ALJV00000000); *P. terrae* HPL-003 (GenBank acc. no. CP003107; NCBI Ref Seq NC_016641.1); *P. polymyxa* CR1 (GenBank acc. no. CP006941; Genome Announc. 2014 January-Feburary; 2(1): e01218-13).

FIG. 13 shows the percentage identity of the DNA sequence of the complete gyrB gene of the *Paenibacillus* strains of the invention to related *Paenibacillus* strains after multiple sequence alignment. Strain numbers are described in Legend to FIG. 12.

FIG. 14 shows the percentage identity of the DNA sequence of the complete recF gene of the *Paenibacillus* strains of the invention to related *Paenibacillus* strains after multiple sequence alignment. Strain numbers are described in Legend to FIG. 12.

FIG. 15 shows the percentage identity of the DNA sequence of the complete recN gene of the *Paenibacillus* strains of the invention to related *Paenibacillus* strains after multiple sequence alignment. Strain numbers are described in Legend to FIG. 12.

FIG. 16 shows the percentage identity of the DNA sequence of the complete rpoA gene of the *Paenibacillus* strains of the invention to related *Paenibacillus* strains after multiple sequence alignment. Strain numbers are described in Legend to FIG. 12.

Figure 17:
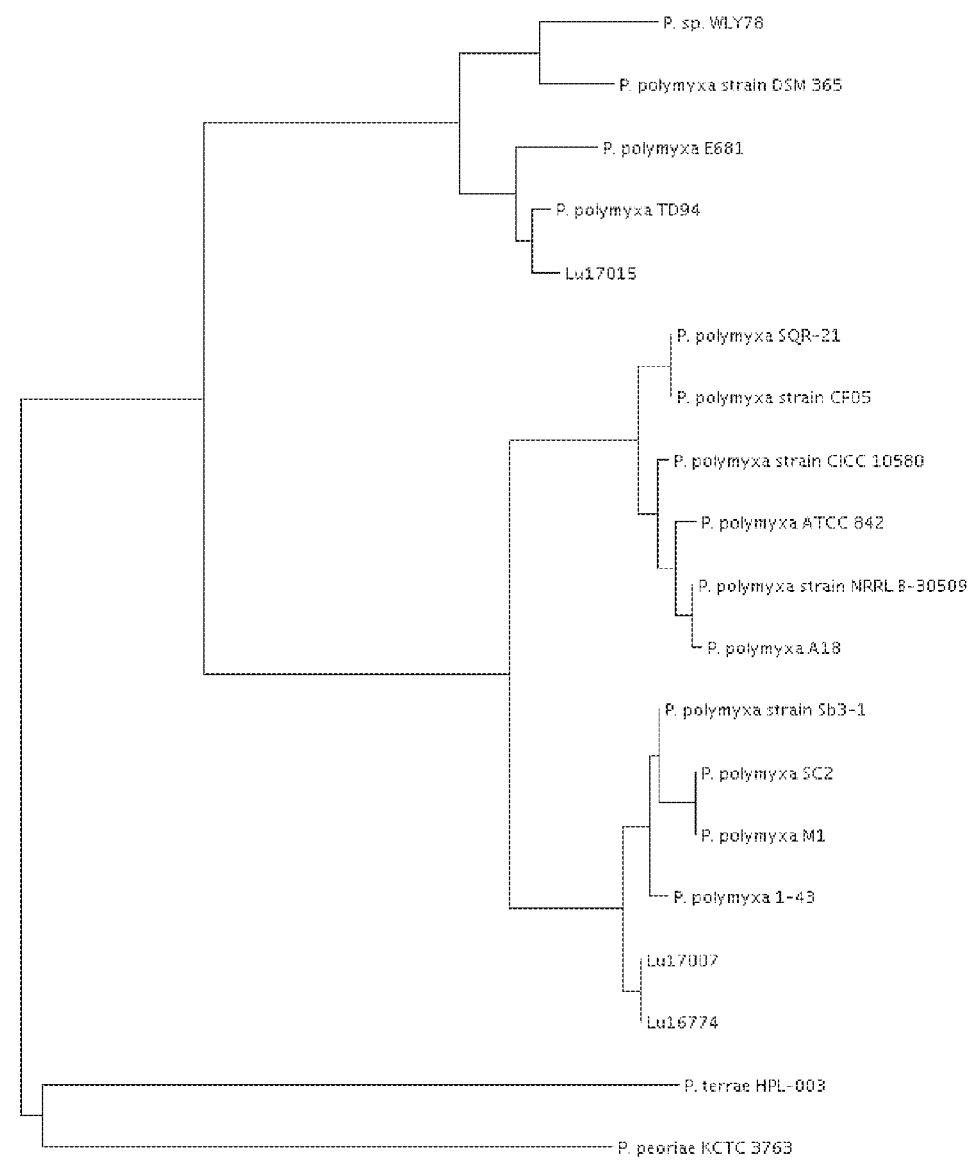

FIG. 17 shows the maximum likelihood denrogram on basis of the complete dnaN gene sequence of strains of the *P. polymyxa* complex. The scale of 0.1 shown corresponds to 1% nucleotide exchanges.

Figure 18:
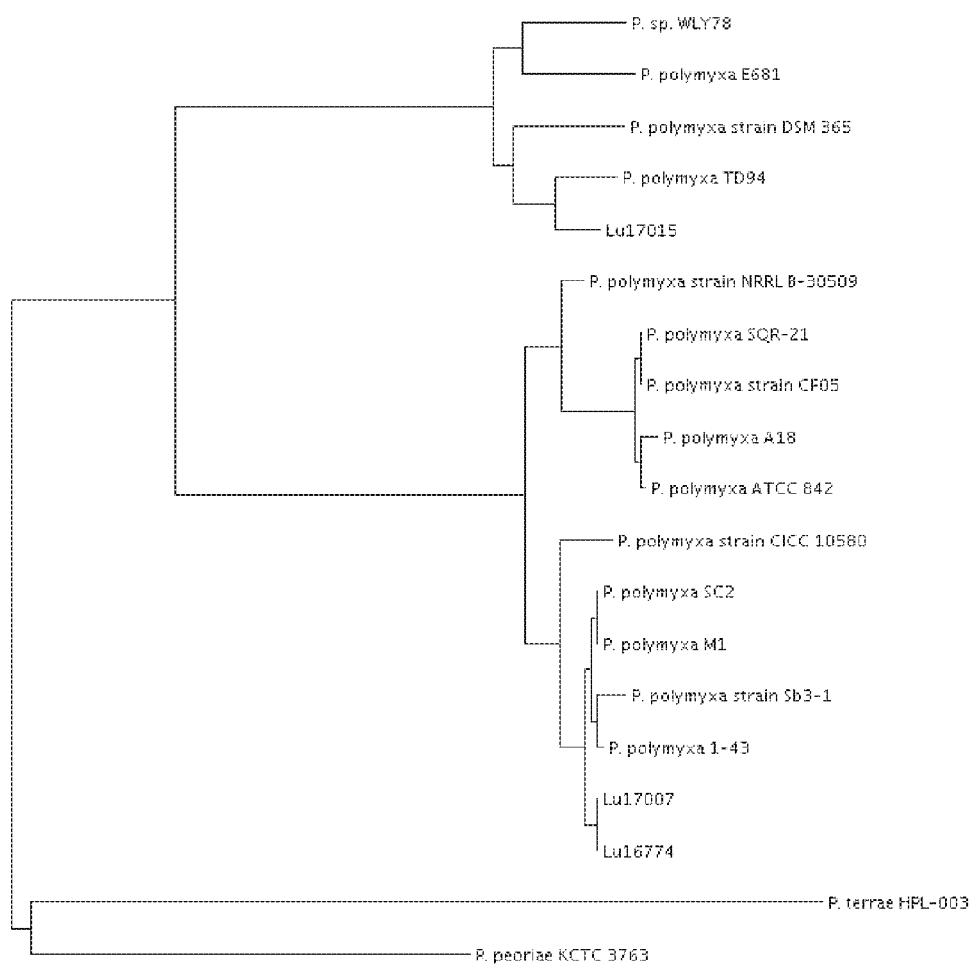

FIG. 18 shows the maximum likelihood denrogram on basis of the complete gyrB gene sequence of strains of the *P. polymyxa* complex. The scale of 0.1 shown corresponds to 1% nucleotide exchanges.

Figure 19:
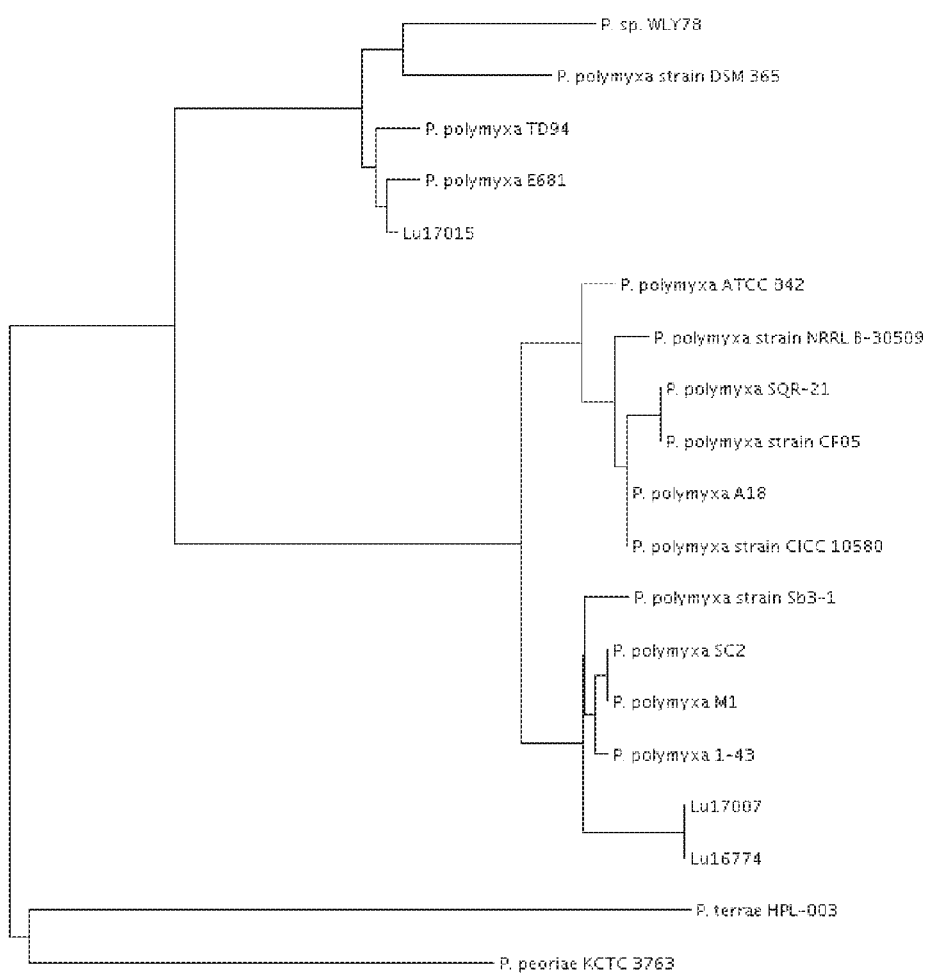

FIG. 19 shows the maximum likelihood denrogram on basis of the complete recF gene sequence of strains of the *P. polymyxa* complex. The scale of 0.1 shown corresponds to 1% nucleotide exchanges.

Figure 20:
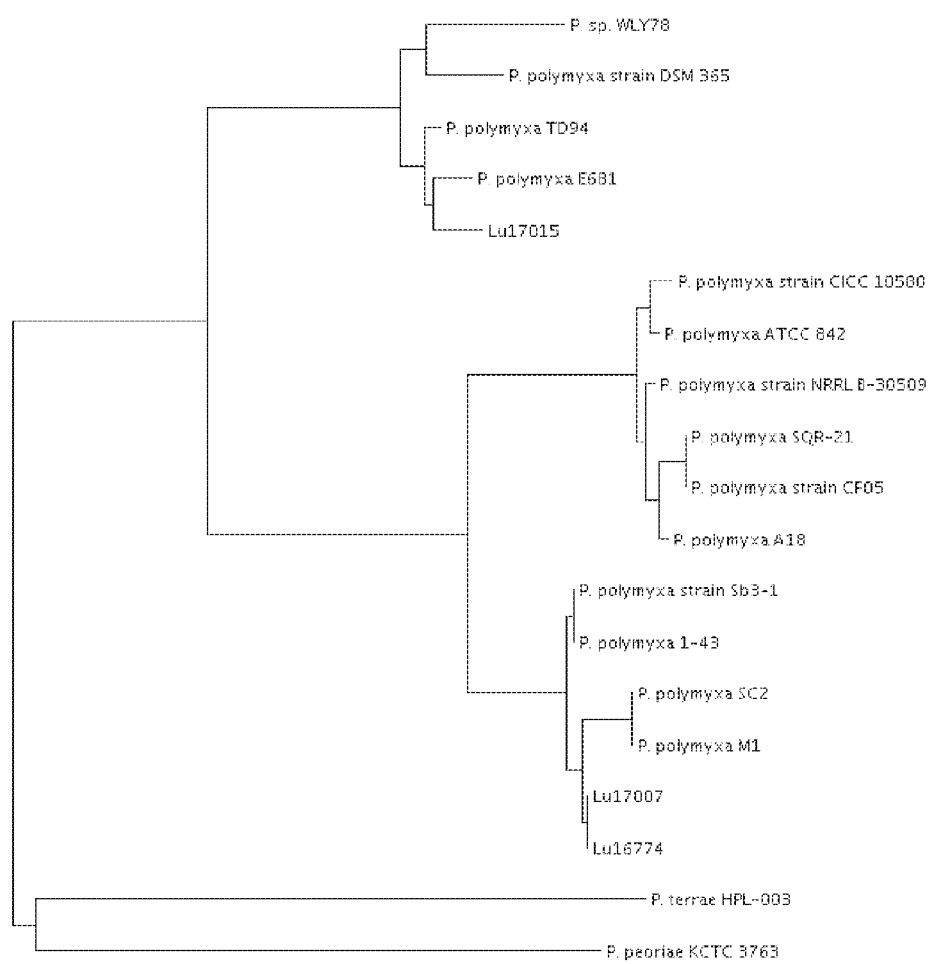

FIG. 20 shows the maximum likelihood denrogram on basis of the complete recN gene sequence of strains of the *P. polymyxa* complex. The scale of 0.1 shown corresponds to 1% nucleotide exchanges.

Figure 21:
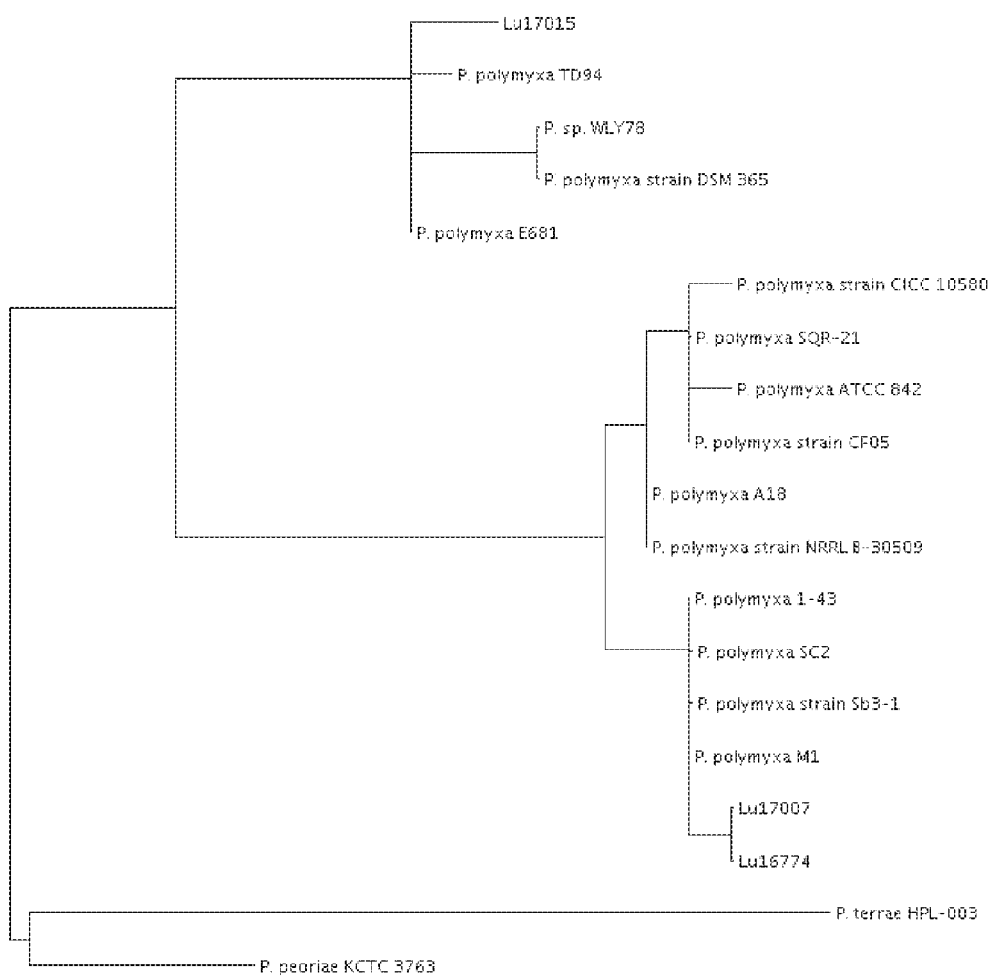

FIG. 21 shows the maximum likelihood denrogram on basis of the complete rpoA gene sequence of strains of the *P. polymyxa* complex. The scale of 0.1 shown corresponds to 1% nucleotide exchanges.

FIG. 22 shows the Amino Acid Index (AAI) matrix of representative genomes of the *P. polymyxa* complex performed according to Example 2.5. Strain numbers are described in Legend to FIG. 12.

The invention claimed is:

1. An agrochemical composition comprising:
   (1) a *Paenibacillus* strain, which is selected from the group consisting of:
      a) strain Lu16774 deposited with DSMZ under Accession No. DSM 26969;
      b) strain Lu17007 deposited with DSMZ under Accession No. DSM 26970;
      c) strain Lu17015 deposited with DSMZ under Accession No. DSM 26971;
   and
      d) a strain which comprises a DNA sequence exhibiting
         d1) at least 99.6% nucleotide sequence identity to the DNA sequences SEQ ID NO:4 or SEQ ID NO:9; or
         d2) at least 99.8% nucleotide sequence identity to the DNA sequence SEQ ID NO:14; or
         d3) at least 99.9% nucleotide sequence identity to the DNA sequences SEQ ID NO:5 or SEQ ID NO:10; or
         d4) at least 99.2% nucleotide sequence identity to the DNA sequence SEQ ID NO:15; or
         d5) at least 99.2% nucleotide sequence identity to the DNA sequences SEQ ID NO:6 or SEQ ID NO:11; or
         d6) at least 99.8% nucleotide sequence identity to the DNA sequence SEQ ID NO:16; or
         d7) at least 99.8% nucleotide sequence identity to the DNA sequences SEQ ID NO:7 or SEQ ID NO:12; or
         d8) at least 99.3% nucleotide sequence identity to the DNA sequence SEQ ID NO:17; or
         d9) 100.0% nucleotide sequence identity to the DNA sequences SEQ ID NO:8 or SEQ ID NO:13; or
         d10) 100% nucleotide sequence identity to the DNA sequence SEQ ID NO:18; and
   (2) at least one auxiliary selected from the group consisting of buffers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers, and binders.

2. The agrochemical composition of claim 1, wherein the *Paenibacillus* strain is selected from the group consisting of:
   a) strain Lu16774 deposited with DSMZ under Accession No. DSM 26969;
   b) strain Lu17007 deposited with DSMZ under Accession No. DSM 26970;
   c) strain Lu17015 deposited with DSMZ under Accession No. DSM 26971;
   and
   d) strains which comprise a DNA sequence exhibiting
      d1) at least 99.8% nucleotide sequence identity to any one of the DNA sequences SEQ ID NO:4, SEQ ID NO:9 and SEQ ID NO:14; or
      d2) 100.0% nucleotide sequence identity to any one of the DNA sequences SEQ ID NO:5, SEQ ID NO:10 and SEQ ID NO:15; or
      d3) exhibiting at least 99.8% nucleotide sequence identity to any one of the DNA sequences SEQ ID NO:6, SEQ ID NO:11 and SEQ ID NO:16; or
      d4) at least 99.8% nucleotide sequence identity to any one of the DNA sequences SEQ ID NO:7, SEQ ID NO:12 and SEQ ID NO:17; or
      d5) 100.0% nucleotide sequence identity to any one of the DNA sequences SEQ ID NO:8, SEQ ID NO:13 and SEQ ID NO:18.

3. The agrochemical composition of claim 1, wherein said *Paenibacillus* strain has antifungal activity against at least two of the plant pathogen selected from the group consisting of *Alternaria* spp., *Botrytis cinerea*, *Phytophthora infestans* and *Sclerotinia sclerotiorum*.

4. The agrochemical composition of claim 1, wherein said *Paenibacillus* strain produces at least one of the following compounds:

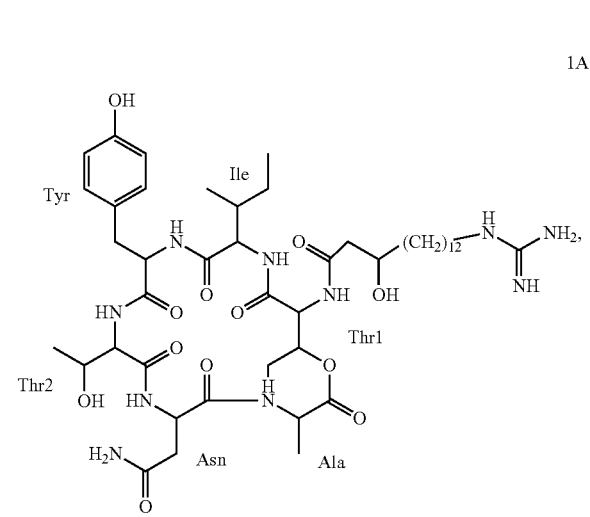

1A

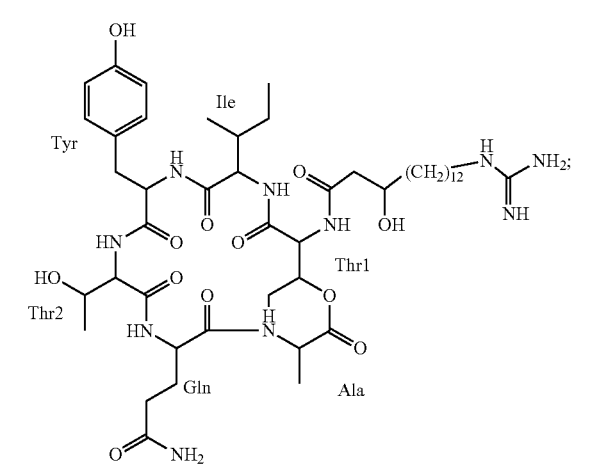

1B in a growth medium comprising at least one source of carbon and one source of nitrogen.

5. The agrochemical composition of claim 4, wherein said *Paenibacillus* strain is further capable of producing at least three compounds selected from the group consisting of fusaricidin A, fusaricidin B, fusaricidin C, fusaricidin D, LI-F06a, LI-F06b and LI-F08b.

6. The agrochemical composition of claim 1, wherein said *Paenibacillus* strain comprises at least one of the following compounds:

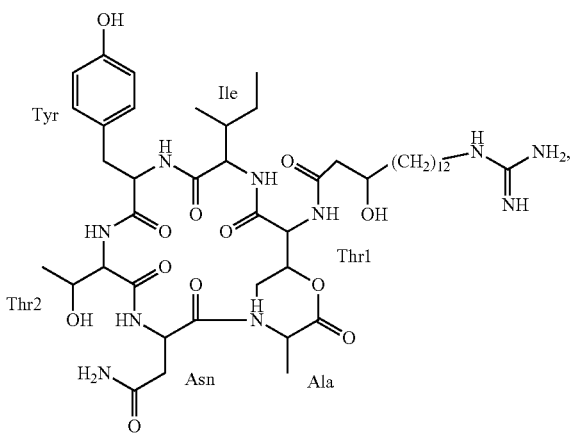

1A

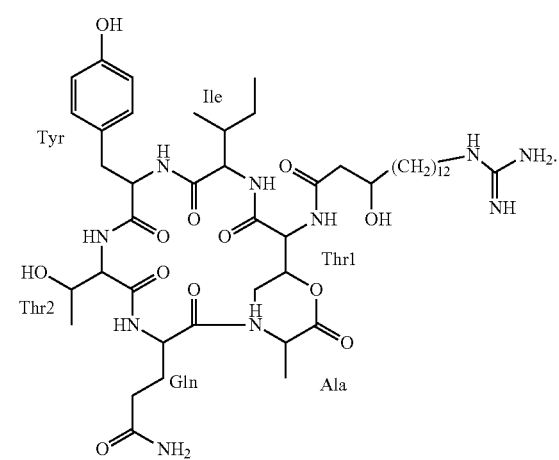

1B

7. The agrochemical composition of claim 6, wherein said *Paenibacillus* strain further comprises at least three compounds selected from the group consisting of fusaricidin A, fusaricidin B, fusaricidin C, fusaricidin D, LI-F06a, LI-F06b and LI-F08b.

8. The agrochemical composition of claim 1, wherein the *Paenibacillus* strain is in the form of a substantially purified culture of the *Paenibacillus* strain.

9. The agrochemical composition of claim 1, wherein the strain comprises between 0.01 and 95% by weight of the agrochemical composition.

10. The agrochemical composition of claim 1, wherein the auxiliary is a surfactant selected from the group consisting of anionic surfactants, cationic surfactants, nonionic surfactants, amphoteric surfactants, block polymers, and polyelectrolytes.

11. The agrochemical composition of claim 10, wherein the surfactant is used as an emusifier, a dispersant, a solubilizer, a wetter, a penetration enhancer, a protective colloid, or an adjuvant.

12. The agrochemical composition of claim 10, wherein the auxiliary is an anionic surfactant, and wherein the anionic surfactant is an ammonium salt of a sulfonate selected from the group consisting of alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates, and sulfosuccinamates.

13. The agrochemical composition of claim 10, wherein the auxiliary is a cationic surfactant selected from the group consisting of quaternary ammonium compounds with one or two hydrophobic groups and salts of long-chain primary amines.

14. The agrochemical composition of claim 10, wherein the auxiliary is a nonionic surfactant selected from the group consisting of alkoxylates, N-substituted fatty acid amides, amine oxides, esters, sugar-based surfactants, and polymeric surfactants.

15. The agrochemical composition of claim 10, wherein the auxiliary is an amphoteric surfactant selected from the group consisting of alkylbetains and imidazolines.

16. The agrochemical composition of claim 10, wherein the auxiliary is a block polymer are selected from the group consisting of block polymers of the A-B or A-B-A type comprising blocks of polyethylene oxide and polypropylene oxide and block polymers of the A-B-C type comprising alkanol, polyethylene oxide, and polypropylene oxide.

17. The agrochemical composition of claim 10, wherein the auxiliary is a polyelectrolyte, and wherein the polyelectrolyte is a polyacid or polybase selected from the group consisting of alkali salts of polyacrylic acid or polyacid comb polymers; polyvinyl amines; and polyethyleneamines.

* * * * *

SEQUENCE LISTING

```
<160> NUMBER OF SEQ ID NOS: 18

<210> SEQ ID NO 1
<211> LENGTH: 1539
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu16774 complete 16S rDNA
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
```

```
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1264)..(1264)
<223> OTHER INFORMATION: n is a, c, g, or t
<220> FEATURE:
<221> NAME/KEY: misc_feature
<222> LOCATION: (1457)..(1457)
<223> OTHER INFORMATION: n is a, c, g, or t

<400> SEQUENCE: 1
tttgatcctg gctcaggacg aacgctggcg gcgtgcntaa tacatgcaag tcgagcgngn      60
ttatntagaa gcttgcttct anaattncna gcggcggacg ggtgagtaac acgtaggcaa    120
cctgcccaca agacagggat aactaccgga aacggtagct aatacccgat acatcctttt    180
cctgcatggg agaaggagga aagncggagc aatctgtcac ttgtggatgg gcctgcggcg    240
cattagctag ttggtggggt aanggcctac caaggcgacg atgcgtagcc gacctgagag    300
ggtgatcggc cacactggga ctgagacacg gcccagactc ctacgggagg cagcagtagg    360
gaatcttccg caatgggcga aagcctgacg gagcaacgcc gcgtgagtga tgaaggtttt    420
cggatcgtaa agctctgttg ccagggaaga acgtcttgta gagtaactgc tacaagagtg    480
acggtacctg agaagaaagc cccggctaac tacgtgccag cagccgcggt aatacgtagg    540
gggcaagcgt tgtccggaat tattgggcgt aaagcgcgcg caggcggctc tttaagtctg    600
gtgtttaatc ccgaggctca acttcgggtc gcactggaaa ctggngagct tgagtgcaga    660
agaggagagt ggaattccac gtgtagcggt gaaatgcgta gagatgtgga ggaacaccag    720
tggcgaaggc gactctctgg gctgtaactg acgctgaggc gcgaaagcgt ggggagcaaa    780
caggattaga taccctggta gtccacgccg taaacgatga atgctaggtg ttaggggttt    840
cgataccctt ggtgccgaag ttaacacatt aagcattccg cctggggagt acggtcgcaa    900
gactgaaact caaaggaatt gacggggacc cgcacaagca gtggagtatg tggtttaatt    960
cgaagcaacg cgaagaacct taccaggtct tgacatccct ctgaccggtc tagagatagn   1020
cctttccttc gggacagagg agacaggtgg tgcatggttg tcgtcagctc gtgtcgtgag   1080
atgttgggtt aagtcccgca acgagcgcaa cccttatgct tagttgccag caggtcaagc   1140
tgggcactct aagcagactg ccggtgacaa accggaggaa ggtggggatg acgtcaaatc   1200
atcatgcccc ttatgacctg ggctacacac gtactacaat ggccggtaca acgggaagcg   1260
aagncgcgag gtggagccaa tcctagaaaa gccggtctca gttcggattg taggctgcaa   1320
ctcgcctaca tgaagtcgga attgctagta atcgcggatc agcatgccgc ggtgaatacg   1380
ttcccgggtc ttgtacacac cgcccgtcac accacgagag tttacaacac ccgaagtcgg   1440
tgaggtaacc gcaaggngcc agccgccgaa ggtggggtag atgattgggg tgaagtcgta   1500
acaaggtagc cgtatcggaa ggtgcggctg gatcacctc                          1539

<210> SEQ ID NO 2
<211> LENGTH: 1545
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu17007 complete 16S rDNA
```

```
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t

<400> SEQUENCE: 2
tttgatcctg gctcaggacg aacgctggcg gcgtgcctaa tacatgcaag tcgagcgngn      60
ttatntagaa gcttgcttct anataancta gcggcggacg ggtgagtaac acgtaggcaa     120
cctgcccaca agacagggat aactaccgga aacggtagct aataccccgat acatcctttt    180 cctgcatggg agaaggagga aagacggagc aatctgtcac ttgtggatgg gcctgcggcg    240
cattagctag ttggtggggt aawggcctac caaggcgacg atgcgtagcc gacctgagag    300
ggtgatcggc cacactggga ctgagacacg gcccagactc ctacgggagg cagcagtagg    360
gaatcttccg caatgggcga aagcctgacg gagcaacgcc gcgtgagtga tgaaggtttt    420
cggatcgtaa agctctgttg ccagggaaga acgtcttgta gagtaactgc tacaagagtg    480
acggtacctg agaagaaagc cccggctaac tacgtgccag cagccgcggt aatacgtagg    540
gggcaagcgt tgtccggaat tattgggcgt aaagcgcgcg caggcggctc tttaagtctg    600
gtgtttaatc ccgaggctca acttcgggtc gcactggaaa ctggngagct tgagtgcaga    660
agaggagagt ggaattccac gtgtagcggt gaaatgcgta gagatgtgga ggaacaccag    720
tggcgaaggc gactctctgg gctgtaactg acgctgaggc gcgaaagcgt ggggagcaaa    780
caggattaga taccctggta gtccacgccg taaacgatga atgctaggtg ttagggggttt    840 cgataccctt ggtgccgaag ttaacacatt aagcattccg cctggggagt acggtcgcaa    900
gactgaaact caaaggaatt gacggggacc cgcacaagca gtggagtatg tggtttaatt    960
cgaagcaacg cgaagaacct taccaggtct tgacatccct ctgaccggtc tagagatagn   1020
cctttccttc gggacagagg agacaggtgg tgcatggttg tcgtcagctc gtgtcgtgag    1080
atgttgggtt aagtcccgca acgagcgcaa cccttatgct tagttgccag caggtcaagc    1140
tgggcactct aagcagactg ccggtgacaa accggaggaa ggtggggatg acgtcaaatc    1200
atcatgcccc ttatgacctg gctacacacg tactacaat ggccggtaca acgggaagcg    1260
aagccgcgag gtggagccaa tcctagaaaa gccggtctca gttcggattg taggctgcaa    1320
ctcgcctaca tgaagtcgga attgctagta atcgcggatc agcatgccgc ggtgaatacg    1380
ttcccgggtc ttgtacacac cgcccgtcac accacgagag tttacaacac ccgaagtcgg    1440
```

```
tgaggtaacc gcaaggagcc agccgccgaa ggtggggtag atgattgggg tgaagtcgta    1500
acaaggtagc cgtatcggaa ggtgcggctg gatcacctcc tttct                   1545

<210> SEQ ID NO 3
<211> LENGTH: 1547
<212> TYPE: DNA
<213> ORGANISM: Paenibacillus epiphyticus
<220> FEATURE:
<221> NAME/KEY: misc_feature
<223> OTHER INFORMATION: Strain Lu17015 complete 16S rDNA
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (1024)..(1024)
<223> OTHER INFORMATION: n is a, c, g, or t

<400> SEQUENCE: 3
tgagtttgat cctggctcag gacgaacgct ggcggcgtgc ctaatacatg caagtcgagc     60
ggggttgntt agaagcttgc ttctaancaa cctagcggcg gacgggtgag taacacgtag    120
gcaacctgcc cacaagacag ggataactac cggaaacggt agctaatacc cgatacatcc    180
ttttcctgca tgggagaagg aggaaagacg gagcaatctg tcacttgtgg atgggcctgc    240
ggcgcattag ctagttggtg gggtaaaggc ctaccaaggc gacgatgcgt agccgacctg    300
agagggtgat cggccacact gggactgaga cacgcccag actcctacgg gaggcagcag    360
tagggaatct tccgcaatgg gcgaaagcct gacggagcaa cgccgcgtga gtgatgaagg    420
ttttcggatc gtaaagctct gttgccaggg aagaacgtct tgtagagtaa ctgctacaag    480
agtgacggta cctgagaaga aagccccggc taactacgtg ccagcagccg cggtaatacg    540 taggggggcaa gcgttgtccg gaattattgg gcgtaaagcg cgcgcaggcg gctctttaag    600
tctggtgttt aatcccgagg ctcaacttcg ggtcgcactg gaaactgggg agcttgagtg    660
cagaagagga gagtggaatt ccacgtgtag cggtgaaatg cgtagatatg tggaggaaca    720
ccagtggcga aggcgactct ctgggctgta actgacgctg aggcgcgaaa gcgtggggag    780
caaacaggat tagataccct ggtagtccac gccgtaaacg atgaatgcta ggtgttaggg    840
gtttcgatac ccttggtgcc gaagttaaca cattaagcat tccgcctggg gagtacggtc    900
gcaagactga aactcaaagg aattgacggg gacccgcaca agcagtggag tatgtggttt    960
aattcgaagc aacgcgaaga accttaccag gtcttgacat ccctctgacc ggtctagaga   1020 tagnccttc cttcgggaca gaggagacag gtggtgcatg gttgtcgtca gctcgtgtcg    1080
tgagatgttg ggttaagtcc cgcaacgagc gcaacccta tgcttagttg ccagcaggtc    1140
aagctgggca ctctaagcag actgccggtg acaaaccgga ggaaggtggg gatgacgtca    1200
aatcatcatg cccttatga cctgggctac acacgtacta caatggccgg tacaacggga    1260
agcgaaatcg cgaggtggag ccaatcctag aaaagccggt ctcagttcgg attgtaggct    1320
gcaactcgcc tacatgaagt cggaattgct agtaatcgcg gatcagcatg ccgcggtgaa    1380
tacgttcccg ggtcttgtac acaccgcccg tcacaccacg agagtttaca acacccgaag    1440
tcggtggggt aaccccgcaag ggagccagcc gccgaaggtg gggtagatga ttggggtgaa    1500
gtcgtaacaa ggtagccgta tcggaaggtg cggctggatc acctcct               1547
```

```
<210> SEQ ID NO 4
<211> LENGTH: 1143
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu16774 dnaN

<400> SEQUENCE: 4
atgaagatta gcattctgaa aaacgttttg aacgaggcca tacaacatgt atccaaagcg      60
atatccagtc gaacgacaat tccaattttg agtggtatta agctggatgt gaatcaccag     120
ggagtcacac tgaccgccag cgatacagac atctctattc aatcctttat tccgatggag     180
gatggtgacc aaacggtcgt tcagatcgaa caacccggca gtgtagtgct acccgctaaa     240
ttctttgtcg aaattatcaa aaagttgccg tctcaggaga tccgtatgga ggtaaaagac     300
caattccaaa cctttatctc atccggtgct actgaaattc agatcgttgg tttggaccct     360
gaagaatttc cggtgcttcc caacattgaa gaaaatcaag tgatctctgt gccaggtgat     420
ttgcttaaaa atatgattaa acagacgtta ttctccatct ctacccatga aacgacacct     480
attttgactg gtgtattgtg aatctggctg agggcgaatg gaaatttgt cgcaacggac      540 cgccaccgcc ttgccacccg cagcgctcat ttggagacgt ctgaaggctt gcgttttagc     600
aatgttgtca ttgcaggcaa aacgctcaat gagctgagca gaattattcc ggatcaaaat     660
atgcttgtgg atatcgtcgt agcggacaat caggtattat ttaaggtgga tcgcgtgtta     720
ttttactctc gcatcttgga cggcaccttat cctgatactt ctagaattat tccgacttcc     780
tacaaaacag aactgattgt ggacacaaaa agtttgagcg agtctattga ccgtgcttat     840
ttgctgtccc gtgaggaaaa aacgaatatt gtaaaaatgc aatcgttgga aaacggtgat     900
ctagagattt cctccagctc atctgaactt ggtaaagtgc gtgaggaagt aaatgtatcc     960
aaatttgagg gagagccact caaaatctcg ttcaactcca aatatatgct cgacgtgctg    1020
aaggtaattg acagcgagca gctgacgatt gcttttaccg gcattatgag ccccattatt    1080
ttaaaaccgg cagattccag caatgcgctg tatatcatcc tgccatatcg cacaaccaac    1140
tag                                                                  1143

<210> SEQ ID NO 5
<211> LENGTH: 1980
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu16774 gyrB

<400> SEQUENCE: 5
atggtcgaca aaatcgactt gtctgcggga gcttccggta cacagaacgg agcttcagaa      60
tatggcgcgg acgacattca agtgctcgaa gggcttgtgg cagttcgcaa acggccgggc     120
atgtacatcg ggagcaccag ttcttcggga ctgcatcatt tggtatggga aattgtagac     180
aacgcggtgg atgaacatct cgccaagttt tgctctcgca ttgatatcac aatgcataag     240
gacggttctg ttacagtatc agacaacggg cgcggtattc ctacgggaat gcacaaaatg     300
ggaattccta cgcctcaagt tgtattcacc attttgcacg ccggaggtaa gtttggcggt     360
tcgggatata aaaagtccgg gggtctgcat ggggtaggtg cgtctgtaac gaacgctctt     420
tcggaatggc ttgaagtgga aatctaccgg acggcaagaa ttcaccgtca gcggtttgaa     480
tattggcagg acaagaaggg cgtggagcat gtcggtgaac cgaccacagg ccttgaagtg     540
```

-continued

```
ctgggcaata ctaacaagac gggctcgaaa attacattta aaccggatat tcgcgttttt       600
cagtcaggaa ttcattttaa ctacgatacg ctggctgaac gccttcagga gattgctttt       660
ctgaattccg gccttcgtat tcagcttaaa gacgaacgca gcggaaagtc agatgaatat       720
ttttatgagg gtggagcaag tcagtttgtt tctttttttga atgagggtaa ggatgtactg      780
catgatgtta ttcactttaa tgccgagaaa gaagacattg aagtggagat tgccatccaa      840
tacaatgccg gctacacaga gacgattgct tcgttcgtta actccattcc gacacgtggc      900
gggggtacgc atgaaacagg cttcaaaacc gcttacactc gtatcatgaa cgactatgca      960
cgcaaaacag cgatgttgaa ggaaaaggat aaaaacctgg aaggtaacga tctgcgtgag     1020
ggtatgatgg ctgtaatcag tgtcaagatg gccgaggttg aatttgtcgg tcagacaaaa     1080
gatcagctgg gtagtgcttc ggcgcggagt acagtggatg ccatcgtatc tgaacaaatg     1140
cagcgctttt tggaggaaaa tccacagata gcgcaaacct tgatcagaaa ggcagttcaa     1200
gcatccaaag cgcgtgaagc tgcacgtaag gctcggacg aaatgcgttc tggcaagaaa       1260
cgcagtgaaa gttctaattt gaatggcaaa ctgtcgcctg cgcagtctaa ggattttaca     1320
cgtaatgagt tatttatcgt ggaaggcgat tcggctggag gatcggccaa acaaggacgg     1380
gattccaaaa tccaggcaat tttgccgtta agggcaagc cgatgaatcc ggaaaaatca      1440
aagttggcgg atattatgaa aaatgatgag tatcgtgcga ttacggcagc gattggcgcg     1500
ggggtaggaa ctgagttcac gctggaagac agcaattatt ccaaaatcat cattatgacc     1560
gatgcagata cagatggcgc gcacattcaa gtactgttgt tgacgttctt ttatcggtac     1620
atgaaagaac tcattgatgc aggacgcata tttattgctc agccgccatt gtataaaata     1680
acccgcaagt cgggtaagct cgaaacggtt cgttatgcct ggactgacga gcagcttgat     1740
aattacttaa agaatttggg acgaaatttt gagcttcaac gttataaagg actcggggag     1800
atgaaccctg atcagttatg ggaaacgaca tgaatcccg agtcacgcac cctgttgcgc      1860
gttcagattg aggatgctgc caaagctgaa cgccgtgtgt ccacattgat gggtgataag     1920
gtggatccac gtaagcgctg gatcgtggaa aacgtggatt tcacggaata cgtagagtag     1980
```

<210> SEQ ID NO 6
<211> LENGTH: 1116
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu16774 recF

<400> SEQUENCE: 6

```
gtgtttgtga acaacattgt tttgcagcag taccggaact ataaacagct ggagctgaat        60
gaattcgggc ccgttaattt gctgatcgga caaaatgcgc aaggcaaaac gaatctggtt       120
gaggcgattt ttgtattagc cttaactaaa agtcaccgaa cgtcccgtga caaggaatta      180
atttctttcg gggctacttc cacacatcta gctgctgatg tggataagaa atacgggaaa      240
atcagattgg atctctcgtt atccacacaa ggcaaaaaag caagatcaa cgggctagag       300
cagcgaaagc tgagcgattt tatcggttcg ttaaacgtgg tcatgtttgc gcccgaggat      360
ctggaaattg tcaaaggaac accgggggtt cgccgccggt ttcttgacat ggaaattgga     420
caagttgcgc aggatatttt gtatcatttg cagcaatatc agaaagtgct ggttcagcgg     480
aataaccctgc tcaagcaagc ttgggggaaa gatatgcgt ccgtgcagct gatgctggag      540
gtatggaatg agcaacttgt tgagcatggt gttaaaattg taaaaaagcg gaaacaattt      600
```

```
ataacaaagc tacaaaagtg ggcccaagcc attcatgaag ggattgcagg tgggacagaa      660
gagttaaaat tagcctatgt tccctctttc ggtgagccag aggaagaaga tgaagctgtc      720
ttattggagc gatttatgat aaagttatcc caaatgaggg aacaggaaat ccgccgtggc      780
atgactttgg cgggacccca tcgtgatgat ttggcctttg ccattaacgg cagagaagtg      840
catacgtatg gctctcaggg gcagcagcgg acgacggccc tgtctttgaa gctggccgaa      900
atagaattaa ttcatgagga aattgggag tatcctatcc tgctgctgga tgatgtattg        960
tccgagctgg accoctatcg tcagactcag ctgatcgaga ctttccaaag caaggtacag     1020
acctttatca cggcaaccgg gattgagacg ttgaacgcag aacgacttaa gggtgcccat     1080
atttatcacg tccacgacgg gcatgtggaa cactaa                               1116
```

<210> SEQ ID NO 7
<211> LENGTH: 1719
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu16774 recN

<400> SEQUENCE: 7

```
atgctggtca ctttgtctat acggaatttg gcagtcgtag aagctgtcga tgttcatttt       60
tataaaggat ttcatgtatt gagcggagaa actggtgctg gtaaatccat tattatcgac      120
gcacttgggc tgattgcggg cggcagggga tctgctgatc tagtgcgtta cggatgtgat      180
aaagccgaaa tggaagcctt gtttgaattg ccggtcaaac atcccgtttg gaatacgttg      240
gaggaacaag ggattaaggc taatccagaa gagcatttgc tgattcgtcg agaacttaca      300
gttcagggga aaagctcatc tcgaattaac ggtcagatgg ttaatttaac gatgctgcgt      360
gaggtaggtg agcaactcgt taatatccac gggcagcatg agcatcaaag cttgctgcgt      420
gcggatcgcc atcttgcgct gctggatacg ttcggtgact cggtcattgg tccagtcaaa      480
gcgctttacc gggagcgcta caatgctttt gtcaaagcgg aaaaagaagt aagagaattg      540
caaagctcca gtcaaaaggc ttatcagcta ttggacatgt atcgcttcca attggaagag      600
atcgctgcgc ggagttaaa attgggtgaa gatgaattat tggcagagga acgggtcaag      660
ctatcccata gtgagaaaat gatggatgga gtatcaggag catacgagct gttaagtggc      720
agaggtggtc tggatacggt caataacgtg ttgtccagat taatgatgt tcagagctac      780 gacagtaaaa gccttcagcc cattgcggag cagattcaat ctgctttcta tcagttggag      840
gatgcagcgt ttcaattacg ctcttatcgt gaggatattg aatttaatcc gggcaagctg      900
catgaggtgg agcaacgttt gaatcaaatt accgggttac agcgaaaata tggtgatagt      960
atagagcaga ttttggaata ctatagccgt attgagcagg aaaccgatct gttggaaaat     1020
aaagatgagc ggctggagca gctcattgca aagcggatg agttgctttc gaatttgctg     1080
gagattgctg aagagcttac agaggcacgt gaaatttgtg ctgaagagct tgcagagcaa     1140
gtagagcagg aattaaaaga tcttcaaatg gaaagaacgt cactcaaggt gcgtattgat     1200
ccaattgaag atccacgtgg atatgaatat aaaggtctaa aggtacgacc taccaagcaa     1260
gggatagata atgcggaatt tctgatttcg cccaatccag gtgagccact tcgcccactc     1320
ggtaaaatcg cttccggtgg tgagttatca cgtatcatgt tggcgatgaa aagtattttt     1380
gcgcgtcatg atcaaattcc ggtgctcatt tttgacgagg tggataccgg ggtaagtggt     1440
cgtgcagctc agtccatagc cgagaagctt tatcgtttgt cttccgtttg tcaggtgttt     1500
```

| | |
|---|---:|
| tccattactc atttgccgca ggtggcatgt atggcagatc atcagtacct gattgagaaa | 1560 |
| aatgttcatg acggacggac catgactcaa attgagggac taacggagga aggtcgtgtt | 1620 |
| aaggaattgg cacggatgct gggtggggta gaaattaccg aaaaaacatt gcatcacgca | 1680 |
| caggaaatgc tgaatttggc ggaaggaaag aaagcctga | 1719 |

```
<210> SEQ ID NO 8
<211> LENGTH: 945
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu16774 rpoA

<400> SEQUENCE: 8
```

| | |
|---|---:|
| gtgatagaaa tcgaaaagcc gaaaattgag acggttgacg tcaatgatga tggcacctat | 60 |
| ggaaaattcg tagtagaacc gctggaacgc ggatacggta cgacgcttgg gaactcgctt | 120 |
| cgccgtattc tgttatcctc gttaccgggg gcagcagtca catcggttca gatcgatggg | 180 |
| gttctgcacg agtttgcaac ggttcccggt gtgaaggaag acgtaacgga gatcattctg | 240 |
| aacttgaaag ctttatcgct aaaaatccac tcagatgaag agaaagtact tgaaatcgat | 300 |
| gcggaaggcg aaggagttgt aacggcaggt gatatccgtg cggatagtga tgtggaaatt | 360 |
| cttaatccgg atcttcacat tgcaacgctc ggacccgggtt cgagacttca catgcgtatt | 420 |
| tttgccaatc gcggtcgcgg ttacgttaag caggatcgga ataaacgtga tgaccagccg | 480 |
| atcggcgtca ttcccgtcga ctccatctac actccgattg cacgcgtgaa ctacggcgta | 540 |
| gaaaatacgc gtgtcggcca ggttacgaat tatgacaagc tgacacttga ggtttggact | 600 |
| gacggaacta ttcgtcctga agaagctgtg agccttggag ccaaaatttt gaccgagcat | 660 |
| gtgatgctat tcgtgggtct cacgacgatgaa gcaaaagatg cagaaattat ggtcgaaaaa | 720 |
| gaagaagaca aaaagaaaa agttcttgaa atgacgatcg aagagctgga tctctccgtc | 780 |
| cgttcctata actgccttaa gcgcgctggt atcaatacgg tacaagaact cacgactaaa | 840 |
| tctgaagaag atatgatgaa ggtccgtaac ttgggtcgca aatctttgga agaagtacaa | 900 |
| gagaagctcg aggaacttgg tttaggactt cgtacggaag aatag | 945 |

```
<210> SEQ ID NO 9
<211> LENGTH: 1143
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu17007 dnaN

<400> SEQUENCE: 9
```

| | |
|---|---:|
| atgaagatta gcattctgaa aaacgttttg aacgaggcca tacaacatgt atccaaagcg | 60 |
| atatccagtc gaacgacaat tccaattttg agtggtatta agctggatgt gaatcaccag | 120 |
| ggagtcacac tgaccgccag cgatacagac atctctattc aatcctttat tccgatggag | 180 |
| gatggtgacc aaacggtcgt tcagatcgaa caacccggca gtgtagtgct acccgctaaa | 240 |
| ttctttgtcg aaattatcaa aaagttgccg tctcaggaga tccgtatgga ggtaaaagac | 300 |
| caattccaaa cctttatctc atccggtgct actgaaattc agatcgttgg tttggaccct | 360 |
| gaagaatttc cggtgcttcc caacattgaa gaaaatcaag tgatctctgt gccaggtgat | 420 |
| ttgcttaaaa atatgattaa acagacggta ttctccatct ctacccatga aacgacacct | 480 |
| attttgactg gtgtattgtg gaatctggct gagggcgaat tgaaatttgt cgcaacggac | 540 |

| | | | |
|---|---|---|---|
| cgccaccgcc | ttgccacccg | cagcgctcat | ttggagacgt ctgaaggctt gcgttttagc | 600 |
| aatgttgtca | ttgcaggcaa | aacgctcaat | gagctgagca gaattattcc ggatcaaaat | 660 |
| atgcttgtgg | atatcgtcgt | agcggacaat | caggtattat ttaaggtgga tcgcgtgtta | 720 |
| ttttactctc | gcatcttgga | cggcaccat | cctgatactt ctagaattat tccgacttcc | 780 |
| tacaaaacag | aactgattgt | ggacacaaaa | agtttgagcg agtctattga ccgtgcttat | 840 |
| ttgctgtccc | gtgaggaaaa | aacgaatatt | gtaaaaatgc aatcgttgga aaacggtgat | 900 |
| ctagagattt | cctccagctc | atctgaactt | ggtaaagtgc gtgaggaagt aaatgtatcc | 960 |
| aaatttgagg | gagagccact | caaaatctcg | ttcaactcca aatatatgct cgacgtgctg | 1020 |
| aaggtaattg | acagcgagca | gctgacgatt | gcttttaccg gcattatgag ccccattatt | 1080 |
| ttaaaaccgg | cagattccag | caatgcgctg | tatatcatcc tgccatatcg cacaaccaac | 1140 |
| tag | | | | 1143 |

<210> SEQ ID NO 10
<211> LENGTH: 1980
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu17007 gyrB

<400> SEQUENCE: 10

| | | | |
|---|---|---|---|
| atggtcgaca | aaatcgactt | gtctgcggga | gcttccggta cacagaacgg agcttcagaa | 60 |
| tatggcgcgg | acgacattca | agtgctcgaa | gggcttgtgg cagttcgcaa acggccgggc | 120 |
| atgtacatcg | ggagcaccag | ttcttcggga | ctgcatcatt tggtatggga aattgtagac | 180 |
| aacgcggtgg | atgaacatct | cgccaagttt | tgctctcgca ttgatatcac aatgcataag | 240 |
| gacggttctg | ttacagtatc | agacaacggg | cgcggtattc ctacgggaat gcacaaaatg | 300 |
| ggaattccta | cgcctcaagt | tgtattcacc | attttgcacg ccggaggtaa gtttggcggt | 360 |
| tcgggatata | aaaagtccgg | gggtctgcat | ggggtaggtg cgtctgtaac gaacgctctt | 420 |
| tcggaatggc | ttgaagtgga | aatctaccgg | gacggcaaga ttcaccgtca gcggtttgaa | 480 |
| tattggcagg | acaagaaggg | cgtggagcat | gtcggtgaac cgaccacagg ccttgaagtg | 540 |
| ctgggcaata | ctaacaagac | gggctcgaaa | attacattta aaccggatat tcgcgttttt | 600 |
| cagtcaggaa | ttcattttaa | ctacgatacg | ctggctgaac gccttcagga gattgctttt | 660 |
| ctgaattccg | gccttcgtat | tcagcttaaa | gacgaacgca gcggaaagtc agatgaatat | 720 |
| ttttatgagg | gtggagcaag | tcagtttgtt | tctttttga atgagggtaa ggatgtactg | 780 |
| catgatgtta | ttcactttaa | tgccgagaaa | gaagacattg aagtggagat tgccatccaa | 840 |
| tacaatgccg | gctacacaga | gacgattgct | tcgttcgtta actccattcc gacacgtggc | 900 |
| ggggtacgc | atgaaacagg | cttcaaaacc | gcttacactc gtatcatgaa cgactatgca | 960 |
| cgcaaaacag | cgatgttgaa | ggaaaaggat | aaaaacctgg aaggtaacga tctgcgtgag | 1020 |
| ggtatgatgg | ctgtaatcag | tgtcaagatg | gccgaggttg aatttgtcgg tcagacaaaa | 1080 |
| gatcagctgg | gtagtgcttc | ggcgcggagt | acagtggatg ccatcgtatc tgaacaaatg | 1140 |
| cagcgctttt | tggaggaaaa | tccacagata | gcgcaaacct tgatcagaaa ggcagttcaa | 1200 |
| gcatccaaag | cgcgtgaagc | tgcacgtaag | gctcggacg aaatgcgttc tggcaagaaa | 1260 |
| cgcagtgaaa | gttctaattt | gaatggcaaa | ctgtcgcctg cgcagtctaa ggattttaca | 1320 |
| cgtaatgagt | tatttatcgt | ggaaggcgat | tcggctggag gatcggccaa acaaggacgg | 1380 |

| | |
|---|---|
| gattccaaaa tccaggcaat tttgccgtta aagggcaagc cgatgaatcc ggaaaaatca | 1440 |
| aagttggcgg atattatgaa aaatgatgag tatcgtgcga ttacggcagc gattggcgcg | 1500 |
| ggggtaggaa ctgagttcac gctggaagac agcaattatt ccaaaatcat cattatgacc | 1560 |
| gatgcagata cagatggcgc gcacattcaa gtactgttgt tgacgttctt ttatcggtac | 1620 |
| atgaaagaac tcattgatgc aggacgcata tttattgctc agccgccatt gtataaaata | 1680 |
| acccgcaagt cgggtaagct cgaaacggtt cgttatgcct ggactgacga gcagcttgat | 1740 |
| aattacttaa aagaatttgg acgaaatttt gagcttcaac gttataaagg actcggggag | 1800 |
| atgaaccctg atcagttatg ggaaacgaca atgaatcccg agtcacgcac cctgttgcgc | 1860 |
| gttcagattg aggatgctgc caaagctgaa cgccgtgtgt ccacattgat gggtgataag | 1920 |
| gtggatccac gtaagcgctg gatcgtggaa aacgtggatt tcacggaata cgtagagtag | 1980 |

<210> SEQ ID NO 11
<211> LENGTH: 1116
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu17007 recF

<400> SEQUENCE: 11

| | |
|---|---|
| gtgtttgtga acaacattgt tttgcagcag taccggaact ataaacagct ggagctgaat | 60 |
| gaattcgggc ccgttaattt gctgatcgga caaaatgcgc aaggcaaaac gaatctggtt | 120 |
| gaggcgattt ttgtattagc cttaactaaa agtcaccgaa cgtcccgtga caaggaatta | 180 |
| atttctttcg gggctacttc cacacatcta gctgctgatg tggataagaa atacgggaaa | 240 |
| atcagattgg atctctcgtt atccacacaa ggcaaaaaag caaagatcaa cgggctagag | 300 |
| cagcgaaagc tgagcgattt tatcggttcg ttaaacgtgg tcatgtttgc gcccgaggat | 360 |
| ctggaaattg tcaaaggaac accgggggtt cgccgccggt ttcttgacat ggaaattgga | 420 |
| caagttgcgc caggatattt gtatcatttg cagcaatatc agaaagtgct ggttcagcgg | 480 |
| aataacctgc tcaagcaagc ttgggggaaa gatatggcgt ccgtgcagct gatgctggag | 540 |
| gtatggaatg agcaacttgt tgagcatggt gttaaaattg taaaaaagcg gaaacaattt | 600 |
| ataacaaagc tacaaaagtg ggcccaagcc attcatgaag ggattgcagg tgggacagaa | 660 |
| gagttaaaat tagcctatgt tccctctttc ggtgagccag aggaagaaga tgaagctgtc | 720 |
| ttattggagc gatttatgat aaagttatcc caaatgaggg aacaggaaat ccgccgtggc | 780 |
| atgactttgg cgggacccca tcgtgatgat ttggcctttg ccattaacgg cagagaagtg | 840 |
| catacgtatg gctctcaggg gcagcagcgg acgacggccc tgtctttgaa gctggccgaa | 900 |
| atagaattaa ttcatgagga aattggggag tatcctatcc tgctgctgga tgatgtattg | 960 |
| tccgagctgg accccatcg tcagactcag ctgatcgaga ctttccaaag caaggtacag | 1020 |
| acctttatca cggcaaccgg gattgagacg ttgaacgcag aacgacttaa gggtgcccat | 1080 |
| atttatcacg tccacgacgg gcatgtggaa cactaa | 1116 |

<210> SEQ ID NO 12
<211> LENGTH: 1719
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu17007 recN

<400> SEQUENCE: 12

```
atgctggtca ctttgtctat acggaatttg gcagtcgtag aagctgtcga tgttcatttt      60
tataaaggat ttcatgtatt gagcggagaa actggtgctg gtaaatccat tattatcgac     120
gcacttgggc tgattgcggg cggcagggga tctgctgatc tagtgcgtta cggatgtgat     180
aaagccgaaa tggaagcctt gtttgaattg ccggtcaaac atcccgtttg aatacgttg      240
gaggaacaag ggattaaggc taatccagaa gagcatttgc tgattcgtcg agaacttaca     300
gttcaggga aaagctcatc tcgaattaac ggtcagatgg ttaatttaac gatgctgcgt      360
gaggtaggtg agcaactcgt taatatccac gggcagcatg agcatcaaag cttgctgcgt     420
gcggatcgcc atcttgcgct gctggatacg ttcggtgact cggtcattgg tccagtcaaa     480
gcgctttacc gggagcgcta caatgctttt gtcaaagcgg aaaagaagt aagagaattg      540
caaagctcca gtcaaaaggc ttatcagcta ttggacatgt atcgcttcca attggaagag     600
atcgctgcgg cggagttaaa attgggtgaa gatgaattat tggcagagga acgggtcaag     660
ctatcccata gtgagaaaat gatggatgga gtatcaggag catacgagct gttaagtggc     720
agaggtggtc tggatacggt caataacgtg ttgtccagat taaatgatgt tcagagctac     780
gacagtaaaa gccttcagcc cattgcggag cagattcaat ctgctttcta tcagttggag     840
gatgcagcgt ttcaattacg ctcttatcgt gaggatattg aatttaatcc gggcaagctg     900
catgaggtgg agcaacgttt gaatcaaatt accgggttac agcgaaaata tggtgatagt     960
atagagcaga ttttggaata ctatagccgt attgagcagg aaaccgatct gttggaaaat    1020
aaagatgagc ggctggagca gctcattgca aagcgggatg agttgctttc gaatttgctg    1080
gagattgctg aagagcttac agaggcacgt gaaatttgtg ctgaagagct tgcagagcaa    1140
gtagagcagg aattaaaaga tcttcaaatg gaaagaacgt cactcaaggt gcgtattgat    1200
ccaattgaag atccacgtgg atatgaatat aaaggtctaa aggtacgacc taccaagcaa    1260
gggatagata atgcggaatt tctgatttcg cccaatccag gtgagccact tcgcccactc    1320
ggtaaaatcg cttccggtgg tgagttatca cgtatcatgt tggcgatgaa aagtattttt    1380
gcgcgtcatg atcaaattcc ggtgctcatt tttgacgagg tggataccgg ggtaagtggt    1440
cgtgcagctc agtccatagc cgagaagctt tatcgtttgt cttccgtttg tcaggtgttt    1500
tccattactc atttgccgca ggtggcatgt atggcagatc atcagtacct gattgagaaa    1560
aatgttcatg acggacggac catgactcaa attgagggac taacggagga aggtcgtgtt    1620
aaggaattgg cacggatgct gggtgggta gaaattaccg aaaaacatt gcatcacgca      1680
caggaaatgc tgaatttggc ggaaggaaag aaagcctga                           1719
```

<210> SEQ ID NO 13
<211> LENGTH: 945
<212> TYPE: DNA
<213> ORGANISM: Paenibacillus polymyxa spp. plantarum
<220> FEATURE:
<221> NAME/KEY: misc_feature
<223> OTHER INFORMATION: Strain Lu17007 rpoA

<400> SEQUENCE: 13

```
gtgatagaaa tcgaaaagcc gaaaattgag acggttgacg tcaatgatga tggcacctat      60
ggaaaattcg tagtagaacc gctggaacgc ggatacggta cgacgcttgg gaactcgctt     120
cgccgtattc tgttatcctc gttaccgggg gcagcagtca catcggttca gatcgatggg     180
```

| | |
|---|---|
| gttctgcacg agtttgcaac ggttcccggt gtgaaggaag acgtaacgga gatcattctg | 240 |
| aacttgaaag ctttatcgct taaaatccac tcagatgaag agaaagtact tgaaatcgat | 300 |
| gcggaaggcg aaggagttgt aacggcaggt gatatccgtg cggatagtga tgtggaaatt | 360 |
| cttaatccgg atcttcacat tgcaacgctc ggaccgggtt cgagacttca catgcgtatt | 420 |
| tttgccaatc gcggtcgcgg ttacgttaag caggatcgga ataaacgtga tgaccagccg | 480 |
| atcggcgtca ttcccgtcga ctccatctac actccgattg cacgcgtgaa ctacggcgta | 540 |
| gaaaatacgc gtgtcggcca ggttacgaat tatgacaagc tgacacttga ggtttggact | 600 |
| gacggaacta ttcgtcctga agaagctgtg agccttggag ccaaaatttt gaccgagcat | 660 |
| gtgatgctat tcgtgggtct cacggatgaa gcaaaagatg cagaaattat ggtcgaaaaa | 720 |
| gaagaagaca aaaagaaaa agttcttgaa atgacgatcg aagagctgga tctctccgtc | 780 |
| cgttcctata actgccttaa gcgcgctggt atcaatacgg tacaagaact cacgactaaa | 840 |
| tctgaagaag atatgatgaa ggtccgtaac ttgggtcgca atctttggat agaagtacaa | 900 |
| gagaagctcg aggaacttgg tttaggactt cgtacggaag aatag | 945 |

<210> SEQ ID NO 14
<211> LENGTH: 1143
<212> TYPE: DNA
<213> ORGANISM: Paenibacillus epiphyticus
<220> FEATURE:
<221> NAME/KEY: misc_feature
<223> OTHER INFORMATION: Strain Lu17015 dnaN

<400> SEQUENCE: 14

| | |
|---|---|
| atgaagatca gcattctgaa aaacgttttg aacgaggcta tacaacatgt atccaaagcg | 60 |
| atatcaagtc ggactacgat tccaattctg agtggtatta agctggatgt gaatcaccag | 120 |
| ggagtaacgc tgaccgccag cgatacagac atctccattc aatcctttat tccgatggag | 180 |
| gatggtgacc aaactgttgt tcaggtcgaa caacccggca gtgttgtgct gcctgccaaa | 240 |
| ttctttgtcg aaattatcaa aaagttgccg tcgcaggaga tccatatgga ggtaaaagac | 300 |
| caatttcaaa cctttatctc gtctggcgca actgaaattc agattgttgg cttggacccct | 360 |
| gaagaattcc cggtgcttcc caacattgaa gaaaatcaag tcatctctgt accaggagat | 420 |
| ttacttaaaa atatgattaa acagacggta ttctccatct ccacccacga aacgacaccg | 480 |
| attttaactg gcgtgttgtg gaatctggct gagggtgaat tgaagtttgt ggcaacggac | 540 |
| cgccaccgcc ttgccacccg tagcgctcat ttggagacgt ctgaaggctt gcgttttagc | 600 |
| aatgttgtca ttgcgggcaa aacgctgaat gagctgagca gaattattcc agatcaaaat | 660 |
| atgcttgtgg atatcgtagt agcggacaat caggtattat tcaaagtaga tcgggtgcta | 720 |
| ttttattccc gcatcttgga cggcacctat cctgatactt ctagaattat tccgacctcc | 780 |
| tacaaaacag aactgattgt ggatacaaaa agtttaagtg agtcaattga ccgtgcttat | 840 |
| ttgctgtccc gtgaggaaaa aacgaatatt gtaaaaatgc agtcgctgga aatggcggt | 900 |
| ttggagattt cctctagttc ctctgagctt ggcaaagtgc gtgaggaagt aactgtgtcc | 960 |
| aaatttgagg gagagccgct caaaatttcg ttcaactcta atacatgct cgacgtgctg | 1020 |
| aaggtgattg acagcgagca gctgacgatt gcttttaccg gcattatgag ccccattatt | 1080 |
| ttaaaaccgg ctgattccag caatgcgctg tatatcatcc tgccatatcg cacaaccaac | 1140 |
| tga | 1143 |

<210> SEQ ID NO 15
<211> LENGTH: 1980
<212> TYPE: DNA
<213> ORGANISM: Paenibacillus epiphyticus
<220> FEATURE:
<221> NAME/KEY: misc_feature
<223> OTHER INFORMATION: Strain Lu17015 gyrB

<400> SEQUENCE: 15

| | | | | | |
|---|---|---|---|---|---|
| atggtcgaca | aaatcgactt | gtctgcggga | gtgtccggca | cacaaagcgg | agcttcggaa | 60 |
| tatggcgcgg | acgacattca | agtgctcgaa | gggcttgtgg | cagttcgcaa | acggccgggc | 120 |
| atgtacatcg | ggagcaccag | ttcttcgggg | ctgcatcatt | tggtatggga | aattgtagac | 180 |
| aacgcggtgg | atgaacatct | cgccaagttt | tgctctcgca | ttgatattac | aatgcataag | 240 |
| gacggttccg | ttacagtatc | agacaacggg | cgcggtattc | ctacgggaat | gcacaaaacg | 300 |
| ggaattccta | cgcctcaggt | tgtattcacc | attttgcacg | ccggaggtaa | gtttggcggt | 360 |
| tcgggatata | aaaatccgg | gggtctgcac | ggtgtaggtg | cgtctgtaac | gaacgctctt | 420 |
| tcggaatggc | ttgaagtaga | aatttaccgg | gacggcaaga | ttcaccgtca | gcggtttgaa | 480 |
| tattggcagg | acaagaaggg | cgtggagcat | gtcggggaac | cgaccacagg | ccttgaagtg | 540 |
| ctgggcaata | ctaacaagac | gggctcgaaa | attacattta | aaccggatat | tcgtgttttt | 600 |
| caggcaggca | ttcattttaa | ctacgatacg | ttggctgagc | gccttcagga | aattgctttt | 660 |
| ctaaattcgg | gccttcgtat | tcaacttaaa | gacgaacgca | gcggaaagtc | agatgagtat | 720 |
| ttttatgagg | gtggcgcaag | tcagtttgtt | gcttttctga | atgagggcaa | ggatgtgctg | 780 |
| catgacgtta | ttcactttaa | tgccgagaaa | gaagacattg | aagtagagat | tgccatccag | 840 |
| tacaatgctg | gttatacaga | gacgattgct | tcgttcgtta | actccattcc | gacacgtgga | 900 |
| ggaggtacgc | atgaaacggg | attcaaaacc | gcttacactc | gtgtcatgaa | cgactatgcc | 960 |
| cggaaaacgg | tgatgttgaa | agaaaaggat | aaaaacttgg | agggcaacga | tctacgtgag | 1020 |
| ggcatgatgg | ctgtaatcag | tgtcaagatg | gctgaggttg | aatttgtcgg | ccagacaaag | 1080 |
| gatcagctgg | gaagcgcttc | ggcacggagt | acagtggatg | ccatcgtatc | tgagcagatg | 1140 |
| cagcgttttt | tggaagaaaa | tccgcagata | gcacaaactt | tgatcaagaa | ggcagttcaa | 1200 |
| gcatccagag | cacgtgaagc | tgcacgtaaa | gctcgggatg | aaatgcgttc | cggtaaaaag | 1260 |
| cgcagtgaaa | gttccaattt | gaatggtaaa | ctatcgcctg | cgcagtccaa | ggattttaca | 1320 |
| cgtaatgagt | tgtttattgt | ggaaggcgat | tcggctggag | gatcagccaa | gcagggacgg | 1380 |
| gattccaaaa | ttcaggccat | attgccgcta | aagggcaagc | cgatgaatcc | ggaaaaatcc | 1440 |
| aaactggcgg | atattatgaa | gaatgatgag | taccgtgcta | ttacagcagc | tattggtgcg | 1500 |
| ggagtaggaa | cagagttttc | gctggaagac | agcaattatt | ccaaaatcat | cattatgacc | 1560 |
| gatgcagata | cagatggtgc | gcacattcaa | gtgctgttgt | tgacgttctt | ttatcggtac | 1620 |
| atgaaagagc | ttattgatgc | aggacgcata | tttattgctc | aaccgccatt | gtataaaata | 1680 |
| actcgaaagt | cgggtaagct | cgaaacggtg | cgttatgctt | ggactgacga | gcagcttgat | 1740 |
| aattatttaa | aagaatttgg | acgaaatttt | gagcttcagc | gctataaagg | acttggggaa | 1800 |
| atgaaccctg | atcagttatg | ggaaacaacg | atgaatcccg | attcacgcac | cttgctacgc | 1860 |
| gttcagatag | aggatgcagc | caaggctgaa | cgcagggtgt | ccactttgat | gggtgataag | 1920 |
| gtggatccgc | gcaagcgctg | gatcgtggaa | aacgtagatt | ttacggaata | cgtagagtag | 1980 |

<210> SEQ ID NO 16
<211> LENGTH: 1116
<212> TYPE: DNA
<213> ORGANISM: Paenibacillus epiphyticus
<220> FEATURE:
<221> NAME/KEY: misc_feature
<223> OTHER INFORMATION: Strain Lu17015 recF

<400> SEQUENCE: 16

```
gtgtttgtga acaacattgt tttgcagcag taccggaact atgaacagct ggagctgaat      60
gaatttgggc ccgttaattt gctgatcgga caaaatgcgc agggcaaaac gaatctggta     120
gaggcaattt ttgtactggc tttaaccaaa agtcatcgaa cgtcccgcga caaggagtta     180
atctctttcg gggctacttc cactcaccta gctgcggatg tggataaaaa atacgggaaa     240
atcagactgg atctcgcgtt atccacacaa ggcaaaaaag caaagatcaa cggactggag     300
cagcgcaaac tgagcgattt tatcggttcg ttaaatgtgg tcatgtttgc acctgaggat     360
ctggaaattg tgaaaggaac accgggggtt cgccgccggt ttcttgacat ggaaatcgga     420
caggttgcgc caggatatct gtatcatttg cagcaatatc agaaagtatt ggttcagcga     480
aacaacctgc tcaagcaagc ttggggtaag atatggcgt cagtgcagct gatgctggag     540
gtatggaatg agcaacttgt tgagcatggt gttaaaattg ttaaaaagcg gaaacaattt     600
ataacaaagc tacaaaagtg ggctcaggcc attcatgaag ggatcgcagg tgggacagaa     660
gagttaaaat taacctatgt tccctccttc agtgagccag aggaagaaga tgaagctgtc     720
ttattggagc gatttatgat aaagttatcc caaatgaggg aacaggaaat ccgccgtggc     780
atgactttgg cgggaccca tcgtgacgat ttggcctttg ccattaacgg cagagaagtg     840
catacgtatg gctctcaggg gcagcagcgg acgacggccc tgtccttgaa gttggccgaa     900
atagagttaa ttcatgagga aattggtgaa tatcctgtct gctgctgga tgatgttttg     960
tccgagctgg acccctatcg tcagacccag ctgatcgaga cttccaaag caaggtacag    1020
accttatca cggcaaccgg ggttgagact ttgaacgcag aacgactcaa ggatgccaat    1080
atttatcacg tccacgacgg gcatgtggaa cactaa                             1116
```

<210> SEQ ID NO 17
<211> LENGTH: 1719
<212> TYPE: DNA
<213> ORGANISM: Paenibacillus epiphyticus
<220> FEATURE:
<221> NAME/KEY: misc_feature
<223> OTHER INFORMATION: Strain Lu17015 recN

<400> SEQUENCE: 17

```
atgctggtca ctttgtctat acggaatttg gcggtcgtag aggccgtcga tgttcatttt      60
tataaagggt ttcatgtctt gagcggggaa acaggtgctg gtaaatccat tattatcgat     120
gcgcttggcc tgattgcagg cggtaggggc tctgctgatc tagtgcgtta cggttgtgat     180
aaagcagaga tggaagcctt gtttgagctg ccggtaaaac atccagtttg gaaaacactt     240
gaggaacaag ggattaaggc caatgcggag gagcatttgc tgattcgtcg cgaacttacg     300
gttcaggga aaagctcttc tcgaattaac ggtcagatgg ttaatttaac gatgctgcgt     360
gaggtaggtg agcagctcgt caatatccac gggcaacatg agcatcaaag cctgctacgt     420
gcagatcgcc atctggcgct gctggatacg ttcggtgatt cggtgatcgg tccagtcaaa     480
acgctttacc gtgagcgtta caatgctttt gtcaaagcgg aaaaagaagt aagagaactg     540
caaagctcca gtcaaaaggc ttatcagctt ttggatatgt accgatttca attagaagag     600
```

```
atcgctgcgg cggagttgaa attgggagaa gatgaattat tggcagagga acgggtcaag    660
ctatcccata gtgagaaaat gatggatggg atatcaggag catacgaact gctaagcggc    720
agaggtgggc tggatacgat caataacgta ttgtctagat tgaacgatgt ccaaagctat    780
gacagcaaaa gccttcagcc cattgcggag cagattcagt ctgcttttta ccagttagag    840
gacgcagcat tccaattacg ttcttatcgt gaggatattg aatttaatcc aggcaagctg    900
catgaagtgg agcaacgttt gaatcaaatt accggattac agcgaaaata tggtgatagt    960
atagagcaga ttttggaata ctatagccgt attgagcagg aaaccgatct gctggaaaat   1020
aaagatgagc ggctggagca gctcattgca aaacgggatg agttgctttc cgatttgctg   1080
gagatttcag aagagcttac agaagcacgt gaaatttgtg ctgaagagct tgcagagcaa   1140
gtggagcagg agttaaaaga cctgcagatg gaaagaacgt cactcaaggt gcgcattgat   1200
ccaattgaag atccacgcgg atatgagtat aaaggtctga aggtaaggcc taccaagcaa   1260
ggaattgata atgcggaatt tcttatttca cccaatccag gtgagccact acgtccactt   1320
ggtaagatcg cttcaggcgg tgagctatca cgtatcatgt tggcgatgaa agtatttttt   1380
gcgcgtcatg atcaaattcc agtactcatt tttgacgagg tggataccgg ggtgagtggt   1440
cgtgcagctc aatccattgc cgagaagcta tatcgtttat cttccgtttg tcaggtgttt   1500
tccattactc atttgccaca ggtggcatgt atggcagatc atcagtacct tattgagaaa   1560
aatgttcatg atggacggac catgactcaa attgagggac ttacggagga cgggcgtgtc   1620
aaggaattgg cacggatgct gggcggcgtg gaaattaccg aaaaaacatt gcatcacgca   1680
caggaaatgc tgaatttggc ggaaggaaag aaagcctga                          1719

<210> SEQ ID NO 18
<211> LENGTH: 945
<212> TYPE: DNA
<213> ORGANISM: Paenibacillus epiphyticus
<220> FEATURE:
<221> NAME/KEY: misc_feature
<223> OTHER INFORMATION: Strain Lu17015 rpoA

<400> SEQUENCE: 18
gtgatagaaa tcgaaaagcc gaaaattgag acggttgacg tcaatgatga tggcacctat     60
ggaaaattcg tagtagaacc gctggaacgc ggatacggta cgacgttggg aaactcgctt    120
cgccgtattc tgttatcctc gttaccgggg gcagcagtca catcggttca gatcgatggg    180
gttctgcacg agtttgcaac ggttcccggt gtgaaggaag acgtaacgga gatcattctg    240
aacttgaaag cttatcgct taaaatccac tcggatgaag agaaagtact cgaaatcgat    300
gcggaaggcg aaggagttgt aacggcagga gatatccgtg cggatagtga tgtggaaatt    360
cttaatccgg atcttcacat tgctacgctc ggaccggggtt cgagacttca catgcgtatt    420
tttgccaatc gcggtcgcgg ttacgttaag caggatcgga acaaacgtga tgaccagccg    480
atcggcgtca ttcccgtcga ctccatctac actccgattg cacgcgtgaa ctacggcgta    540
gaaaatacgc gtgtcggcca ggttacgaat tacgacaagc tgcacttga ggtttggact    600 gacggaagta ttcgtcccga ggaagcagtg agccttggag ccaaaatttt gaccgagcat    660
gtgatgttgt tcgtgggtct cacggacgag gcaaagatg ctgaaattat ggttgaaaaa    720
gaagaagaca gaaagaaaa agttcttgaa atgacgatcg aagagctgga tctctccgtc    780
cgttcctata actgccttaa gcgcgctggt atcaatacgg tacaagaact cacgactaaa    840
```

```
tctgaagaag atatgatgaa ggtccgtaac ttgggtcgca aatctttgga agaagtacaa        900
gagaagctcg aggaacttgg tttaggactt cgtacggaag aatag                        945
```